(12) United States Patent
Skelly et al.

(10) Patent No.: US 11,081,240 B2
(45) Date of Patent: Aug. 3, 2021

(54) METHODS FOR TREATMENT OF HYPERTENSION WITH AN ANGIOTENSIN II RECEPTOR BLOCKER PHARMACEUTICAL COMPOSITION

(71) Applicant: AstraZeneca UK Limited, Cambridge (GB)

(72) Inventors: Richard L. Skelly, Flourtown, PA (US); Judy Firor, Landenberg, PA (US); James Blasetto, Chadds Ford, PA (US)

(73) Assignee: ASTRAZENECA UK LIMITED, Cambridge (GB)

( * ) Notice: Subject to any disclaimer, the term of this patent is extended or adjusted under 35 U.S.C. 154(b) by 230 days.

(21) Appl. No.: 16/440,839

(22) Filed: Jun. 13, 2019

(65) Prior Publication Data

US 2019/0385750 A1 Dec. 19, 2019

Related U.S. Application Data

(60) Provisional application No. 62/848,902, filed on May 16, 2019, provisional application No. 62/685,209, filed on Jun. 14, 2018.

(51) Int. Cl.
*G16H 70/40* (2018.01)
*G16H 50/30* (2018.01)
(Continued)

(52) U.S. Cl.
CPC ......... *G16H 70/40* (2018.01); *A61K 31/4245* (2013.01); *G16H 10/20* (2018.01);
(Continued)

(58) Field of Classification Search
None
See application file for complete search history.

(56) References Cited

U.S. PATENT DOCUMENTS 6,315,720 B1 * 11/2001 Williams ............... G16H 10/20
600/300
7,493,264 B1 2/2009 Kelly et al.
(Continued)

FOREIGN PATENT DOCUMENTS

WO WO 2010/041052 A1 4/2010

OTHER PUBLICATIONS

International Search Report and Written Opinion for International Patent Application No. PCT/US2019/037096 dated Nov. 20 219, 32 pages.
(Continued)

*Primary Examiner* — Aryan E Weisenfeld
*Assistant Examiner* — Karen A Hranek
(74) *Attorney, Agent, or Firm* — Morgan, Lewis & Bockius LLP; Brett A. Lovejoy; Andrew J. Antczak

(57) ABSTRACT

A method is provided for lowering blood pressure in a subject in need thereof by administering an angiotensin II receptor blocker pharmaceutical composition to a subject qualified for over-the-counter access to the angiotensin II receptor blocker pharmaceutical composition. In some embodiments, the angiotensin II receptor blocker pharmaceutical composition includes azilsartan medoxomil, candesartan, eprosartan, irbesartan, losartan, olmesartan, telmisartan, or valsartan. In some embodiments, the angiotensin II receptor blocker pharmaceutical composition comprises an active ingredient that is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate or a pharmaceutically acceptable salt thereof.

56 Claims, 23 Drawing Sheets

(51) Int. Cl.
*G16H 50/20* (2018.01)
*A61K 31/4245* (2006.01)
*G16H 10/20* (2018.01)
*G16H 20/10* (2018.01)

(52) U.S. Cl.
CPC ............ *G16H 20/10* (2018.01); *G16H 50/20* (2018.01); *G16H 50/30* (2018.01)

(56) References Cited

U.S. PATENT DOCUMENTS

| | | | |
|---|---|---|---|
| 2005/0108053 A1 | 5/2005 | Jones | |
| 2006/0129433 A1* | 6/2006 | Koneru | G16H 20/10 705/3 |
| 2006/0281795 A1 | 12/2006 | Kuroita et al. | |
| 2009/0125324 A1* | 5/2009 | Keravich | G16H 20/13 705/2 |
| 2011/0166876 A1 | 7/2011 | Chapman | |
| 2011/0178812 A1 | 7/2011 | Lindsay | |
| 2011/0245967 A1* | 10/2011 | Shah | G07F 7/00 700/236 |
| 2012/0065999 A1* | 3/2012 | Takatoku | G06Q 10/10 705/3 |
| 2012/0150562 A1* | 6/2012 | Lerner | G16H 10/60 705/3 |
| 2016/0012203 A1* | 1/2016 | Huser | G16H 50/20 705/3 |
| 2016/0335411 A1* | 11/2016 | Czerwiec | H04L 63/10 |
| 2018/0165739 A1* | 6/2018 | Lawless | G16H 10/60 |
| 2021/0005301 A1* | 1/2021 | Penta | G06Q 30/00 |

OTHER PUBLICATIONS

Dezsi, "The Different Therapeutic Choices with the ARBs. Which One to Give? When? Why?", American Journal of Cardiovascular Druvs, vol. 16, No. 4, Mar. 3, 2016.
Radl et al., "Improved Process for Azilsartan Medoxomil: A New Angiotensin Receptor Blocker", Organic Process Research and Development, American Chemical Society, vol. 17, No. 1, Dec. 18, 2012.
Goff et al., "2013 ACC/AHA Guideline on the Assessment of Cardiovascular Risk a Report of the American College of Cardiology/American Heart Association Task Force on Practice Guidelines", Journal of the American College of Cardiology, Elsevier, New York, NY, vol. 63, No. 25, Nov. 12, 2013.
Perk et al., "European Guidelines on cardiovascular disease prevention in clinical practice (version 2012): The Fifth Joint Task Force of the European Society of Cardiovascular Disease Prevention in Clinical Practice", European Heart Journal, vol. 33, No. 13, May 3, 2021.
Abraham et al., "The Comparative Efficacy and Safety of the Angiotensin Receptor Blockers in the Management of Hypertension and Other Cardiovascular Diseases", Drug Safety, vol. 38, No. 1, Nov. 22, 2014.
Ramkumar, S. et al., Acta Cardiol. Sin., 32(6):631-39 (2016).
Barlas S. FDA Considers a New Paradigm for Over-the-Counter Medications: More Power—but More Burdens—for Pharmacists and Pharmacies. P T. May 2012;37(5):300-5. PubMed PMID: 22876088; PubMed Central PMCID: PMC3411219.
Crestor, Full Prescribing Information, 2012, AstraZeneca Pharmaceuticals LP.
Dyer O., "FDA Rejects sale of over the counter Statins", BMJ, Jan. 22, 2005; 330(7484):164.
May 9, 2013, power point presentations from the Engelberg Center for Health Care Reform.
Pfizer Wants Atorvastatin Available Over the Counter—Medscape—Aug. 4, 2011, downloaded from the Internet Nov. 30, 2018.
PR Newswire Association, "Americans Should Pay More Attention to Over-the-Counter (OTC) medicine Labels According to New Survey", Oct. 15, 2015 (citing McNeil Consumer Healthcare research).
Atacand® (candesartan cilexetil) Tablets Prescribing Information, (AstraZeneca) Feb. 2015, [online], [retrieved on Feb. 24, 2021], Retrieved from the Internet: <URL: https://www.accessdata.fda.gov/drugsatfda_docs/label/2015/020838s036lbl.pdf>.
Avapro®* (irbesartan) Tablets Prescribing Information (Sanofi-Aventis U.S. LLC) Feb. 2016, [online], [retrieved on Feb. 24, 2021] Retrieved from the Internet: <URL: https://www.accessdata.fda.gov/drugsatfda_docs/label/2016/020757s059s067lbl.pdf>.
Benicar (olmesartan med oxomil) Tablets Prescribing Information (Daiichi Sankyo, Inc.), Mar. 2012, [online], [retrieved on Feb. 24, 2021] Retrieved from the Internet: <URL: https://www.accessdata.fda.gov/drugsatfda_docs/label/2012/021286s023lbl.pdf>.
Cozaar® (losartan potassium) Tablets Prescribing Information (Merck & Co., Inc.) Oct. 2018, [online], [retrieved on Feb. 24, 2021] Retrieved from the Internet: <URL: https://www.accessdata.fda.gov/drugsatfda_docs/label/2018/020386s062lbl.pdf>.
Diovan® (valsartan) Tablets Prescribing Information (Novartis Pharmaceuticals Corp.) Jan. 2017, [online], [retrieved on Feb. 24, 2021] Retrieved from the Internet: <URL: https://www.accessdata.fda.gov/drugsatfda_docs/label/2017/021283s50lbl.pdf>.
Edarbi (azilsartan medoxomil) Tablets Prescribing Information (Takeda Pharmaceuticals America, Inc.) Feb. 2011, [online], [retrieved on Feb. 24, 2021] Retrieved from the Internet: <URL: https://www.accessdata.fda.gov/drugsatfda_docs/label/2011/200796s000lbl.pdf>.
Micardis® (telmisartan) Tablets Prescribing Information (Boehringer Ingelheim Pharmaceuticals, Inc.) Feb. 2011, [online], [retrieved on Feb. 24, 2021] Retrieved from the Internet: <URL: https://www.accessdata.fda.gov/drugsatfda_docs/label/2011/020850s032lbl.pdf>.
Teveten (eprosartan mesylate) Prescribing Information (AbbVie Inc.) Jul. 2014, [online], [retrieved on Feb. 24, 2021] Retrieved from the Internet: <URL: https://www.accessdata.fda.gov/drugsatfda_docs/label/2014/020738s029lbl.pdf>.

* cited by examiner

400

(402) Qualify a human subject for over-the-counter delivery of an angiotensin II receptor blocker pharmaceutical composition for lowering blood pressure.

(404) The angiotensin II receptor blocker pharmaceutical composition includes an active ingredient having a structure of structure (I).

(406) The angiotensin II receptor blocker pharmaceutical composition includes an active ingredient that is that is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate or a pharmaceutically acceptable salt thereof.

(408) The angiotensin II receptor blocker pharmaceutical composition includes an active ingredient that is azilsartan medoxomil, or a pharmaceutically acceptable salt thereof.

(410) The angiotensin II receptor blocker pharmaceutical composition includes an active ingredient selected from the group consisting of candesartan, eprosartan, irbesartan, losartan, olmesartan, telmisartan, and valsartan.

(412) The lowering blood pressure is to treat or prevent heart disease.

(414) Conduct an assessment survey of the subject thereby obtaining a plurality of assessment survey results.

(416) The plurality of assessment survey results includes whether the subject is one of (i) pregnant, (ii) breastfeeding, or (iii) planning to become pregnant, whether the subject is taking a medication that interacts with the angiotensin II receptor blocker pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, and whether the subject has ever had a kidney problem.

Fig. 4A

*(418)* Run all or a portion of the plurality of assessment survey results against a first plurality of filters of a first category class. When a respective filter in the first plurality of filters is fired, the subject is deemed not qualified for delivery of the angiotensin II receptor blocker pharmaceutical composition and the method is terminated without delivery of the angiotensin II receptor blocker pharmaceutical composition to the subject.

*(420)* The first plurality of assessment filters comprises a pregnancy assessment filter that is fired at least when the plurality of assessment survey results indicates that the subject is pregnant or the subject is breastfeeding.

*(422)* The pregnancy assessment filter is also fired when the plurality of assessment survey results indicates that the subject is planning to become pregnant.

*(424)* The first plurality of assessment filters comprises a drug interaction assessment filter that is fired at least when the plurality of assessment survey results indicates that the subject is a medication that interacts with the angiotensin II receptor blocker pharmaceutical composition.

*(426)* The drug interaction assessment filter is fired when the plurality of assessment survey results indicates that the subject is taking a lithium medication.

*(428)* The drug interaction assessment filter is fired when the plurality of assessment survey results indicates that the subject is taking a non-steroidal anti-inflammatory medication.

*(430)* The drug interaction assessment filter is fired when the plurality of assessment survey results indicates that the subject is taking a high blood pressure medication.

*(432)* The first plurality of assessment filters comprises a blood pressure assessment filter that is fired at least when the plurality of assessment survey results indicates the subject is not hypertensive or the subject has severe hypertension.

*(434)* Blood pressure that indicates the subject is not hypertensive, and is capable of firing the blood pressure assessment filter, is a systolic blood pressure of less than 130 mm Hg and a diastolic blood pressure of less than 80 mm Hg.

*(436)* Blood pressure that indicates the subject has severe hypertension, and is capable of firing the blood pressure assessment filter, is a systolic blood pressure of at least 140 mm Hg or a diastolic blood pressure of at least 90 mm Hg.

*(438)* When the plurality of assessment survey results indicate that the subject has elevated blood pressure but is not hypertensive, firing the blood pressure assessment filter, and transmitting, to the subject, advice to manage their blood pressure by eating healthy and exercising.

*(440)* When the plurality of assessment survey results indicate that the subject has stage two hypertension, firing the blood pressure assessment filter, and transmitting, to the subject, advice to visit a doctor to discuss taking a prescription-strength blood pressure medication.

*(442)* When the plurality of assessment survey results indicate that the subject is in hypertension crisis, firing the blood pressure assessment filter, and transmitting, to the subject, advice to seek emergency medical attention.

*(444)* The first plurality of assessment filters comprises an age assessment filter.

*(446)* The age assessment filter is fired when the plurality of assessment survey results indicates that the subject is too young to receive the angiotensin II receptor blocker pharmaceutical composition.

*(448)* The first plurality of assessment filters comprises a pooled cohort equation assessment filter that is fired at least when the plurality of assessment survey results indicate that the subject has a risk for atherosclerotic cardiovascular disease that is below a floor threshold of risk or the subject has an incalculable risk for atherosclerotic cardiovascular disease.

*(450)* The pooled cohort equation filter is fired when the plurality of assessment survey results indicates the subject has a 10-year risk for atherosclerotic cardiovascular disease, as determined using the pooled cohort equation, that is less than 10%.

*(452)* The pooled cohort equation is implemented as a multivariable Cox proportional hazard regression.

*(454)* The pooled cohort equation assessment filter is fired when the plurality of assessment survey results indicates that the subject has an incalculable risk for atherosclerotic cardiovascular disease, as determined by one or more inputs of the pooled cohort equation, including the subject is younger than forty years old, a total cholesterol level of the subject is either less than 160 mg / dL or greater than 240 mg / dL, a high density lipoprotein cholesterol level of the subject is less than 45 mg / dL or greater than 65 mg / dL, an untreated systolic blood pressure of the subject is less than 100 mm Hg or greater than 140 mm Hg, or a treated systolic blood pressure of the subject is less than 120 mm Hg or greater than 160 mm Hg.

*(456)* Bypassing the firing of the pooled cohort equation assessment filter when the plurality of assessment survey results indicates that the subject has an incalculable risk for atherosclerotic cardiovascular disease but has an age that is above a risk threshold age.

*(458)* The plurality of assessment survey results further comprises a gender of the subject, a race of the subject, a blood pressure medication status of the subject, a smoking status of the subject, a total cholesterol level of the subject, a high density lipoprotein cholesterol level of the subject, whether the subject has ever had an atherosclerotic cardiovascular history including an atherosclerotic event or a heard procedure, and a diabetes status of the subject. The pooled cohort equation assessment filter incorporates the gender of the subject, the age of the subject, the race of the subject, the blood pressure medication status of the subject, the smoking status of the subject, the total cholesterol of the subject, the high density lipoprotein cholesterol level of the subject, the atherosclerotic cardiovascular history of the subject, and the diabetes status of the subject to derive the risk for atherosclerotic cardiovascular disease.

*(460)* The plurality of assessment survey results further comprises whether the subject is allergic to the angiotensin II receptor blocker pharmaceutical composition, and the first plurality of assessment filters includes an adverse reaction assessment filter that is fired when the plurality of assessment survey results indicates that the subject is allergic to the angiotensin II receptor blocker pharmaceutical composition.

*(462)* The plurality of assessment survey results further comprises whether the subject has had a liver problem, and the first plurality of assessment filters includes a liver problem assessment filter that is fired when the plurality of assessment survey results indicates that the subject has advanced liver disease.

Fig. 4D

(464) Run all or a portion of the plurality of assessment survey results against a second plurality of assessment filters of a second category class. When a respective filter in the second plurality of assessment filters is fired, the subject is provided with a warning corresponding to the respective filter.

(466) The second plurality of assessment filters comprises a kidney problem assessment filter that is fired at least when the plurality of assessment survey results indicates that the subject has had a kidney problem.

(468) The second plurality of assessment filters comprises an electrolyte blood level monitor assessment filter that is fired at least when the plurality of assessment survey results indicates that the subject has had an abnormal electrolyte blood level.

(470) The plurality of assessment survey results further comprises whether the subject is taking a potassium supplement or a salt substitute that includes potassium, and the second plurality of assessment filters includes a potassium supplement assessment filter that is fired when the plurality of assessment survey results indicates that the subject is taking a potassium supplement or a salt substitute that includes potassium.

(472) The plurality of assessment survey results further comprises whether the subject has ever had a heart failure, and the second plurality of assessment filters includes a heart failure assessment filter that is fired when the plurality of assessment survey results indicates that the subject has had a heart failure.

(474) The plurality of assessment survey results further comprises whether the subject is taking colesevelam, and the second plurality of assessment filters includes a colesevelam interaction assessment filter that is fired when the plurality of assessment survey results indicates that the subject is taking colesevelam.

(476) The warning corresponding to a respective filter in the second plurality of assessment filters comprises a prompt for the subject to indicate whether they have discussed the risk factor underlying the respective filter in the second plurality of assessment filters that was fired with a health care provider. Acknowledgement is obtained from the subject when the subject indicates that they have discussed the risk factor underlying the respective filter in the second plurality of assessment filters that was fired with a health care provider.

(478) Obtain acknowledgment from the subject for the warning issued to the subject by any filter in the second plurality of assessment filters.

Fig. 4E

*(480)* Proceed with a fulfillment process when no filter in the first plurality of assessment filters has been fired and the subject has acknowledged each warning associated with each filter in the second plurality of assessment filters that was fired.

*(482)* The fulfillment process comprises storing an indication in a subject profile of an initial order for the angiotensin II receptor blocker pharmaceutical composition, communicating an over the counter drug facts label for the angiotensin II receptor blocker pharmaceutical composition to the subject, and authorizing, upon confirmation from the subject that the over the counter drug facts label has been received and read, provision of the angiotensin II receptor blocker pharmaceutical composition to the subject.

*(484)* Upon confirmation from the subject that the over the counter drug facts label has been received and read, the subject is authorized for provision of a dosage of from 40 mg to 80 mg per day of the active ingredient of the angiotensin II receptor blocker pharmaceutical composition.

*(486)* The fulfillment process further comprises storing a destination associated with the subject in the subject profile.

*(488)* The fulfillment process further comprises coordinating shipping of the angiotensin II receptor blocker pharmaceutical composition to a physical address associated with the subject.

*(502)* Requalifying a human subject for over-the-counter delivery of a angiotensin II receptor blocker pharmaceutical composition for lowering blood pressure. The computer system includes one or more processors and a memory. The memory includes non-transitory instructions which, when executed by the one or more processor, perform a method.

*(504)* The angiotensin II receptor blocker pharmaceutical composition is selected from the group consisting of azilsartan medoxomil, candesartan, eprosartan, irbesartan, losartan, olmesartan, telmisartan, and valsartan.

*(506)* The lowering blood pressure is to treat or prevent heart disease.

*(508)* Responsive to receiving a re-order request from the subject for the angiotensin II receptor blocker pharmaceutical composition, conducting a reassessment survey of the subject thereby obtaining a plurality of reassessment survey results.

*(510)* The plurality of reassessment survey results comprises a systolic blood pressure of the subject, a diastolic blood pressure of the subject, whether the subject is one of (i) pregnant, (ii) breastfeeding, or (iii) planning to become pregnant, whether the subject is taking a medication that interacts with the angiotensin II receptor blocker pharmaceutical composition, whether the subject has experienced symptoms of hypotension since receiving their last provision of the angiotensin II receptor blocker pharmaceutical composition, whether the subject has developed an abnormal electrolyte blood level since receiving their last provision of the angiotensin II receptor blocker pharmaceutical composition, and whether the subject has developed a kidney problem since receiving their last provision of the angiotensin II receptor blocker pharmaceutical composition.

*(512)* Run all or a portion of the plurality of reassessment survey results against a first plurality of reassessment filters of the first category class. When a respective filter in the first plurality of reassessment filters is fired, the subject is deemed not qualified for the angiotensin II receptor blocker pharmaceutical composition and the re-fulfillment process is terminated without delivery of the angiotensin II receptor blocker pharmaceutical composition to the subject.

*(514)* The first plurality of reassessment filters comprises a blood pressure reassessment filter that is fired at least when the plurality of reassessment survey results indicates that the subject has hypertension.

*(516)* The first plurality of reassessment filters comprises a pregnancy reassessment filter that is fired at least when the plurality of assessment survey results indicates that the subject is pregnant or the subject is breastfeeding.

*(518)* The pregnancy reassessment filter is also fired when the plurality of reassessment survey results indicates that the subject is planning to become pregnant.

*(520)* The first plurality of reassessment filters comprises a drug interaction reassessment filter that is fired at least when the plurality of reassessment survey results indicates the subject is taking a medication that interacts with the angiotensin II receptor blocker pharmaceutical composition.

*(522)* The drug interaction reassessment filter is fired when the plurality of reassessment survey results indicates that the subject is taking a lithium medication.

*(524)* The drug interaction reassessment filter is fired when the plurality of reassessment survey results indicates that the subject is taking a non-steroidal anti-inflammatory medication.

*(526)* The drug interaction reassessment filter is fired when the plurality of reassessment survey results indicates that the subject is taking a high blood pressure medication.

*(528)* The first plurality of reassessment filters comprises a hypotension reassessment filter that is fired at least when the plurality of reassessment survey results indicates that the subject has experienced symptoms of hypotension since receiving their last provision of the angiotensin II receptor blocker pharmaceutical composition.

*(530)* The first plurality of reassessment filters comprises an electrolyte blood level monitor reassessment filter that is fired at least when the plurality of reassessment survey results indicates that the subject has developed an abnormal electrolyte blood level since receiving their last provision of the angiotensin II receptor blocker pharmaceutical composition.

*(532)* The first plurality of reassessment filters comprises a kidney problem reassessment filter that the plurality of reassessment survey results indicates that the subject has developed an abnormal electrolyte blood level since receiving their last provision of the angiotensin II receptor blocker pharmaceutical composition..

Fig. 5B

(534) Run all or a portion of the plurality of reassessment survey results against a second plurality of reassessment filters of the second category class. When a respective filter in the second plurality of reassessment filters is fired, the subject is provided with a warning corresponding to the respective filter.

(536) The plurality of reassessment results further comprise whether the subject has experienced an impaired renal function since receiving their last provision of the angiotensin II receptor blocker pharmaceutical composition. The second plurality of reassessment filters comprises a renal function reassessment filter that is fired at least when the plurality of reassessment results indicates that the subject has experienced, since receiving their last provision of the angiotensin II receptor blocker pharmaceutical composition, an impaired renal function.

(538) The plurality of reassessment results further comprise whether the subject has experienced an abnormal potassium serum level since receiving their last provision of the angiotensin II receptor blocker pharmaceutical composition. The second plurality of reassessment filters comprises a potassium serum level reassessment filter that is fired at least when the plurality of reassessment results indicates that the subject has experienced, since receiving their last provision of the angiotensin II receptor blocker pharmaceutical composition, an abnormal potassium serum level.

(540) The plurality of reassessment results further comprise whether the subject has experienced a side effect associated with the angiotensin II receptor blocker pharmaceutical composition since receiving their last provision of the angiotensin II receptor blocker pharmaceutical composition. The second plurality of reassessment filters comprises a side effect reassessment filter that is fired at least when the plurality of reassessment results indicates that the subject has experienced, since receiving their last provision of the angiotensin II receptor blocker pharmaceutical composition, an a side effect selected from the group consisting of hypotension, dizziness, and faintness.

(542) Obtain acknowledgment from the subject for the warning issued to the subject by any filter in the second plurality of reassessment filters.

Fig. 5C

(544) Proceed with the re-fulfillment process when the re-fulfillment process is not already terminated by the firing of a filter in the first plurality of reassessment filters and the subject has acknowledged each warning associated with each filter in the second plurality of reassessment filters that was fired.

(546) The re-fulfillment process further comprises, when a respective filter in the first plurality of reassessment filters or second plurality of reassessment filters is fired, storing a record associated with the firing of the respective filter in an adverse event profile comprising records of filter firing events associated with a plurality of subjects.

(548) The re-fulfillment process further comprises storing an indication in the subject profile of a re-order for the angiotensin II receptor blocker pharmaceutical composition, communicating the over the counter drug facts label for the angiotensin II receptor blocker pharmaceutical composition to the subject, and authorizing, upon confirmation from the subject that the over the counter drug facts label has been received and read, a re-order provision of the angiotensin II receptor blocker pharmaceutical composition to the subject.

Fig. 5D

Have you been told that you have abnormal body salt (electrolytes) levels in your blood? — 650
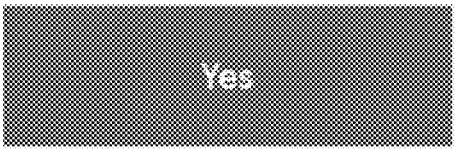 
Fig. 6A
Users with abnormal body salt levels in their blood are known to have adverse effects when taking with angiotensin II receptor blockers. — 652
Please consult with your doctor before taking angiotensin II receptor blocker OTC.
Fig. 6B Are you pregnant or breastfeeding, think you may be pregnant, or plan to become pregnant?

Have you ever had a kidney problem?

Are you taking any of the following:

Aliskiren and have diabetes or a renal problem?

Lithium medicines including those to treat depression?

Non-steroidal anti-inflammatory drugs such as ibuprofen or naproxen?

Medicines that treat high blood pressure or heart problems, including diuretics such as water pills?

— 658

Yes No
Yes No
Yes No
Yes No

Angiotensin II receptor OTC may not be right for you. Based on your answers, it is important to talk to your doctor about potential risks of taking angiotensin II receptor OTC. It may be helpful to have your summary of answers when talking to your doctor.

Has your doctor said it is OK for you to take angiotensin II receptor OTC?

[ Yes ]  [ No, View/Print Summary ]

Fig. 7

METHODS FOR TREATMENT OF HYPERTENSION WITH AN ANGIOTENSIN II RECEPTOR BLOCKER PHARMACEUTICAL COMPOSITION

CROSS REFERENCE TO RELATED APPLICATIONS

This application claims priority to U.S. Provisional Patent Application Ser. No. 62/685,209, filed Jun. 14, 2018, and claims priority to U.S. Provisional Patent Application Ser. No. 62/848,902, filed May 16, 2019, both of which are hereby incorporated by reference in their entireties.

TECHNICAL FIELD

The present disclosure relates generally to methods for lowering blood pressure, e.g., thereby treating and/or preventing heart disease, by administering an over-the-counter angiotensin II receptor blocker pharmaceutical composition to a subject in need thereof, who has been qualified for over-the-counter access to the composition.

BACKGROUND

Hypertension, e.g., high blood pressure, is the leading cause of death worldwide and the second-leading cause of preventable death in the United States. Roberts, N., et al., Emitro Health, "Feeling the Pressure of New Guidelines for the Treatment of Hypertension," (2017). As of 2014, according to the CDC, 1 in 3 adults in the U.S. was inflicted with high blood pressure and about 46% of those individuals did not have their blood pressure under control. Merai R., et al., MMWR Morb Mortal Wkly Rep, 65:1261-1264 (2016). Of the approximately 35 million U.S. citizens that do not have their blood pressure under control, about 20% are aware that they have high blood pressure, yet are not being treated. Id. The CDC estimates that $49 billion is spent annually in direct and indirect medical expenses relating to uncontrolled hypertension. Id.

Fortunately, hypertension can be managed, for example, using angiotensin II receptor blockers, which are well established prescription pharmaceuticals used to lower blood pressure, thereby preventing heart disease. For instance, the efficacy of azilsartan medoxomil, which was first approved in the U.S. for the treatment of hypertension in 2011, to lower blood pressure has been demonstrated in at least 5 double-blind, placebo-controlled, randomized studies. However, access to angiotensin II receptor blockers is restricted by the requirement for a prescription. Unfortunately, long-term trends demonstrate many people avoid prescription medications, including angiotensin II receptor blockers.

One approach to making angiotensin II receptor blockers more accessible is to make them available without a prescription, e.g., over the counter ("OTC"). There are a variety of health benefits derived from switching a drug from prescription to OTC including, but not limited to, generating wider availably to therapies, providing a greater number of therapeutic approaches, providing direct and rapid access to treatments, providing patients with an active role in their own health care, and allowing patients to become self-reliant in preventing and relieving minor symptoms or conditions (World Health Organization, 2000, "Guidelines for the Regulatory Assessment of Medicinal Products for use in Self-Medication," Print). Given the large number of individuals with uncontrolled high blood pressure, providing access to OTC angiotensin II receptor blockers could provide significant societal health benefits.

However, switching distribution of a pharmaceutical from prescription-only to OTC creates a significant risk that the patient population will be unable to appropriately self-select themselves for safe use of the pharmaceutical use and then self-medicate using the drug in a responsible manner. The manifestations embodied within these concerns include incorrect self-diagnosis, incorrect drug-qualification, unrecognized drug-drug interactions (DDI), unanticipated adverse drug reactions and/or side-effects, improper dosing and/or administration, masking of a disease, addiction, inappropriate drug dependency, substance abuse, and patient delay in seeking necessary medical attention. Ruiz et al., Current Drug Safety, 5(4):315 (2010).

In order to ensure the safety of OTC distribution of angiotensin II receptor blockers, prospective patients must effectively self-select themselves for the drug. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey," October 15 (2015) (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Currently, there are two regulatory pathways for legal marketing of an OTC drug in the United States. In the first pathway, marketing occurs in compliance with an OTC drug monograph, that sets regulatory standards for non-prescription drugs that are not covered by human drug applications, e.g., a New Drug Application (NDA) or Abbreviated New Drug Application (ANDA). An OTC monograph is created as a result of a three phase OTC drug review by the FDA. In phase I of the review, an advisory review panel determines whether ingredients in the proposed OTC composition could be generally recognized as safe and effective for use in self-treatment. In the second pathway, marketing occurs under the authority of an approved product-specific new drug application (NDA), or an abbreviated new drug application (ANDA). In order to support an over-the-counter label for a drug for which regulatory approval is being sought through an NDA, a consumer research study is required to assess the consumer's ability to select and deselect themselves as appropriate users of the drug, based on the proposed labeling for the drug. Oliver, A., Regulatory Rapporteur, 10(3):4-9 (2013), which is incorporated by reference herein.

However, attempts at switching distribution of cardiovascular drugs having potentially far-reaching benefits for societal health, from prescription-only to an OTC model, have repeatedly failed, in large part due to concerns over inappropriate patient selection and medication. Possibly the best documented cases relate to statins used to treat high cholesterol.

For instance, Merck has had at least three applications for sale of over the counter lovastatin rejected by the FDA, in 2000, 2005, and 2007. In 2005, their proposal to permit over the counter sales of lovastatin was rejected by an expert advisory panel at the FDA in 2005. The panel was concerned by a marketing study performed to support the proposal in which approximately one third of 3316 customers who were offered the drug over the counter decided they would purchase the drug. After reviewing the data, the panel concluded that 45% of the purchases would have been inappropriate for a variety of reasons, including the age of the subject, the subject's lack of knowledge about their condition, and contraindications associated with their condition. Dyer O., BMJ, 330(7484):164 (2005). In 2007, the board again concluded that the ability of consumers to appropriately self-select and to adequately comply with chronic MEVACOR® therapy without the intervention of a physician had not been demonstrated. Division of Metabolic and Endocrine Drug Products, 2005, "NDA 21-213 Non-prescription MEVACOR® 20 mg Joint Advisory Committee Meeting."

Similarly, Pfizer announced in 2011 its intention to switch LIPITOR® from prescription-only to OTC status. Sett OTC bulletin, 16 Nov. 2011, page 7. However, they abandoned their attempt in 2014 when a phase 3 "actual use" trial, intended to simulate the OTC use of LIPITOR® (atorvastatin calcium) 10 mg, failed to meet its primary objectives on the basis that patient compliance with the direction to check their low-density lipoprotein cholesterol (LDL-C) level and, after checking their LDL-C level, take appropriate action based on their test results was unsatisfactory. Pfizer Inc., "Pfizer Reports Second-Quarter 2015 Results," (2015).

In fact, in the nearly two decades since Bristol-Myers Squibb and Merck & Co first failed in their attempts to switch PRAVACHOL® and lovastatin, respectively, to OTC, a statin has never been granted OTC status in the United States. This is despite that nearly 40 million adults in the U.S. who are eligible for cholesterol-lowering medications, under the current guidelines, are not taking anything.

The information disclosed in this Background section is only for enhancement of understanding of the general background of the invention and should not be taken as an acknowledgment or any form of suggestion that this information forms the prior art already known to a person skilled in the art.

SUMMARY

Given the above background, what is needed in the art are systems and methods for qualifying a human subject for delivery of an angiotensin II receptor blocker pharmaceutical composition over-the-counter to lower blood pressure, e.g., thereby, treating or preventing heart disease.

The present disclosure addresses the need in the art for systems and methods configured for qualifying a human subject for over-the-counter delivery of an angiotensin II receptor blocker pharmaceutical composition (e.g., azilsartan medoxomil) in order to treat or prevent heart disease, e.g., by lowering blood pressure. In the present disclosure, systems and methods are provided for over-the-counter delivery of an angiotensin II receptor blocker pharmaceutical composition to a subject. Survey results from the subject are run against a first plurality of filters. When a filter in the first plurality is fired, the subject is deemed not qualified for delivery of the angiotensin II receptor blocker pharmaceutical composition. The survey results are also run against a second plurality of filters. When a respective filter in the second plurality is fired, the subject is provided with a corresponding warning. The method proceeds to a fulfillment process when no filter in the first plurality is fired and the subject has acknowledged each warning associated with each fired filter in the second plurality of filters. The fulfillment process stores the composition order, communicates a drug facts label for the angiotensin II receptor blocker pharmaceutical composition to the subject, and authorizes, upon subject confirmation that the label has been read, provision of the angiotensin II receptor blocker pharmaceutical composition to the subject.

Accordingly, one aspect of the present disclosure provides a method for qualifying a subject for over-the-counter delivery of an angiotensin II receptor blocker pharmaceutical composition in order to lower the blood pressure of the subject. The method includes conducting an assessment survey of the subject in order to obtain a variety of assessment survey results. In some embodiments, the assessment survey results include one or more of: whether the subject is pregnant, breastfeeding, or planning to become pregnant, whether the subject is taking a medication that interacts (e.g., a pharmacokinetic interaction and/or a pharmacodynamic interaction) with the angiotensin II receptor blocker pharmaceutical composition, a blood pressure of the subject (e.g., a systolic blood pressure of the subject and/or a diastolic blood pressure of the subject), an age of the subject, information required to calculate a risk of atherosclerotic cardiovascular disease for the subject, whether the subject has ever had an abnormal electrolyte blood level, and whether the subject has ever had a kidney problem.

The method also includes running all or a portion of the survey results against a first plurality of assessment filters of a first category class. When a respective filter in the first plurality of assessment filters is fired, the subject is deemed not qualified for delivery of the angiotensin II receptor blocker pharmaceutical composition. The method is then terminated accordingly without delivery of the angiotensin II receptor blocker pharmaceutical composition to the subject. In some embodiments, the first plurality of assessment filters includes one or more of a pregnancy assessment filter, a drug interaction assessment filter, a blood pressure assessment filter, an age assessment filter, and a pooled cohort equation assessment filter.

The method also includes running all or a portion of the survey results against a second plurality of assessment filters of a second category class. When a respective filter in the second plurality of assessment filters is fired, the subject is provided with a warning corresponding to the respective assessment filter. In some embodiments, the second plurality of assessment filters includes one or more of an electrolyte blood level assessment filter and a kidney problem assessment filter. However, unlike filters in the first plurality of assessment filters, filters in the second plurality of assessment filters do not automatically terminate the process without delivery of the angiotensin II receptor blocker pharmaceutical composition to the subject.

The method continues by obtaining acknowledgment from the subject for the warning issued to the subject by any filter in the second plurality of reassessment filters. In some embodiments, acknowledgment from the subject is a written acknowledgement, a verbal acknowledgment, or an electronic acknowledgment such as an electronic signature.

The method continues by proceeding with a fulfillment process when no filter in the first plurality of filters has been fired and the subject has acknowledged each warning associated with each filter in the second plurality of filters that was fired.

In some embodiments, the fulfillment process includes storing an indication in a subject profile of an initial order for the angiotensin II receptor blocker pharmaceutical composition, communicating an over-the-counter drug label for the angiotensin II receptor blocker pharmaceutical composition, and authorizing, upon confirmation from the subject that the over-the-counter drug label has been received and read, provision of the angiotensin II receptor blocker pharmaceutical composition to the subject.

In some embodiments, the angiotensin II receptor blocker pharmaceutical composition includes azilsartan or a pharmaceutically acceptable salt thereof (e.g., azilsartan medoxomil etc.) In some embodiments, the angiotensin II receptor blocker pharmaceutical composition includes azilsartan medoxomil. In some embodiments, the angiotensin II receptor blocker pharmaceutical composition includes candesartan, eprosartan, irbesartan, losartan, olmesartan, telmisartan, or valsartan.

In one aspect, the present disclosure provides a method for qualifying a subject for a re-order (e.g., a subject who was previously qualified to receive a provision of the angiotensin II receptor blocker pharmaceutical composition) of the angiotensin II receptor blocker pharmaceutical composition (e.g., which is optionally performed in conjunction with a method for qualifying the subject for a first order of the angiotensin II receptor blocker pharmaceutical composition). The method includes a re-fulfillment procedure. The re-fulfillment procedure includes conducting a reassessment survey of the subject in order to obtain a variety of reassessment survey results. In some embodiments, the reassessment survey results includes one or more of: a blood pressure of the subject (e.g., a systolic blood pressure of the subject and/or a diastolic blood pressure of the subject), whether the subject is one of pregnant, breastfeeding, or planning to become pregnant, whether the subject is taking a medication that interacts with the angiotensin II receptor blocker pharmaceutical composition, whether the subject has experienced symptoms of hypotension since receiving their last provision of the angiotensin II receptor blocker pharmaceutical composition, whether the subject has developed an abnormal electrolyte blood level since receiving their last provision of the angiotensin II receptor blocker pharmaceutical composition, and whether the subject has developed a kidney problem since receiving their last provision of the angiotensin II receptor blocker pharmaceutical composition.

The method also includes running all or a portion of the variety of reassessment survey results against a first plurality of reassessment filters of the first category class. When a respective filter in the first plurality of reassessment filters is fired, the subject is deemed not qualified for the angiotensin II receptor blocker pharmaceutical composition. Accordingly, the re-fulfillment process is terminated without delivery of the angiotensin II receptor pharmaceutical composition to the subject. In some embodiments, the first plurality of reassessment filters includes one or more of: a blood pressure reassessment filter, a pregnancy reassessment filter, a drug interaction reassessment filter, a hypotension reassessment filter, an electrolyte blood level reassessment filter, and a kidney problem reassessment filter.

In some embodiments, the re-fulfillment procedure includes storing an indication in the subject profile of a re-order for the angiotensin II receptor blocker pharmaceutical composition, communicating an over-the-counter drug facts label for the angiotensin II receptor blocker pharmaceutical composition to the subject, and authorizing, upon confirmation from the subject that the over-the-counter drug facts label has been received and read, a re-order provision of the angiotensin II receptor blocker pharmaceutical composition to the subject.

BRIEF DESCRIPTION OF THE DRAWINGS

FIGS. 4A, 4B, 4C, 4D, 4E, and 4F collectively provide a flow chart of processes for qualifying a human subject for over-the-counter delivery of an angiotensin II receptor blocker pharmaceutical composition to lower blood pressure, in accordance with various embodiments of the present disclosure.

FIGS. 5A, 5B, 5C, and 5D collectively provide a flow chart of processes for qualifying a subject for a refill of an over-the-counter delivery of an angiotensin II receptor blocker pharmaceutical composition to lower blood pressure, in accordance with various embodiments of the present disclosure.

FIGS. 6A, 6B, 6C, 6D, and 6E collectively illustrate a portion of an assessment survey of a subject for obtaining a first plurality of assessment survey results, in accordance with an embodiment of the present disclosure.

FIG. 7 illustrates feedback from a portion of an assessment survey, in accordance with an embodiment of the present disclosure.

Figure 1:
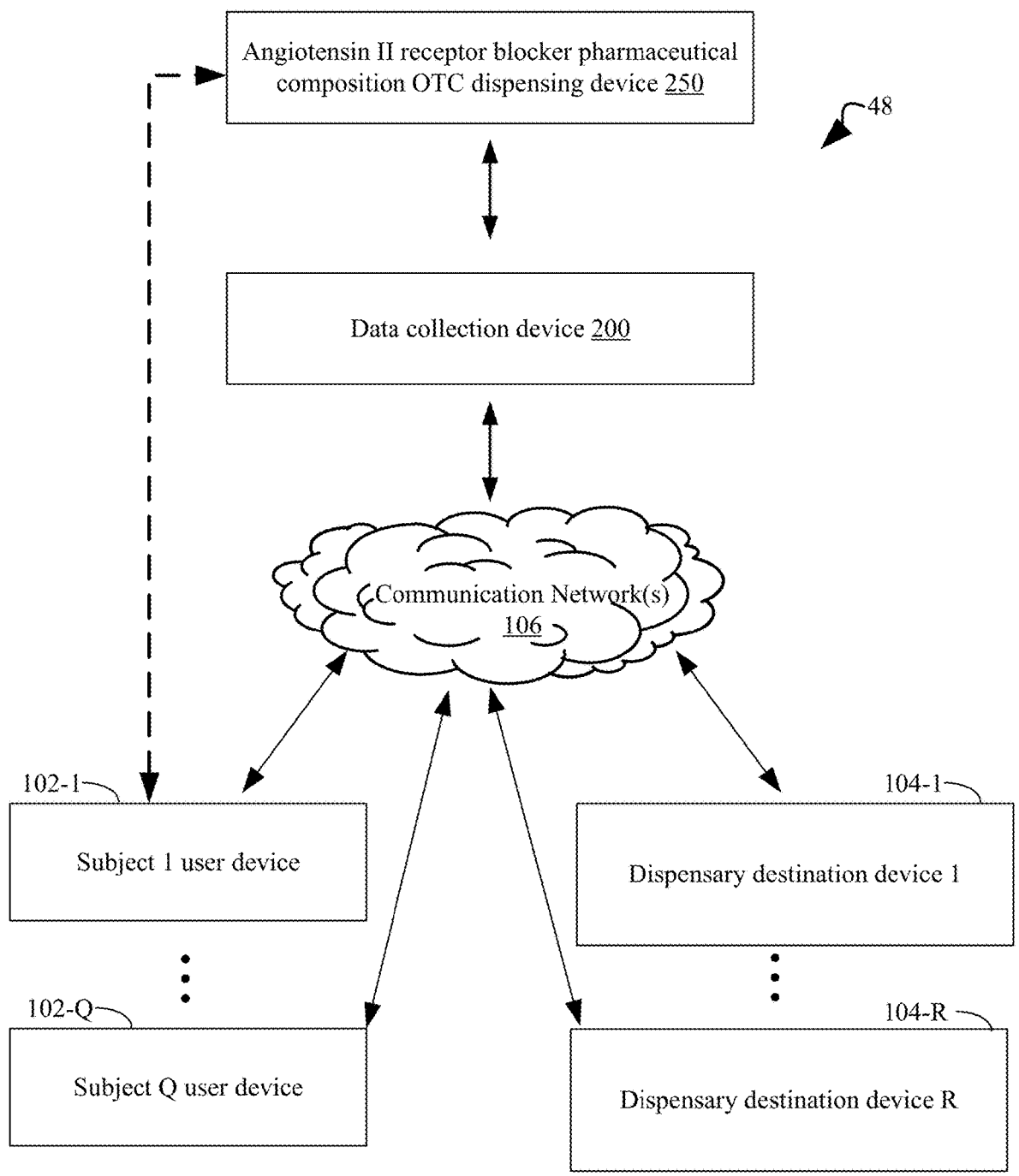
FIG. 1 illustrates an exemplary system topology that includes an angiotensin II receptor blocker pharmaceutical composition over-the-counter (OTC) dispensing device for qualifying a human subject for over-the-counter delivery of an angiotensin II receptor blocker pharmaceutical composition to lower blood pressure, a data collection device for collecting subject data, one or more user devices associated with human subjects, and one or more dispensary destinations for distributing the angiotensin II receptor blocker pharmaceutical composition over-the-counter, where the above-identified components are interconnected, optionally through a communications network, in accordance with an embodiment of the present disclosure.

In the figures, reference numbers refer to the same or equivalent parts of the present invention throughout the several figures of the drawing.

DETAILED DESCRIPTION

Hypertension is a growing health problem, in the United States and worldwide. Although hypertension can be effectively treated and/or prevented using established pharmaceutical compositions, access to these drugs is hindered by to the requirement for a prescription, as many individuals do not have adequate access and/or avoid the healthcare system for a variety of reasons. Accordingly, many people are not managing their hypertension or conditions related to hypertension appropriately. While over-the-counter alternatives to these prescription pharmaceuticals would increase access to these compositions, thereby improving population management of hypertension and conditions related to hypertension around the world, patients often have difficulty self-selecting themselves for an appropriate over-the-counter medication. Because inappropriate use of these drugs can result in ineffective treatment and/or serious side-effects, better methods for selecting for, and treating patients with, other-the-counter hypertension medications are needed. The present disclosure provides, among other aspects, methods, systems, and computer readable media that solve these problems.

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over-the-counter" means to provide by retail purchase, subject to the constraints disclosed herein, but without a prescription or license from a physician or medical practitioner.

As used herein, the term "pharmaceutical compound" refers to any physical state of a material. Pharmaceutical compounds include but are not limited to capsules, tablets, liquids, topical formulations, and inhaled formulations.

As used herein, the term "contraindication" refers to a condition that makes a treatment, e.g., over-the-counter use of an angiotensin II receptor blocker pharmaceutical composition, inadvisable. Contraindications include physical characteristics of a subject, e.g., pregnancy or kidney disease, and contemporaneous drug use, e.g., angiotensin II receptor blocker pharmaceutical composition use. In the present context, identification of a contraindication fires a filter of a first category class, which prevents authorizing provision of an angiotensin II receptor blocker pharmaceutical composition, in accordance with some implementations of the methods, systems, and software disclosed herein.

As used herein, the term "risk factor" refers to a condition that makes a treatment, e.g., over-the-counter use of an angiotensin II receptor blocker pharmaceutical composition, possibly inadvisable. Risk factors include physical characteristics of a subject, e.g., a blood pressure reading, and contemporaneous drug use, e.g., use of a blood pressure medication. In the present context, identification of a risk factor fires a filter of a second category class, which prevents authorizing provision of an angiotensin II receptor blocker pharmaceutical composition without confirmation that the subject has discussed the risk factor with a medical professional, in accordance with some implementations of the methods, systems, and software disclosed herein.

As used herein, "drug interactions," e.g., with an angiotensin II receptor blocker pharmaceutical composition, include pharmacokinetic drug interactions and pharmacodynamics drug interactions. Generally, a pharmacokinetic drug interaction is an interaction between two drugs (e.g., an angiotensin II receptor blocker and a second drug) that result in alterations in the absorption, transport, distribution, metabolism, and/or excretion of either drug. Generally, a pharmacokinetic drug interaction is an interaction between two drugs (e.g., an angiotensin II receptor blocker and a second drug) that result in a direct change in the effect or either drug. For a more comprehensive summary of pharmacokinetic drug interactions and pharmacodynamics drug interactions, see, Cascorbi, I, Dtsch Arztebl Int., 109(33-34):546-55 (2012), the content of which is hereby incorporated by reference.

In the context of the present disclosure, classification of a condition as either a contraindication or a risk factor is specific to a particular identity and dose of an angiotensin II receptor blocker pharmaceutical composition being authorized for over-the-counter use. Classification of a particular condition, e.g., contemporaneous angiotensin II receptor blocker pharmaceutical composition use, may vary between different angiotensin II receptor blocker pharmaceutical compositions (e.g., it may be classified as a contraindication for a first angiotensin II receptor blocker, a risk factor for a second angiotensin II receptor blocker, and/or neither for a third angiotensin II receptor blocker). Likewise, a particular condition may be classified as a contraindication for use of a particular angiotensin II receptor blocker at a first over-the-counter dosage, classified as a risk factor for the same particular angiotensin II receptor blocker at a second (e.g., lower) over-the-counter dosage, and/or classified as neither for the same particular angiotensin II receptor blocker at a third (e.g., lowest) over-the-counter dosage.

As used herein, whether a subject "has developed" and/or "has experienced" a condition since receiving their last provision of a angiotensin II receptor blocker refers to both conditions that are new to the subject, i.e., a condition that the subject did not have at the time they received their last provision of the angiotensin II receptor blocker, and conditions that have been newly diagnosed, regardless of whether the condition existed when the subject received their last provision of the angiotensin II receptor blocker, i.e., a condition that the subject was not aware of when they received their last provision of the angiotensin II receptor blocker.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (e.g. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Each of the above terms (e.g., "alkyl," "heteroalkyl," and "cycloalkyl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', —NR'R", —SR', halogen, —SiR'R"R'", —OC(O)R', —C(O)R', —CONR'R", —OC(O)NR'R", —NR"C(O)R', —NR'—C(O)NR"R'", —NR"C(O)$_2$R', —NR—C(NR'R"R'")=NR"", NR C(NR'R")=NR'", —S(O)R', —S(O)$_2$R', —S(O)$_2$NR'R", NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents," which are components of exemplary "substituted alkyl" and "substituted heteroalkyl" moieties.

As used herein, the term "heteroatom" includes oxygen (O), nitrogen (N), sulfur (S) and silicon (Si), boron (B) and phosphorous (P).

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

In one aspect of the present disclosure, a survey (e.g., an assessment survey and/or a reassessment survey) of a subject is conducted to obtain survey results in order to determine if the subject qualifies for an over-the-counter (OTC) angiotensin II receptor blocker (e.g., AGTR1, AGTR2)

pharmaceutical composition for lowering blood pressure, e.g., thereby, treating or preventing an atherosclerotic cardiovascular disease. The survey results are used as the basis for running filters of a first category class. If the triggering conditions of any of the filters in the first category class are fired, the subject does not qualify for the OTC angiotensin II receptor blocker pharmaceutical composition. In some embodiments, the survey results are also used as the basis for running filters of a second category class. If the triggering conditions of any of the filters in the second category class are fired, the subject is provided with warning messages associated with the respective filters of the second category class that have been fired. If none of the filters in the first category class are fired and the subject successfully addresses the warning messages associated with the respective filters of the second category class that have been fired a fulfillment process is initiated for OTC delivery of the angiotensin II receptor blocker pharmaceutical composition.

FIG. 1 illustrates an example of an integrated system 48 for conducting one or more surveys (e.g., an assessment survey and/or a reassessment survey) of one or more subjects in order to qualifying the subjects for OTC delivery of an angiotensin II receptor blocker pharmaceutical composition. The integrated system 48 includes one or more connected user devices 102 (e.g., first user device 102-1, second user device 102-2, . . . , $Q^{th}$ user device 102-Q). The user devices 102 are configured for entering survey data and making requests for the angiotensin II receptor blocker pharmaceutical composition. The system 48 also includes one or more dispensary destination devices 104 that is configured to receive instructions in order to provide the angiotensin II receptor blocker pharmaceutical composition to qualifying subjects. Furthermore, the system 48 includes an angiotensin II receptor blocker pharmaceutical composition over-the-counter (OTC) dispensing device 250 and one or more data collection devices 200 that are configured for collecting subject data.

Throughout the present disclosure, the data collection device 200 and the angiotensin II receptor blocker pharmaceutical composition OTC dispensing device 250 will be referenced as separate devices solely for purposes of clarity. That is, the disclosed functionality of the data collection device 200 and the disclosed functionality of the angiotensin II receptor blocker pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the angiotensin II receptor blocker pharmaceutical composition OTC dispensing device 250 are contained in a single device.

With the integrated system 48, survey results from the subjects are run against a first plurality of filters, such as a first plurality of assessment filters (e.g., filter 216-1, filter 216-2, filter 216-4, etc.) and/or a first plurality of reassessment filters (e.g., filter 216-6, filter 216-7, etc.). When a filter in the first respective plurality of filters (e.g., filter 216) is fired for a respective subject, the respective subject is deemed not qualified for the angiotensin II receptor blocker pharmaceutical composition. In some embodiments, the survey results are also run against a second plurality of filters (e.g., filter 222-1, filter 222-2, filter 222-6, etc.) When a respective filter in the second respective plurality is fired for a respective subject, the respective subject is provided with a warning (e.g., filter warning 226) associated with the respective filter. In some embodiments, the survey results are run against the first plurality of filters and the second plurality of filters concurrently. In some embodiments, the survey results are run against the first plurality of filters and then against the second plurality of filters. For instance, in some embodiments the survey results are obtained and then run against the plurality of filters. However, the present disclosure is not limited thereto. In some embodiments, each survey result is run against a corresponding filter prior to a subsequent survey result being obtained, thereby preventing a user from unnecessarily providing survey results in accordance with a determination that the user is not qualified for the angiotensin II receptor blocker pharmaceutical composition.

As used herein, unless expressly stated otherwise, a survey refers to both an assessment survey and/or a reassessment survey. For instance, in some embodiments a first survey result corresponds to an assessment survey, whereas in other embodiments a first survey results corresponds to a reassessment survey, without departing from the scope of the present disclosure.

The method enabled by the integrated system 48 proceeds to a fulfillment process, or similarly a refulfillment process, when no filter in the first respective plurality of filters fires and the subject has acknowledged, or otherwise successfully addressed, each warning associated with each filter in the second respective plurality of filters that fired. As part of the fulfillment process, or refulfillment process, the composition order is stored (e.g., in a user profile 234 associated with the subject to receive the drug), a drug facts label (e.g., drug facts label 230) for the angiotensin II receptor blocker is communicated to the qualifying subject. Upon subject confirmation that the label has been read, authorization is granted to dispense the angiotensin II receptor blocker.

Referring to FIG. 1, the angiotensin II receptor blocker pharmaceutical composition OTC dispensing device 250 qualifies a subject for over-the-counter delivery of an angiotensin II receptor blocker pharmaceutical composition to lower blood pressure. To accomplish the above, the data collection device 200, which is in electrical communication with the angiotensin II receptor blocker pharmaceutical composition OTC dispensing device 250, receives survey results (e.g., assessment survey results and/or reassessment survey results) originating from one or more user devices 102 that are associated with corresponding subjects. In some embodiments, the data collection device 200 receives such survey results directly from the user devices 102. For instance, in some embodiments the data collection device 200 receives this data wirelessly through radio-frequency (RF) signals. In some embodiments, such signals are in accordance with an 802.11 (Wi-Fi), Bluetooth, or ZigBee standard. In some embodiments, the data collection device 200 receives such data directly, analyzes the data, and passes the analyzed data to the angiotensin II receptor blocker pharmaceutical composition OTC dispensing device 250.

In some embodiments, the data collection device 200 and/or the angiotensin II receptor blocker pharmaceutical composition OTC dispensing device 250 is not proximate to the subject and/or does not have wireless capabilities or such wireless capabilities are not used for the purpose of acquiring survey results. In such embodiments, a communication network 106 may be used to survey questions (e.g., survey questions 208, 212) from the angiotensin II receptor blocker pharmaceutical composition OTC dispensing device 250 to user devices 102 and the answers to such survey questions from the user devices 102 to the data collection device 200 and/or the angiotensin II receptor blocker pharmaceutical composition OTC dispensing device 250. Further, in some embodiments the communication network 106 is used to communicate authorization to dispense the angiotensin II receptor blocker survey questions from the angiotensin II receptor blocker pharmaceutical composition OTC dispensing device 250 to dispensary destination devices 104.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoW), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the angiotensin II receptor blocker pharmaceutical composition OTC dispensing device 250. Further, the data collection device 200 and/or the angiotensin II receptor blocker pharmaceutical composition OTC dispensing device 250 may constitute a portable electronic device, a server computer, or in fact constitute several computers that are linked together in a network, be a virtual machine in a cloud computing context, be a container in a cloud computer context, or a combination thereof. As such, the exemplary topology shown in FIG. 1 merely serves to describe the features of an embodiment of the present disclosure in a manner that will be readily understood to one of skill in the art.

Figure 2:
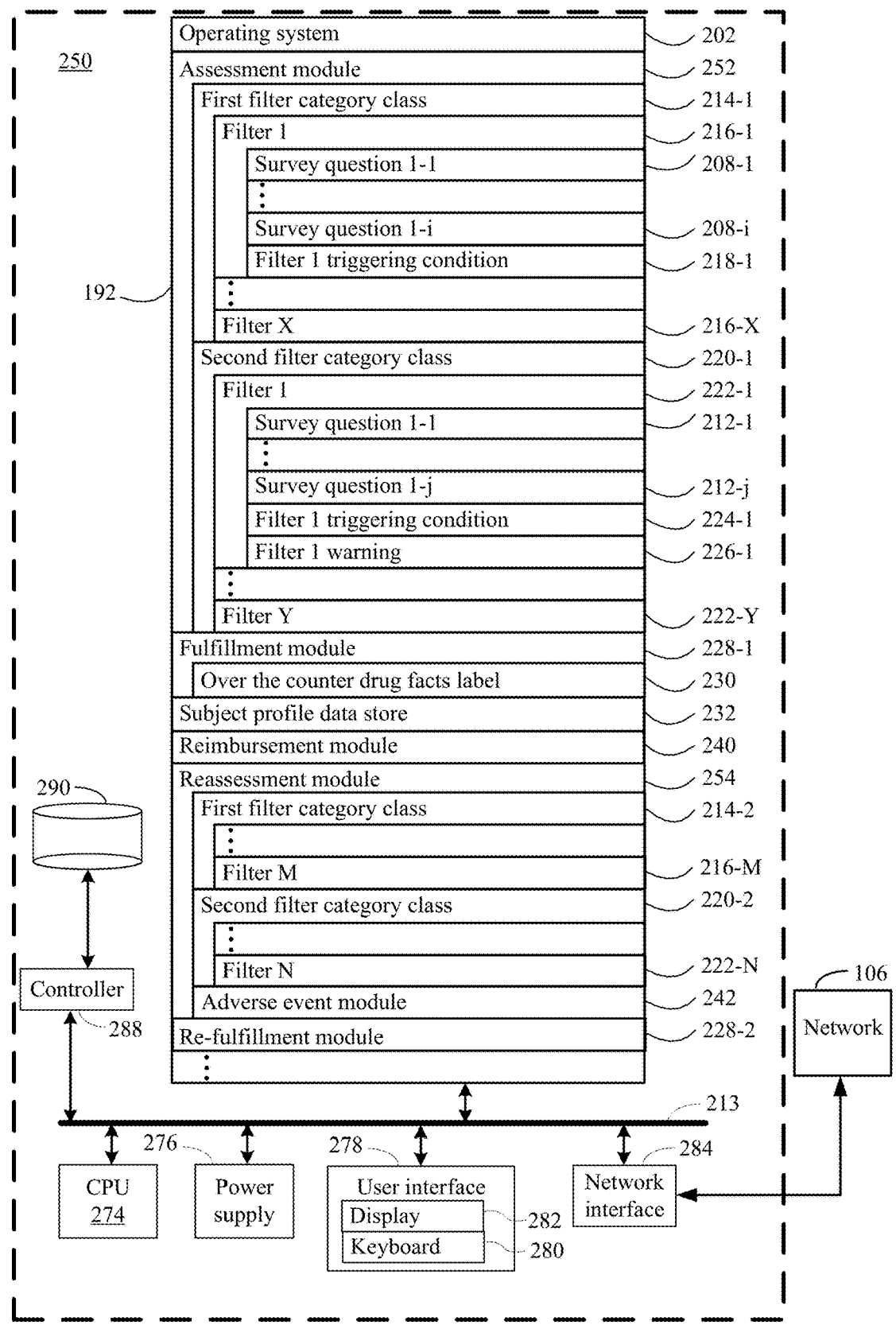
FIG. 2 illustrates an example device for qualifying a human subject for delivery of an angiotensin II receptor blocker pharmaceutical composition over-the-counter to lower blood pressure in accordance with various embodiments of the present disclosure.

Turning to FIG. 2 with the foregoing in mind, an exemplary angiotensin II receptor blocker pharmaceutical composition OTC dispensing device 250 configured for determining whether a subject is qualified for OTC delivery of an angiotensin II receptor blocker is depicted. Referring to FIG. 2, in typical embodiments, the angiotensin II receptor blocker pharmaceutical composition OTC dispensing device 250 includes one or more computers. For purposes of illustration in FIG. 2, the angiotensin II receptor blocker pharmaceutical composition OTC dispensing device 250 is represented as a single computer that includes all of the functionality for qualifying a human subject for over-the-counter delivery of an angiotensin II receptor blocker pharmaceutical composition to lower blood pressure. However, the present disclosure is not limited thereto. In some embodiments, the functionality for qualifying a human subject for over-the-counter delivery of an angiotensin II receptor blocker pharmaceutical composition to lower blood pressure is spread across any number of networked computers and/or resides on each of several networked computers, is hosted on one or more virtual machines at a remote location accessible across the communications network 106, and/or is hosted on one or more containers at a remote location accessible across the communications network 106. One of skill in the art will appreciate that any of a wide array of different computer topologies are used for the present disclosure and all such topologies are within the scope of the present disclosure.

The angiotensin II receptor blocker pharmaceutical composition OTC dispensing device 250 of FIG. 2 is configured to conduct an assessment survey (e.g., using assessment module 252 to perform an initial qualification of the subject for provision of a angiotensin II receptor blocker pharmaceutical composition) and/or a reassessment survey (e.g., using reassessment module 254 to perform a re-qualification of the subject for provision of a angiotensin II receptor blocker pharmaceutical composition). The assessment survey (e.g., the assessment) includes a variety of questions 208, 212 associated with assessment filters 216, 222 within a first plurality of assessment filters of the first filter category class 214 and a second plurality of assessment filters in the second filter category class 220, respectively. Answers to the questions in the assessment survey received by the device 250 are run against one or more assessment filters of a first category class 216-1 and/or, in some embodiments, one or more assessment filters of a second category class 220-1 within the first and second pluralities of assessment filters 214-1 and 216-1, respectively. Similarly, the reassessment survey (e.g., the re-assessment) also includes a variety of questions 208, 212 associated with reassessment filters 216, 222 within a first plurality of reassessment filters of a first category class 214-2 and/or, in some embodiments, a second plurality of reassessment filters of a second category class 220-2, respectively. Answers to the questions in the reassessment survey received by the device 250 are run against one or more reassessment filters of a first category class 216-2 and reassessment filters of a second category class 220-2, e.g., within the first and second pluralities of reassessment filters, respectively. Reassessment filters 216 of the first filter category class 214 are configured to terminate the qualification process when fired. Reassessment filters 222 of the second filter category class 220 are configured to provide the subject with a warning associated with a corresponding survey question. In other words, the device of FIG. 2 is configured to accumulate results from a survey (e.g., survey questions 208 and survey questions 212 of an assessment survey module 252 and/or a reassessment survey module 545) and run the results against corresponding filters (e.g., assessment filters and/or reassessment filters, respectively) in order to determine if a subject is qualified for OTC delivery of an angiotensin II receptor blocker pharmaceutical composition.

In the present disclosure, a plurality of filters refers to a series, or set, or filters in either the first filter category class or the second category class. For instance, in some embodiments, a plurality of filters of the first filter category class 214 can include any subset of filters 216 of the first filter category class. As an example, in some embodiments a plurality of filters of the first category class includes filters 216-1, 216-2, 216-3, . . . , 216-i, or any combination thereof. Similarly, a plurality of filters of the second filter category class 220 can include any set of filters 222 of the second filter category class. Moreover, in some embodiments a plurality of filters of the second category class includes filters 222-1, 222-2, 222-3, . . . , 222-i, or any combination thereof. However, the present disclosure is not limited thereto. For instance, in some embodiments filters of the first category class are categorized according to which survey the filter is associated with (e.g., filters of the first category class are categorized by assessment filters and/or reassessment filters, filters of the second category class are categorized by assessment filters and/or reassessment filters).

Continuing to refer to FIG. 2, in some embodiments, the dispensing device 250 includes one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., a keyboard, a keypad, a touch screen, etc.), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the angiotensin II receptor blocker pharmaceutical composition OTC dispensing device 250 but that can be electronically accessed by the angiotensin II receptor blocker pharmaceutical composition OTC dispensing device 250 over an Internet, intranet, or other form of network or electronic cable (illustrated as element 106 in FIG. 2) using network interface 284.

In some embodiments, the memory 192 of the angiotensin II receptor blocker pharmaceutical composition OTC dispensing device 250 stores one or more of:

an operating system 202 that includes procedures for handling various basic system services;

an assessment module 252 for qualifying a subject for an initial over-the-counter delivery of an angiotensin II receptor blocker pharmaceutical composition to lower blood pressure, e.g., treating or preventing heart disease, by communicating assessment survey questions, obtaining results therefrom, and applying the results to qualifying assessment filters, the assessment module including:

a first filter category class 214-1, including assessment filters 216 (e.g., a first plurality of assessment filters), each respective assessment filter 216 in the first filter category class 214-1 associated with one or more assessment survey questions 208 and one or more triggering conditions 218;

a second filter category class 220-1, including assessment filters 222 (e.g., a second plurality of assessment filters), each respective assessment filter 222 in the second filter category class 220-1 associated with one or more assessment survey questions 208, triggering conditions 224, and warnings 226;

a fulfillment module 228-1 for executing a fulfillment process when no assessment filter 216 in the first filter category class 214-1 has been fired for a subject and the subject has acknowledged each warning 226 associated with each assessment filter 222 in the second filter category class 220-1 that was fired as a result of answers by the subject to the assessment survey questions 208, where the fulfillment process includes communicating an over-the-counter drug facts label 230 for the angiotensin II receptor blocker pharmaceutical composition to the subject and receiving confirmation from the subject that the over-the-counter drug facts label has been received and read;

a reassessment module 254 for qualifying a subject for a subsequent over-the-counter delivery of an angiotensin II receptor blocker pharmaceutical composition to lower blood pressure, e.g., treating or preventing heart disease, by communicating reassessment survey questions, obtaining results therefrom, and applying the results to qualifying reassessment filters, the reassessment module including:

a first filter category class 214-2, including reassessment filters 216 (e.g., a first plurality of reassessment filters), each respective reassessment filter 216 in the first filter category class 214-2 is associated with one or more reassessment survey questions 208 and one or more triggering conditions 218;

a second filter category class 220-2, including reassessment filters 222 (e.g., a second plurality of filters), each respective filter 222 in the second filter category class 220-2 is associated with one or more survey questions 212, triggering conditions 224, and warnings 226;

a re-fulfillment module 228-2 for executing a re-fulfillment process when no reassessment filter 216 in the first filter category class 214-2 has been fired for a subject and the subject has acknowledged each warning 226 associated with each reassessment filter 222-2 in the second filter category class 220 that was fired as a result of answers by the subject to the reassessment survey questions 212, where the re-fulfillment process includes communicating an over-the-counter drug facts label 230 for the angiotensin II receptor blocker pharmaceutical composition to the subject and receiving confirmation from the subject that the over-the-counter drug facts label has been received and read;

a subject profile data store 232 comprising a user profile 234 for each of a plurality of subjects, each respective user profile 234 including information (e.g., shipping information, billing information, biometric information, etc.) about a corresponding subject in the plurality of subjects, an initial order date and/or destination 236, and any re-order date and/or the destination 238 for the angiotensin II receptor blocker pharmaceutical composition made by the corresponding subject using the angiotensin II receptor blocker pharmaceutical composition OTC dispensing device 250;

an adverse event module 242 for identifying and aggregating records of adverse events associated with a plurality of subjects, e.g., corresponding to the firing of a reassessment filter 216 in the first filter category class 214-2 during a re-fulfillment process;

a reimbursement module 240 for determining eligibility and/or communicating an insurance claim associated with delivery of the angiotensin II receptor blocker, e.g., based on insurance information stored in a respective user profile 234.

In some embodiments, the assessment module 252, the reassessment module 254, and/or the fulfillment module 228 is accessible within any browser (e.g., phone, tablet, laptop/desktop, or smartwatch). In some embodiments, the assessment module 252, reassessment module 254, and/or fulfillment module 228 run on native device frameworks, and is available for download onto a user device 102 running an operating system 202 such as Android, iOS, or WINDOWS.

In some implementations, one or more of the above identified data elements or modules (e.g., assessment module 252, fulfillment module 228-1, etc.) of the angiotensin II receptor blocker pharmaceutical composition OTC dispensing device 250 for qualifying a human subject for over-the-counter delivery of an angiotensin II receptor blocker pharmaceutical composition to lower blood pressure are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, an angiotensin II receptor blocker pharmaceutical composition OTC dispensing device 250 for qualifying a human subject for over-the-counter delivery of an angiotensin II receptor blocker pharmaceutical composition to lower blood pressure is a smart phone (e.g., an iPhone, Blackberry, etc.), a laptop, a tablet computer, a desktop computer, a smart watch, or another form of electronic device (e.g., a gaming console, a kiosk, a virtual reality system, etc.). In some embodiments, the angiotensin II receptor blocker pharmaceutical composition OTC dispensing device 250 is not mobile. In some embodiments, the angiotensin II receptor blocker pharmaceutical composition OTC dispensing device 250 is mobile.

In some embodiments, the angiotensin II receptor blocker pharmaceutical composition OTC dispensing device 250 is not a smart phone but rather is a tablet computer, desktop computer, emergency vehicle computer, or other form or wired or wireless networked device. In the interest of brevity and clarity, only a few of the possible components of the angiotensin II receptor blocker pharmaceutical composition OTC dispensing device 250 are shown in FIG. 2 in order to better emphasize the additional software modules that are installed on the angiotensin II receptor blocker pharmaceutical composition OTC dispensing device 250.

Figure 3A:
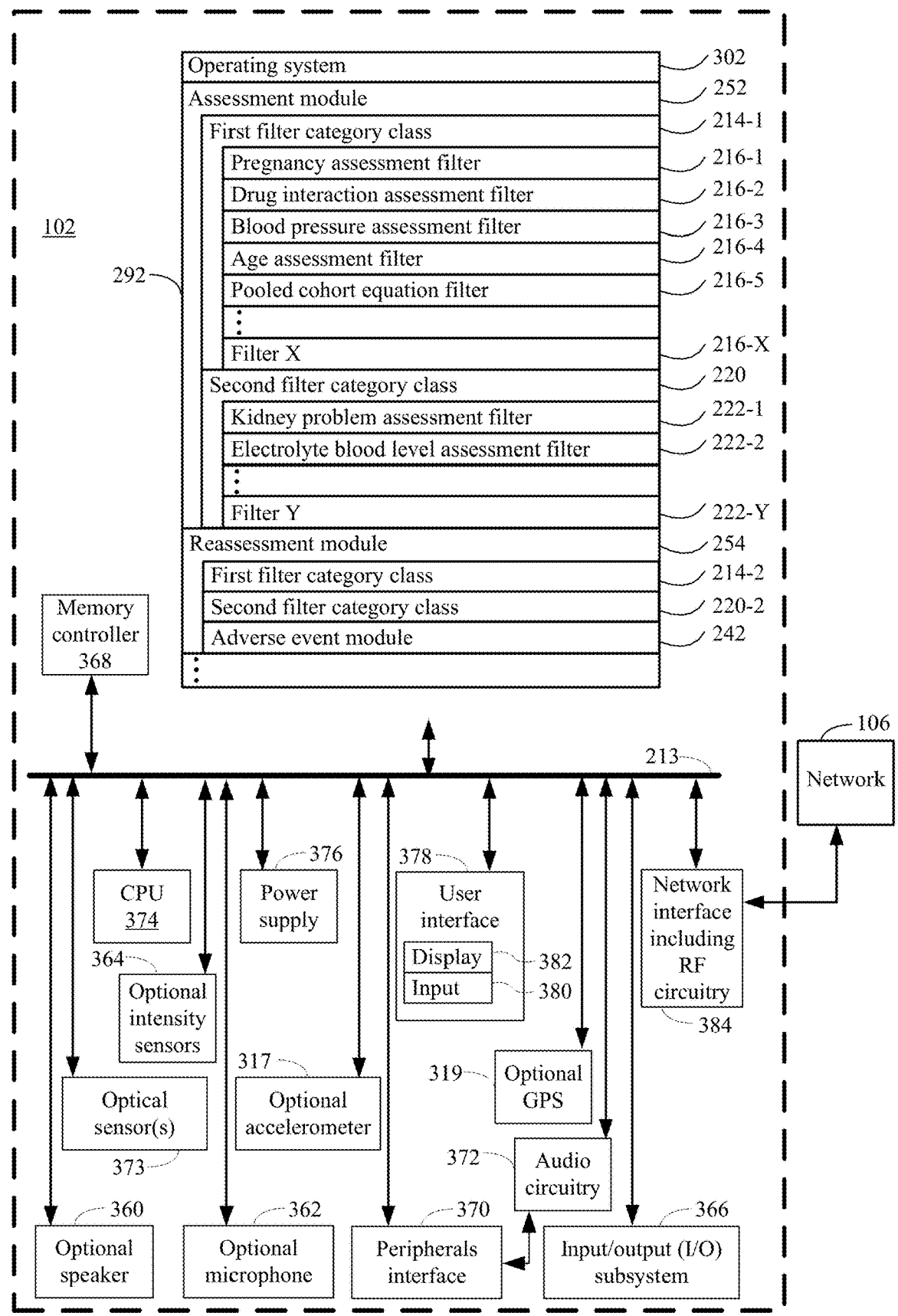
FIGS. 3A and 3B collectively illustrate an example device associated with a human subject for qualifying the human subject for over-the-counter delivery of an angiotensin II receptor blocker pharmaceutical composition for lowering blood pressure, e.g., thereby treating and/or preventing heart disease, in accordance with an embodiment of the present disclosure, where it will be appreciated that the example device of FIG. 3 works in conjunction with the device of FIG. 2 to perform the methods illustrated in FIGS. 4, 5, 8, and 9 in some embodiments by, for instance, providing the device of FIG. 2 with survey results and/or the results of firing filters of the present disclosure against such survey results but that, in alternative embodiments, the device of FIG. 2 performs all the methods of the present disclosure and the device of FIG. 3 is not used. In still further alternative embodiments, the device of FIG. 3 performs the methods of the present disclosure and the device of FIG. 2 is not used.
Figure 3B:
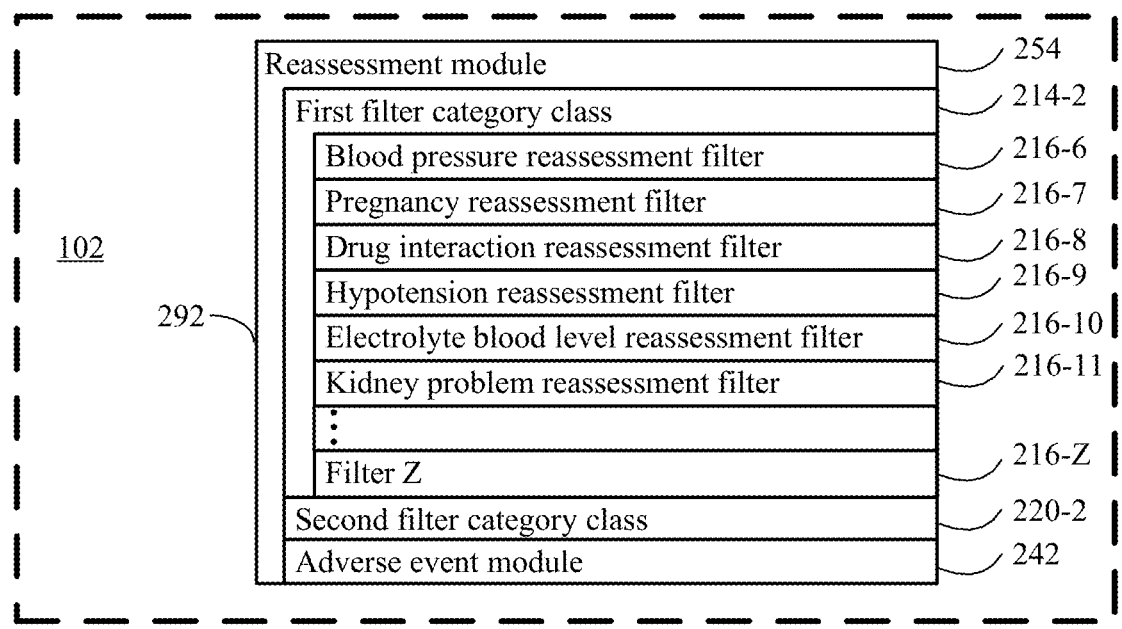

FIG. 3 provides a description of a user device 102 that can be used with the present disclosure. The user device 102 illustrated in FIG. 3 has one or more processing units (CPU's) 374, peripherals interface 370, memory controller 368, a network or other communications interface 384, a memory 392 (e.g., random access memory), a user interface 378, the user interface 378 including a display 382 and input 380 (e.g., a keyboard, a keypad, a touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 382 of the user device 102), an optional input/output (I/O) subsystem 366, one or more optional optical sensors 373, one or more communication busses 313 for interconnecting the aforementioned components, and a power supply 376 for powering the aforementioned components.

In some embodiments, the input 380 is a touch-sensitive display, such as a touch-sensitive surface. In some embodiments, the user interface 378 includes one or more soft keyboard embodiments. The soft keyboard embodiments may include standard (e.g., QWERTY) and/or non-standard configurations of symbols on the displayed icons.

The user device 102 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the user device 102 and/or for determining an amount of physical exertion by the subject.

It should be appreciated that the user device 102 illustrated in FIG. 3 is only one example of a multifunction device that may be used for performing a survey (e.g., assessment module 252) in order to qualify for over-the-counter delivery of a angiotensin II receptor blocker pharmaceutical composition to lower blood pressure, and that the user device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 392 of the user device 102 illustrated in FIG. 3 optionally includes high-speed random access memory and optionally also includes non-volatile memory, such as one or more magnetic disk storage devices, flash memory devices, or other non-volatile solid-state memory devices. Access to memory 392 by other components of the angiotensin II receptor blocker pharmaceutical composition OTC dispensing device 250, such as CPU(s) 374 is, optionally, controlled by the memory controller 368. In some embodiments, the memory 392 of the user device 102 illustrated in FIG. 3 optionally includes:

an operating system 302 that includes procedures for handling various basic system services;

the assessment module 252 described above in conjunction with the angiotensin II receptor blocker pharmaceutical composition OTC dispensing device 250;

the first category class 214 described above in conjunction with the angiotensin II receptor blocker pharmaceutical composition OTC dispensing device 250 further comprising a pregnancy assessment filter 216-1, a drug interaction assessment filter 216-2, a blood pressure assessment filter 216-3, an age assessment filter 216-4, and a pooled cohort equation assessment filter 216-5; and the second category class 220 described above in conjunction with the angiotensin II receptor blocker pharmaceutical composition OTC dispensing device 250 comprising an electrolyte blood level assessment filter 222-1, and a kidney problem assessment filter 222-2;

In some embodiments, the optional accelerometer 317, optional GPS 319, and/or magnetometer (not shown) of the user device 102 or such components are used to recommend to qualifying subjects one or more suitable destinations for delivery of the angiotensin II receptor blocker pharmaceutical composition over-the-counter. In some embodiments, the GPS 319 is used to determine if a subject is geographically restricted for OTC delivery of the angiotensin II receptor pharmaceutical composition. Geographical restrictions include but are not limited to a subject residing outside of delivery or shipping regions, marketing restrictions, and/or government regulations.

The peripherals interface 370 can be used to couple input and output peripherals of the device to CPU(s) 374 and memory 392. The one or more processors 374 run or execute various software programs and/or sets of instructions stored in memory 392, such as the survey module 204, to perform various functions for the user device 102 and to process data.

In some embodiments, the peripherals interface 370, CPU(s) 374, and memory controller 368 are, optionally, implemented on a single chip. In some other embodiments, they are implemented on separate chips.

RF (radio frequency) circuitry of network interface 384 receives and sends RF signals, also called electromagnetic signals. In some embodiments, the survey module 252/254, survey questions 208/212, answers to survey questions 208/212, and/or the over-the-counter drug facts label 230 are communicated to the subject device 102 using this RF circuitry. In some embodiments, the RF circuitry 384 converts electrical signals to/from electromagnetic signals and communicates with communications networks and other communications devices and/or the data collection device 200 and/or the angiotensin II receptor blocker pharmaceutical composition OTC dispensing device 250 via the electromagnetic signals. The RF circuitry 384 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 384 optionally communicates with the communication network 106. In some embodiments, the circuitry 384 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. In some embodiments, the speaker 360 converts the electrical signals to human-inaudible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 392 and/or the RF circuitry 384 by the peripherals interface 370.

In some embodiments, the power supply 376 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 382 on the front of the user device 102, so that the input 380 is enabled for use as a viewfinder for still and/or video image acquisition. In some embodiments, another optical sensor 373 is located on the front of the user device 102 so that the subject's image is obtained (e.g., to verify the health, condition, or identity of the subject as part of qualifying the subject for over-the-counter delivery of an angiotensin II receptor blocker pharmaceutical composition to lower blood pressure), to help diagnose a subject's condition remotely, or to acquire visual physiological measurements of the subject, etc.)

As illustrated in FIG. 3, the user device 102 preferably includes an operating system 302 that includes procedures for handling various basic system services. The operating system 302 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments, the user device 102 is a smart phone or a smart watch. In other embodiments, the user device 102 is not a smart phone or a smart watch but rather is a tablet computer, a desktop computer, an emergency vehicle computer, or other form or wired or wireless networked device. In the interest of brevity and clarity, only a few of the possible components of the user device 102 are shown in FIG. 3 in order to better emphasize the additional software modules that are installed on the user device 102.

While the system 48 disclosed in FIG. 1 can work standalone, in some embodiments it can also be linked with an electronic medical records system to exchange information in any way.

Now that details of a system 48 for qualifying a human subject for over-the-counter delivery of an angiotensin II receptor blocker pharmaceutical composition to lower blood pressure have been disclosed, details regarding methods (e.g., an assessment method 400 of FIG. 4 and/or a reassessment method 500 of FIG. 5), including processes and features to be performed by the system, in accordance with an embodiment of the present disclosure, are disclosed with reference to FIGS. 4 and 5, respectively. In some embodiments, such processes and features of the system 48 are carried out by the assessment module 252, reassessment module 254, fulfillment module 228-1, and/or re-fulfillment module 228-2 illustrated in FIGS. 2 and 3. In some embodiments, the assessment module 252, reassessment module 254, fulfillment module 228-1, and/or re-fulfillment module 228-1 are a single software module.

FIG. 4 illustrates method 400 for qualifying (402) a human subject for over-the-counter delivery of an angiotensin II receptor blocker pharmaceutical composition for lowering blood pressure, e.g., thereby, treating and/or preventing heart disease, using a computer system such as an angiotensin II receptor blocker pharmaceutical composition OTC dispensing device 250. As illustrated in FIG. 2, the angiotensin II receptor blocker pharmaceutical composition OTC dispensing device (e.g., device 250) includes one or more processors (e.g., processor 274) and a memory (e.g., memory 192 and/or 290). The memory stores non-transitory instructions that, when executed by the one or more processors, perform a method.

Referring to block 404 of FIG. 4A, in some embodiments the angiotensin II receptor blocker pharmaceutical composition has a structure of structure (I):

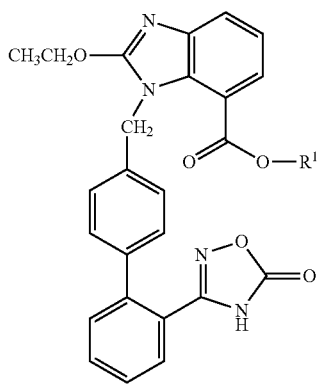

Accordingly, R¹ is a group represented by the formula:

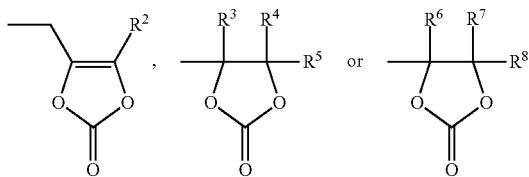

Moreover, $R^2$, $R^3$, $R^4$, $R^5$, $R^6$, $R^7$, and $R^8$ are each independently a hydrogen atom or a C1-6 alkyl, or a salt thereof.

Referring to blocks 406 through 410 of FIG. 4A, in some embodiments the angiotensin II receptor blocker pharmaceutical composition includes an active ingredient that is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate, or a pharmaceutically acceptable salt thereof.

In some embodiments, the angiotensin II receptor blocker pharmaceutical composition includes an active ingredient that is azilsartan, or a pharmaceutically acceptable prodrug thereof. In some embodiments, the active ingredient is azilsartan medoxomil, or a pharmaceutically acceptable salt thereof.

In some embodiments, the angiotensin II receptor blocker pharmaceutical composition includes one or more active ingredient selected from candesartan, eprosartan, irbesartan, losartan, olmesartan, telmisartan, valsartan, or a pharmaceutically acceptable salt thereof. In some embodiments, the angiotensin II receptor blocker pharmaceutical composition is a prodrug. As used herein, a prodrug refers to a pharmaceutical composition that includes a biologically inactive compound that is metabolized in vivo to generate the active form of the drug. For instance, in some embodiments the prodrug angiotensin II receptor blocker pharmaceutical composition includes azilsartan, candesartan, losartan, or olmesartan. Additional information regarding these angiotensin II receptor blocker active ingredients is described in Farnham et al., 2000, "Angiotensin II receptor antagonists," The Lancet, 335(9204), pg. 594, the content of which is hereby incorporated by reference, in its entirety, for all purposes.

In some embodiments, the angiotensin II receptor blocker pharmaceutical composition includes any compound disclosed in U.S. Pat. No. 7,572,920, entitled "Benzimidazole derivative and use as a II receptor antagonist," as an active ingredient. In some embodiments, the angiotensin II receptor blocker pharmaceutical composition includes any compound disclosed in U.S. Pat. No. 7,157,584, entitled "Benzimidazole derivative and use thereof," as an active ingredient.

In some embodiments, the angiotensin II receptor blocker pharmaceutical composition includes any compound disclosed in U.S. Pat. No. 5,656,560, entitled "Angiotensin II receptor blocking compositions," as an active ingredient. In some embodiments, the angiotensin II receptor blocker pharmaceutical composition includes any compound disclosed in U.S. Pat. No. 5,185,351, entitled "Imidazolylalkenoic acids useful as angiotensin II receptor antagonists," as an active ingredient.

In some embodiments, the angiotensin II receptor blocker pharmaceutical composition includes any compound disclosed in U.S. Pat. No. 5,270,317, entitled "N-substituted heterocyclic derivatives, their preparation and the pharmaceutical compositions in which they are present," as an active ingredient. In some embodiments, the angiotensin II receptor blocker pharmaceutical composition includes any compound disclosed in U.S. Pat. No. 5,994,348, entitled "Pharmaceutical compositions containing irbesartan," as an active ingredient. In some embodiments, the angiotensin II receptor blocker pharmaceutical composition includes any compound disclosed in U.S. Pat. No. 6,342,247, entitled "Pharmaceutical compositions containing irbesartan," as an active ingredient.

In some embodiments, the angiotensin II receptor blocker pharmaceutical composition includes any compound disclosed in U.S. Pat. No. 5,210,079, entitled "Treatment of chronic renal failure with imidazole angiotensin-II receptor antagonists," as an active ingredient. In some embodiments, the angiotensin II receptor blocker pharmaceutical composition includes any compound disclosed in U.S. Pat. No. 5,608,075, entitled "Polymorphs of losartan and the process for the preparation of form II of losartan," as an active ingredient.

In some embodiments, the angiotensin II receptor blocker pharmaceutical composition includes any compound disclosed in U.S. Pat. No. 5,616,599, entitled "Angiotensin II antagonist 1-biphenylmethylimidazole compounds and their therapeutic use," as an active ingredient. In some embodiments, the angiotensin II receptor blocker pharmaceutical composition includes any compound disclosed in U.S. Pat. No. 6,878,703, entitled "Pharmaceutical composition," as an active ingredient.

In some embodiments, the angiotensin II receptor blocker pharmaceutical composition includes any compound disclosed in U.S. Pat. No. 5,591,762, entitled "Benzimidazoles useful as angiotensin-II antagonists," as an active ingredient. In some embodiments, the angiotensin II receptor blocker pharmaceutical composition includes any compound disclosed in U.S. Pat. No. 6,358,986, entitled "Polymorphs of telmisartan," as an active ingredient. In some embodiments, the angiotensin II receptor blocker pharmaceutical composition includes any compound disclosed in U.S. Pat. No. 7,998,953, entitled "Use of inhibitors of the renin-angiotensin system," as an active ingredient.

In some embodiments, the angiotensin II receptor blocker pharmaceutical composition includes any compound disclosed in U.S. Pat. No. 5,399,578, entitled "Acyl compounds," as an active ingredient. In some embodiments, the angiotensin II receptor blocker pharmaceutical composition includes any compound disclosed in U.S. Pat. No. 5,559,111, entitled "δ-amino-γ-hydroxy-ω-aryl-alkanoic acid amides," as an active ingredient. In some embodiments, the angiotensin II receptor blocker pharmaceutical composition includes any compound disclosed in U.S. Pat. No. 5,972, 990, entitled "Methods for reducing risk of repeat myocardial infarction and increasing survival in heart attack victims," as an active ingredient. In some embodiments, the angiotensin II receptor blocker pharmaceutical composition includes any compound disclosed in U.S. Pat. No. 6,294,197, entitled "Solid oral dosage forms of valsartan," as an active ingredient. In some embodiments, the angiotensin II receptor blocker pharmaceutical composition includes any compound disclosed in U.S. Pat. No. 6,395,728, entitled "Method of treatment and pharmaceutical composition," as an active ingredient.

The disclosures of each of U.S. Pat. Nos. 7,572,920, 7,157,584, 5,656,560, 5,185,351, 5,270,317, 5,994,348, 6,342,247, 5,210,079, 5,608,075, 5,616,599, 6,878,703, 5,591,762, 6,358,986, 7,998,953, 5,399,578, 5,559,111, 5,972,990, 6,294,197, and 6,395,728, are hereby incorporated by reference, in their entireties, for all purposes, and specifically for the chemical structures of angiotensin II receptor blocker molecules disclosed therein.

Referring to block 412 of FIG. 4A, in some embodiments, the lowering of blood pressure is to treat and/or prevent heart disease. Typically, this treatment and/or prevention of heart disease is accomplished by a reduction in systemic vascular resistance and/or arterial pressure. For instance, in some embodiments this treatment and/or prevention of heart disease is accomplished by selectively blocking the binding of angiotensin II to the $AT_1$ receptor in many tissues. Blockage of the angiotensin II receptor inhibits the negative regulatory feedback of angiotensin II on renin secretion.

As described in detail below, method 400 includes eliciting medical information about the user, which is used to qualify or disqualify the subject for an over-the-counter provision of the angiotensin II receptor blocker pharmaceutical composition. However, in some embodiments, before beginning to elicit this information, the system registers the subject and/or ensures that the subject is prepared to proceed through the qualification process. For example, in some embodiments, the system first determines whether the subject has already registered, was previously qualified, and/or previously received a provision of the over-the-counter provision of the angiotensin II receptor blocker composition.

When the subject has not yet registered with the system, device 250 registers the subject as a new user and creates a corresponding user profile (e.g., regardless of whether the subject previously received a prescription provision of the angiotensin II receptor). The system then performs an assessment method (e.g., assessment method 400) to qualify the patient for a first over-the-counter provision of the angiotensin II receptor blocker pharmaceutical composition.

When the subject already has a user profile 234, e.g., as verified with a user password, the device registers the user as a returning customer. When the returning subject has previously received an over-the-counter provision of the angiotensin II receptor blocker pharmaceutical composition, the system performs a reassessment method (e.g., reassessment method 500) to qualify the subject for a subsequent provision. When the returning subject has not previously received an over-the-counter provision of the angiotensin II receptor blocker pharmaceutical composition (e.g., because they did not previously qualify or choose not to purchase the composition after being qualified), the system performs an assessment method (e.g., assessment method 400) to qualify the patient for a first over-the-counter provision of the angiotensin II receptor blocker pharmaceutical composition.

In some embodiments, where a new user does not already have a user profile 234 (e.g., the subject has not previously been qualified for an over-the-counter provision of the angiotensin II receptor blocker) the device registers the user as a new user and creates a corresponding user profile, regardless of whether the subject previously received a prescription provision of the angiotensin II receptor blocker. In some embodiments, when a new user has not previously been qualified for an over-the-counter provision of the angiotensin II receptor blocker, but has received a prescription for the angiotensin II receptor blocker, the device will consider the new user a returning user and will perform a re-order qualification (e.g., via method 500), rather than an initial qualification (e.g., via method 400).

In some embodiments, prior to eliciting medical information from the subject, the system prompts (e.g., 802 of FIG. 8A) to confirm that they have adequate privacy to provide sensitive medical information and/or that they are in possession of the medical information required to complete the qualification process. For example, in some embodiments the system prompts (e.g., 804 of FIG. 8A) the user to confirm that they have knowledge of their blood pressure, cardiovascular history, etc.

Blocks 414 Through 416.

Referring to block 414 of FIG. 4A, the method includes conducting an assessment survey of the subject. By way of the assessment survey, a plurality of assessment survey results to survey questions 208, 212 (e.g., one or more of the survey questions set forth in Table 1) are obtained (e.g., the device 250 transmits one or more assessment survey questions to the user, prompting a response, and then receives a response to the one or more assessment survey questions back from the subject). In some embodiments, the assessment survey results include some or all of the characteristics listed in Table 1. For example, in some embodiments, the plurality of assessment survey results includes 2, 3, 4, 5, 6, 7, 8, 9, 10, 11, 12, 13, 14, 15, 16, 17, 18, 19, 20, or all 21 of the characteristics listed in Table 1. In one embodiment, the plurality of assessment survey results includes at least characteristics 1-8 as provided in Table 1. In one embodiment, the plurality of assessment survey results includes at least characteristics 1-15 as provided in Table 1.

It will be appreciated that the survey questions 208, 212 and filters 216, 222 applied to the assessment survey answers thereof may vary depending upon the angiotensin II receptor blocker pharmaceutical composition being distributed. This varying is due to differences in the contraindication profiles of the various the angiotensin II receptor blocker pharmaceutical compositions, e.g., due to different drug-drug interactions, routes of drug clearance, etc. of the different the angiotensin II receptor blocker pharmaceutical compositions. For example, co-administration of a potassium supplement with a single oral dose of azilsartan medoxomil had no significant effect on the pharmacokinetics of azilsartan medoxomil. However, co-administration of a potassium supplement with valsartan resulted in increases in serum creatinine. See, Novartis Pharmaceuticals Corp., 2017, "Diovan—Highlights of Prescribing Information," Print. As such, in some embodiments, an assessment survey, or similarly a reassessment survey, qualifying a subject for OTC use of valsartan may ask whether the subject consumes a potassium supplement or similar salt in their diet, while a similar survey qualifying a subject for OTC use of azilsartan medoxomil may not.

Figure 8A:
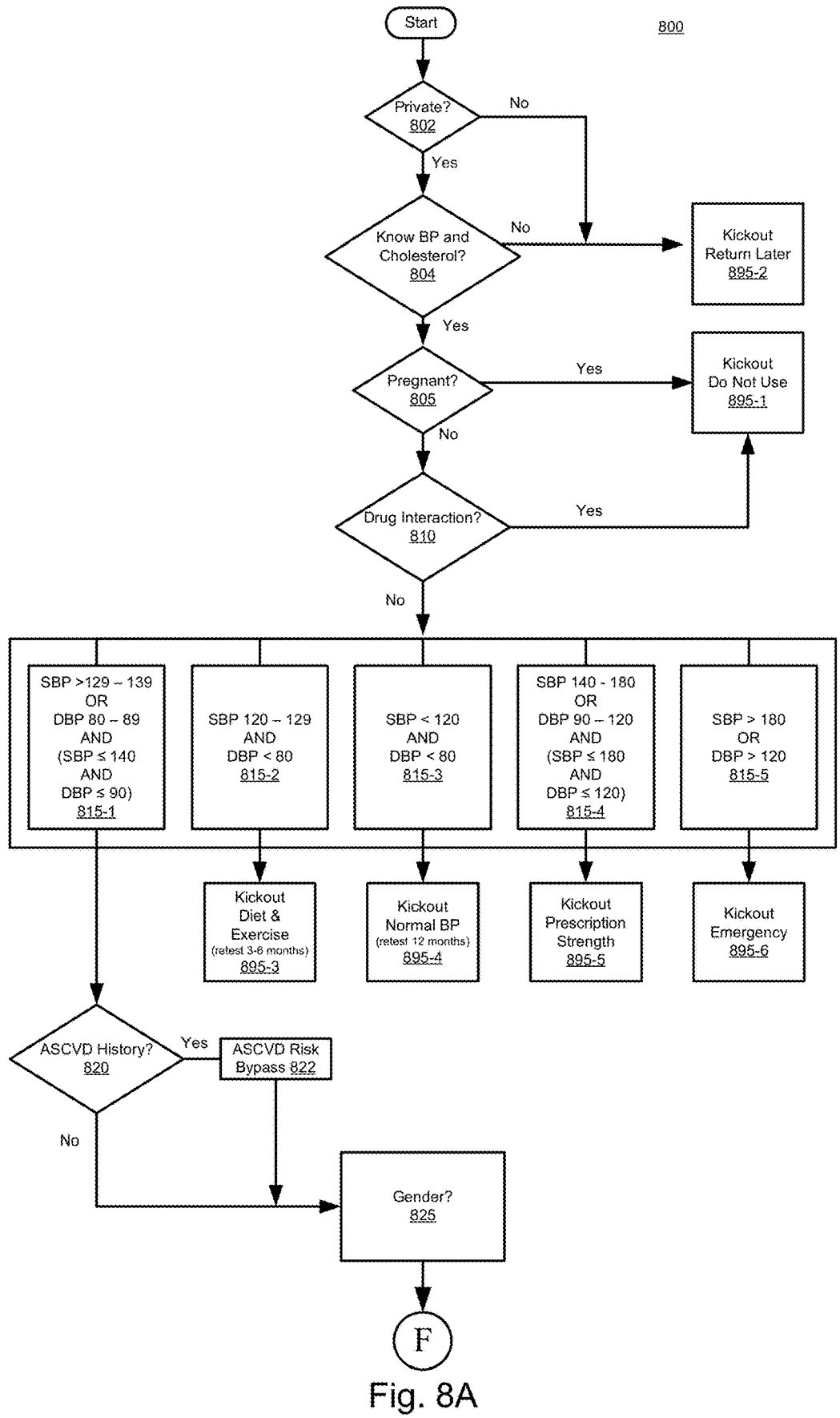
FIGS. 8A, 8B, and 8C collectively illustrate an example method for qualifying a subject for an over-the-counter provision of an angiotensin II receptor blocker pharmaceutical composition, in accordance with an embodiment of the present disclosure.
Figure 8B:
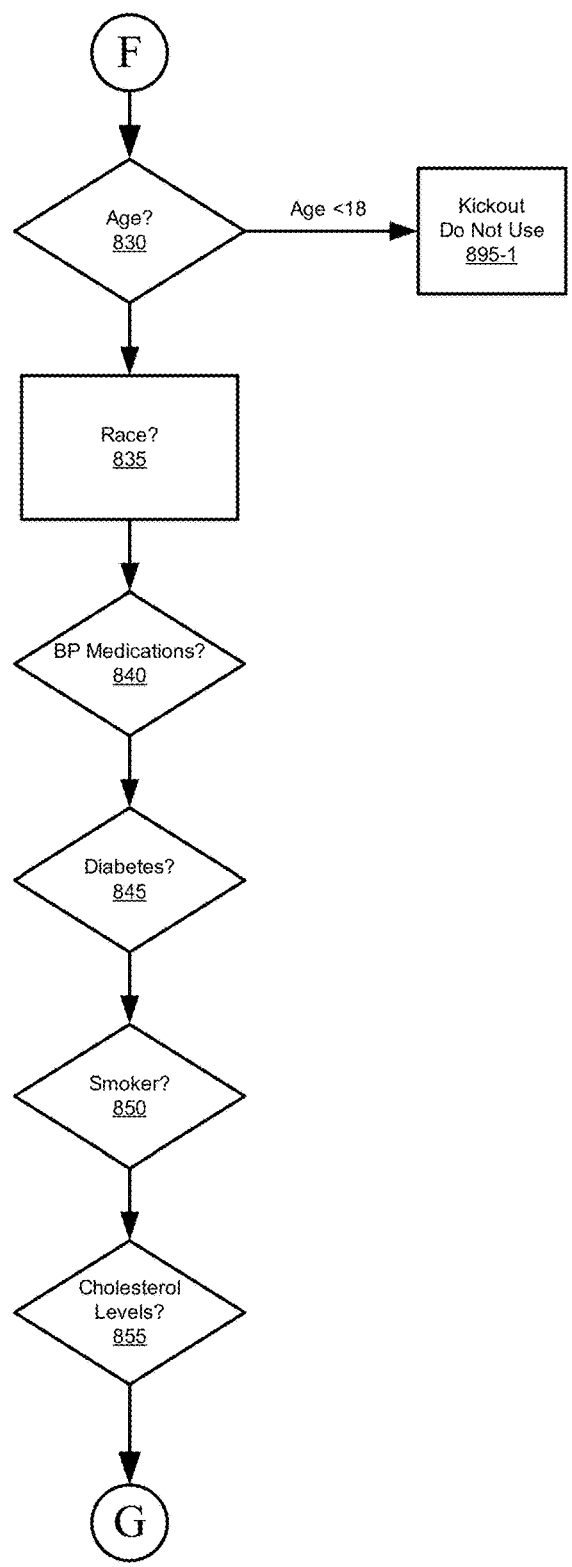

Referring to block 416, and as further illustrated in FIG. 8, in some embodiments the assessment survey results include whether the subject is one of pregnant, breastfeeding, or planning to become pregnant (e.g., responsive to a survey question 208 that is associated with and/or applied to (805) a pregnancy assessment filter 216-1 of a first category class), whether the subject is taking a medication that interacts with the angiotensin II receptor blocker pharmaceutical composition (e.g., responsive to a survey question 208 that is associated with and/or applied to (810) a drug interaction assessment filter 216-2 of a first category class), a systolic blood pressure of the subject (e.g., responsive to a survey question 208 that is associated with and/or applied to (815, 865) a blood pressure assessment filter 216-3 of a first category class, and/or a pooled cohort equation assessment filter 216-5 of a first category class), a diastolic blood pressure of the subject (e.g., responsive to a survey question 208 that is associated with and/or applied to (815) a blood pressure assessment filter 216-3 of a first category class), an age of the subject (e.g., responsive to a survey question 208 that is associated with and/or applied to (830) an age assessment filter 216-4 of a first category class), information required to calculate a risk of atherosclerotic cardiovascular disease for the subject (e.g., responsive to a survey question 208 that is associated with and/or applied to (825 through 865) a pooled cohort equation assessment filter 216-5 of a first category class), whether the subject has ever had an abnormal electrolyte blood level (e.g., responsive to a survey question 212 that is associated with and/or applied to (875) an abnormal electrolyte blood level assessment filter 222-2 of a second category class), and whether the subject has ever had a kidney problem (e.g., response to a survey question 212 that is associated with and/or applied to (870) a kidney problem assessment filter 222-1 of a second category class).

In some embodiments, the assessment survey includes questions that elicit responses providing some or all of the characteristics listed in Table 1. In some embodiments, the assessment survey includes questions corresponding to each of the assessment survey results required for the methods described herein. In other embodiments, the assessment survey includes questions corresponding to only a subset of the assessment survey results required for the methods described herein. For instance, in some embodiments the subset of assessment survey results corresponds to a respective angiotensin II receptor blocker (e.g., a first subset corresponds to azilsartan, a second subset corresponds to olmesartan, etc.). In such embodiments, one or more assessment survey results required for the methods described herein are acquired through other means (e.g., upon registration/subscription for a service associated with qualifying the subject for over-the-counter medication, from a healthcare provider, from a prior survey, from a database associated with a pharmacy, from an electronic health record associated with the subject, from the subject profile data store 232, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a blood pressure measurement determined for the subject).

TABLE 1

Example Medical Information Elicited from Assessment Survey Questions

| Result | Example Characteristics |
|---|---|
| 1 | whether the subject pregnant or breastfeeding |
| 2 | whether the subject is taking a medication that interacts with the angiotensin II receptor blocker pharmaceutical composition |

TABLE 1-continued

Example Medical Information Elicited from Assessment Survey Questions

| Result | Example Characteristics |
|---|---|
| 3 | a systolic blood pressure of the subject |
| 4 | a diastolic blood pressure of the subject |
| 5 | an age of the subject |
| 6 | information required to calculate a risk of atherosclerotic cardiovascular disease for the subject |
| 7 | whether the subject has ever had an abnormal electrolyte blood level |
| 8 | whether the subject has ever had a kidney problem |
| 9 | a gender of the subject |
| 10 | a race of the subject |
| 11 | a blood pressure medication status of the subject |
| 12 | a smoking status of the subject |
| 13 | a total cholesterol level of the subject |
| 14 | a high density lipoprotein cholesterol level of the subject |
| 15 | a diabetes status of the subject |
| 16 | whether the subject has ever had an atherosclerotic cardiovascular history including an atherosclerotic cardiovascular event or a heart procedure |
| 17 | whether the subject has ever had liver problems |
| 18 | whether the subject is taking a potassium supplement or a salt substitute that includes potassium |
| 19 | whether the subject is taking colesevelam |
| 20 | whether the subject has ever had a heart failure |
| 21 | whether the subject is allergic to the angiotensin II receptor blocker pharmaceutical composition |

It is contemplated that, in some embodiments, any one or more of the survey questions 208, 212 provided in Table 1 will not be included in the assessment survey (e.g., will not be used for the assessment). For example, in some embodiments, a characteristic associated with a particular survey question will be informative when qualifying a subject for one particular angiotensin II receptor blocker but not for another angiotensin II receptor blocker. For instance, in some embodiments an assessment survey question is queried for azilsartan medoxomil qualifying surveys but not for telmisartan qualifying surveys (e.g., the assessment survey question is not relevant for telmisartan). The skilled artisan will recognize that different angiotensin II receptor blockers carry different risk and drug interaction profiles. Accordingly, assessment survey information required for qualifying a subject for access to one angiotensin II receptor blocker with a known adverse drug interaction may not be necessary for qualifying the same subject for access to a second angiotensin II receptor blocker.

Accordingly, it is contemplated that the assessment survey questions 208 include any subset of survey results provided in Table 1. For brevity, all possible combinations of the survey questions 208, 212 provided in Table 1 are not specifically delineated here. However, the skilled artisan will easily be able to envision any particular subset of the survey questions 208, 212 provided in Table 1. Likewise, the skilled artisan may know of other survey questions, not provided in Table 1, that may be combined with any subset of the survey questions provided in Table 1 to form the assessment survey questions used in the methods described herein.

In some embodiments, the assessment survey and/or the reassessment survey is conducted by transmitting a plurality of respective questions to the subject, e.g., some or all of the respective survey questions, and receiving answers to the plurality of respective survey questions before applying any of the answers to respective filters. For example, with reference to the workflow in FIG. 8, the device transmits questions relating to all of the assessment filters of the first category class, all of the assessment filters of the second category class, or all of the assessment filters in the workflow (e.g., as a virtual assessment survey where all of the questions are displayed in a single user interface, or as a series of questions displayed in consecutive user interfaces). After receiving answers to all of the assessment survey questions, the device then applies the answers to all of the assessment filters (e.g., sequentially or concurrently) to determine whether the subject is qualified to receive a provision of the angiotensin II receptor blocker pharmaceutical composition. In alternative embodiments, the device transmits questions relating to just those assessment filters of the first category class for which it could not obtain answers to the questions from an electronic database associated with the subject, such as electronic health record of the subject, and just those assessment filters of the second category class it could not obtain answers to the questions from an electronic database associated with the subject (e.g., as a virtual assessment survey where such unanswered questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the angiotensin II receptor blocker pharmaceutical composition.

Figure 6C:
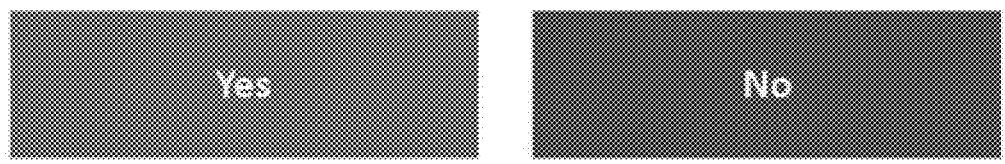
Figure 6D:
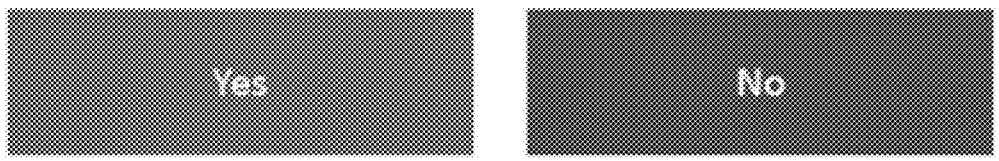

In some embodiments, the assessment survey and/or the reassessment survey is conducted in a serial fashion, e.g., by transmitting a first question or a first group of survey questions (e.g., associated with a single respective filter) to the subject, receiving an answer to the single survey question or small group of survey questions, and applying the answer or answers to a filter, prior to transmitting a second question or second group of questions to the subject. For example, with reference to the workflow in FIG. 8, in some embodiments the device transmits a first assessment question to the subject, relating to the body electrolyte levels in the blood of the subject (e.g., question 650 'Are you pregnant or breastfeeding, think you may be pregnant, or plan to become pregnant?' in FIG. 6C). After receiving the answer to the survey question (e.g., 'yes or no'), the device applies the answer to an assessment pregnancy filter (805). If the assessment pregnancy filter is fired (e.g., in response to a "yes" answer), the device terminates (895-1) the process, and optionally provides the user with a message relating to why they are being denied a provision of the angiotensin II receptor blocker pharmaceutical composition, a suggestion for following-up with a medical professional (e.g., as illustrated in FIG. 6B, when the survey answers indicate that the subject has had abnormal body salt levels in their blood (875), the device optionally terminates the process (880) and advises that the subject seek guidance from a professional medical practitioner), and/or a suggestion to make a lifestyle change (e.g., as illustrated in FIG. 8A, when the survey answers indicate that the subject has slightly elevated blood pressure (815-2), the device terminates the process (895-3) and advises that the subject improve their diet or exercise routine which is consistent with current blood pressure treatment guidelines), to treat or manage their blood pressure.

In some embodiments, one or more survey questions are not transmitted to a respective subject in accordance with a result to a previous survey question. For instance, in some embodiments where the ASCVD risk calculation is bypassed by an indication that the subject has a history of ASCVD (e.g., bypass mechanism 863 in FIG. 8C), if an assessment survey result indicates that a subject has a history of ASCVD (e.g., at step 820 in FIG. 8A), one or more assessment survey questions related to a pooled cohort equation assessment filter are bypassed (not transmitted to the user) because the ASCVD pooled cohort filter can be bypassed.

In some embodiments, the assessment survey includes one or more questions that elicit responses that provide some or all of the characteristics listed in Table 1. In some embodiments, the assessment survey includes questions corresponding to each of the survey results required for the methods described herein. In other embodiments, the assessment survey includes questions corresponding to only a subset of the survey results required for the methods described herein. In such embodiments, the other survey results required for the methods described herein are acquired through other means (e.g., upon registration and/or subscription for a service that is associated with qualifying the subject for over-the-counter medication, from a healthcare provider, from a prior survey (e.g., from an assessment survey if a subject is taking a reassessment survey), from a database associated with a pharmacy, etc.) For example, in some embodiments, the subject provides a personal medical identification (e.g., identifier) associated with an insurer, a hospital, and/or another healthcare provider and information about the subject required for the methods described herein, e.g., one or more survey results, is acquired from a preexisting database associated with the personal medical identification (e.g., a last cholesterol or blood pressure measurement determined for the subject). The same applies to the reassessment survey module 254 and corresponding results applied to the assessment survey module 252.

As described in detail below, the methods disclosed herein include steps of applying information collected about a subject to a plurality of filters designed to identify contraindications—which render the subject unsuitable for treatment with the angiotensin II receptor blocker generally or at least in the self-care environment (i.e., without physician supervision)—and risk factors—which render administration of the angiotensin II receptor blocker unnecessarily risky without further physician consultation. The contraindication and risk factors described herein are non-exhaustive, as the skilled artisan will know of other possible contraindications or risk factors for a particular angiotensin II receptor blocker pharmaceutical composition. Moreover, as medical research progresses, new contraindications or risk factors may be discovered. Or, similarly, the classification of existing contraindications or risk factors may change with additional medical research or consideration. For example, a factor considered to be a contraindication may be reclassified as a risk factor, over time, or vice-a-versa.

Further, a contraindication for one angiotensin II receptor blocker pharmaceutical composition may only be a risk factor, or neither, for a different angiotensin II receptor blocker pharmaceutical composition, for example, based on different mechanisms, interaction, pharmacokinetic, and/or pharmacodynamics properties of the respective active ingredients. Similarly, a factor that is a contraindication or risk factor for a particular angiotensin II receptor blocker pharmaceutical composition when administered at one dose, e.g., a high, moderate, or low dose, may be classified differently when administered at a different dose. For example, a contraindication for an angiotensin II receptor blocker pharmaceutical composition administered at a high dose may only be a risk factor, or neither, when administered at a low dose. This is particularly true when the risk factor, e.g., a drug interaction, changes the bioavailability of the active ingredient by a certain factor, such that the bioavailability following high dose administration, but not low dose administration, would increase beyond a safe threshold.

Blocks 418-452.

Referring to block 418 of FIG. 4B, all or a portion of the assessment survey results are run against a first plurality of assessment filters of a first category class 214. As previously described, the first plurality of assessment filters includes a subset of filters 216 of the first filter category class 214. When a respective filter in the first plurality of assessment filters is fired (e.g., in accordance with a determination that a survey result indicates that a triggering condition 218 has been met), the subject is deemed not qualified for delivery of the angiotensin II receptor blocker pharmaceutical composition and the method is terminated without delivery of the angiotensin II receptor blocker pharmaceutical composition.

In some embodiments, e.g., when the method is terminated without delivery of the angiotensin II receptor blocker pharmaceutical composition, the subject is prevented from attempting to requalify for the angiotensin II receptor blocker pharmaceutical composition for a predetermined period of time. This prevents the subject from abusing the systems and methods of the present disclosure.

Referring to blocks 420-470 of FIGS. 4B through 4E, specific assessment filters 216 in the first plurality of assessment filters and their exemplary triggering conditions 218 that cause the corresponding assessment filter to fire are described.

In some embodiments, the first plurality of assessment filters of the first category class 214 includes some or all of the filters 216 listed in Table 2. For example, in some embodiments, the first plurality of assessment filters results includes 2, 3, 4, or all 5 of the filters listed in Table 2.

TABLE 2

Example Assessment Filters of the First Category Class

| Filter | Example Criteria |
|---|---|
| 1a | a pregnancy assessment filter |
| 2a | a drug interaction assessment filter |
| 3a | a blood pressure assessment filter |
| 4a | an age assessment filter |
| 5a | a pooled cohort equation assessment filter |
| 6a | a liver disease assessment filter |

In one embodiment, the first plurality of assessment filters includes at least filters 1a-5a as provided in Table 2. In some embodiments, where the particular angiotensin II receptor blocker pharmaceutical composition is contraindicated for administration to patients with liver disease, the first plurality of assessment filters further includes filter 6a.

It is contemplated that, in some embodiments, any one or more of the assessment filters 216 provided in Table 2 will not be included in the first plurality of assessment filters. For example, in some embodiments, a characteristic associated with a particular survey result will be informative if qualifying a subject for one particular angiotensin II receptor blocker but not for another angiotensin II receptor blocker, e.g., filter 6a. In some implementations, one or more of the assessment filters 216 provided in Table 2 is implemented as a second type filter, as described below, which only provides a warning to the user and/or requires the user confirm they have spoken to a physician about the underlying risk.

Accordingly, it is contemplated that in some embodiments the first plurality of assessment filters includes any sub-set of filters 216 provided in Table 2. Likewise, in some embodiments the skilled artisan may know of other filters 216, not are provided in Table 2, which may be combined with any subset of the filters 216 provided in Table 2 to form the first plurality of assessment filters and corresponding results used in the methods described herein. For brevity, all possible combinations of the assessment filters 216 provided in Table 2 are not specifically delineated here.

Referring to blocks 420-422 of FIG. 4B, in some embodiments the first plurality of assessment filters includes a pregnancy filter (e.g., pregnancy assessment filter 216-1 in FIG. 3 and/or filter 1a in Table 2). In some embodiments, the pregnancy assessment filter is configured to be fired at least when the first plurality of assessment survey results indicates that the subject is pregnant or the subject is breastfeeding. In some embodiments, the pregnancy assessment filter is also configured to be fired when the subject is planning on becoming pregnant. When the pregnancy assessment filter is fired, the subject is not permitted to obtain the angiotensin II receptor blocker pharmaceutical composition over-the-counter (e.g., the method is terminated without authorizing provision of the angiotensin II receptor blocker pharmaceutical composition to the subject). For example, in some embodiments the device transmits prompt 654, as illustrated in FIG. 6C, to the subject and the device applies the answer provided by the subject to the pregnancy assessment filter. If the subject's answer indicates that they are pregnant, they are planning on being pregnant, they are breastfeeding, or they are planning to breastfeeding, the pregnancy assessment filter is fired and the method is terminated without authorizing provision of the angiotensin II receptor blocker pharmaceutical composition to the subject. In some embodiments, the device transmits a message explaining why authorization was denied.

Referring to blocks 424 through 430 of FIG. 4B, in some embodiments, the first plurality of assessment filters includes a drug interaction filter (e.g., drug interaction assessment filter 216-2 in FIG. 3 and/or filter 2a in Table 2). The drug interaction assessment filter is configured to be fired at least when the first plurality of assessment survey results indicates that the subject is taking a medication that interacts with the angiotensin II receptor blocker pharmaceutical composition. When the drug interaction assessment filter is fired, the device transmits a warning corresponding to the drug interaction assessment filter, and requires the user to acknowledge the warning before authorizing a provision of the angiotensin II receptor blocker pharmaceutical composition.

In some embodiments, a drug capable of firing the drug interaction assessment filter includes a lithium medication or supplement. For instance, in some embodiments (e.g., embodiments in which the angiotensin II receptor blocker pharmaceutical composition includes azilsartan medoxomil, increases in the serum lithium concentrations and/or lithium toxicity have been observed if the angiotensin II receptor blocker is administered with a lithium medication.

In some embodiments, a drug capable of firing the drug interaction assessment filter includes a non-steroidal anti-inflammatory drug (NSAID). In some embodiments, a non-steroidal anti-inflammatory drug capable of firing the drug interaction assessment filter includes ibuprofen. In some embodiments, a non-steroidal anti-inflammatory drug capable of firing the drug interaction assessment filter includes naproxen.

In some embodiments, a drug capable of firing the drug interaction assessment filter includes a blood pressure medication. For instance, in some embodiments the drug interaction assessment filter is fired if the assessment survey results indicate that the subject is taking a medication for treating and/or preventing high blood pressure. In some embodiments, these high blood pressure medications include a diuretic medication such as a water pill.

The identity (e.g., active ingredient(s), inactive ingredient(s), or a combination thereof) of one or more drugs that are capable of triggering the drug interaction assessment filter vary from one angiotensin II receptor blocker to another angiotensin II receptor blocker. The skilled artisan will know of one or more drugs that interact with one angiotensin II receptor blocker but not another. Inclusion of a drug within the drug interaction assessment filter is dependent upon the identity and/or the dosage of the angiotensin II receptor blocker pharmaceutical composition being authorized for over-the-counter use.

In some embodiments, a drug that interacts with an angiotensin II receptor blocker pharmaceutical composition is included within a filter 222 in the second filter category class 220, rather than within drug interaction assessment filter 216 of the first filter category class 214. For example, according to some implementations, a particular drug included in drug-interaction assessment filter 216 (e.g., as a risk factor) for a first angiotensin II receptor blocker pharmaceutical composition, but included in a filter in the second plurality of assessment filters (e.g., as a contraindication) for a second angiotensin II blocker pharmaceutical composition. However, a person skilled in the art will know whether to include a certain drug within drug interaction assessment filter 216 or as a separate filter 222 in the second plurality of assessment filters, based on the severity and risk of the drug interaction with the particular identity and dosage of the angiotensin II receptor blocker being authorized for over-the-counter use.

Referring to blocks 432 through 442 of FIGS. 4B and 4C, in some embodiments the first plurality of assessment filters includes a blood pressure assessment filter (e.g., blood pressure assessment filter 216-3 in FIG. 3 and/or filter 3a in Table 2). In some embodiments, the blood pressure assessment filter is configured to be fired at least when the plurality of assessment survey results indicates that the subject is not hypertensive or the subject has severe hypertension. If the blood pressure assessment filter is fired, the subject is not permitted to obtain the angiotensin II receptor blocker pharmaceutical composition over-the-counter (e.g., the method is terminated without authorizing provision of the angiotensin II receptor blocker pharmaceutical composition to the subject).

In some embodiments, the blood pressure assessment filter is fired when the plurality of assessment survey results indicates that the systolic blood pressure of the subject is less than a floor systolic pressure and a diastolic blood pressure of the subject is greater than a floor diastolic blood pressure. In some embodiments, the floor systolic pressure is 131 mm Hg and the floor diastolic pressure is 81 mm Hg. In some embodiments, the floor systolic pressure is 130 mm Hg and the floor diastolic pressure is 80 mm Hg. In some embodiments, the floor systolic pressure is 129 mm Hg and the floor diastolic pressure is 79 mm Hg. For instance, in some embodiments the blood pressure assessment filter is fired if the assessment survey results indicate that the subject is not hypertension (e.g., a systolic blood pressure of at least 130 mm Hg and a diastolic blood pressure of at least 80 mm Hg). In some embodiments, the blood pressure assessment filter is fired if the assessment survey results indicate that the subject has severe hypertension (e.g., a systolic blood pressure of at least 140 mm Hg or a diastolic blood pressure of at least 90 mm Hg). Furthermore, in some embodiments if the plurality of assessment survey results indicate that the subject has elevated blood pressure but is not hypertension, the blood pressure filter is fired. Accordingly, advice is transmitted to the subject to manage their blood pressure by eating healthy and exercising. In some embodiments, if the plurality of assessment survey results indicate that the subject has stage two (II) hypertension, the blood pressure assessment filter is fired. Accordingly, advice is transmitted to the subject to discuss taking a prescription-strength blood pressure medication with a professional medical practitioner. Furthermore, in some embodiments if the plurality of assessment survey results indicate that the subject is in hypertension crises, the blood pressure assessment filter is fired. Accordingly, advice is transmitted to the subject to seek emergency medical attention. In some embodiments, the blood pressure cutoffs (e.g., a blood pressure floor and/or ceiling) defining when the blood pressure filter is fired and when the blood pressure filter is not fired are set according to a set of healthcare guidelines, which may change over time, and/or vary on a jurisdiction-by-jurisdiction basis. For example, in the United States, the American College of Cardiology and the American Heart Association collaborated to provide guidance on management of high blood pressure. Whelton P K, et al., J Am Coll Cardiol., S0735-1097(17)41519-1 (2017), the contents of which are hereby expressly incorporated by reference. These guidelines change over time as medical research and advances in treatment better inform management of high blood pressure.

In some embodiments, e.g., when the plurality of assessment survey results indicate that the subject has elevated blood pressure but is not hypertensive (e.g., a systolic blood pressure in between 120 and 129 mm Hg and a diastolic blood pressure less than 80 mm Hg), the first blood pressure filter is fired, and advice is transmitted to the subject to manage their blood pressure by eating healthy and exercising. In some embodiments, e.g., when the plurality of assessment survey results indicate that the subject has hypertension stage two (e.g., a systolic blood pressure greater than or equal to 140 mm Hg or a diastolic blood pressure greater than or equal to 90 mm Hg), the first blood pressure filter is fired and advice is transmitted to the subject to visit a doctor to discuss taking a prescription-strength blood pressure medication. In some embodiments, e.g., when the plurality of assessment survey results indicate that the subject is in hypertension crisis (e.g., a systolic blood pressure greater than 180 mm Hg and/or a diastolic blood pressure greater than 120 mm Hg), the first blood pressure filter is fired, and advice is transmitted to the subject to seek emergency medical attention.

Referring to blocks 444 and 446 of FIG. 4C, in some embodiments the first plurality of assessment filters includes an age assessment filter (e.g., age filter 216-4 in FIG. 3 and/or filter 4a in Table 2). In some embodiments, the age assessment filter is fired when the plurality of assessment survey results indicates that the subject is too young to receive the angiotensin II receptor blocker pharmaceutical composition. For instance, in some embodiments an age in which the subject is too young to receiving the angiotensin II receptor blocker pharmaceutical composition is determined by on a jurisdiction-by-jurisdiction basis (e.g., a first subject in one geographic region is of age to receive the angiotensin II receptor blocker while a second subject in another geographic region of the same age is not permitted to receiving the angiotensin II receptor blocker). In some embodiments, the age assessment filter is fired when the plurality of assessment survey results indicates that the subject is less than sixteen years old. In some embodiments, the age assessment filter is fired when the plurality of assessment survey results indicates that the subject is less than eighteen years old. In some embodiments, the age assessment filter is fired when the plurality of assessment survey results indicates that the subject is less than twenty-one years old. If the age assessment filter is fired, the subject is not permitted to obtain the angiotensin II receptor blocker pharmaceutical composition pharmaceutical composition over-the-counter (e.g., the method is terminated without authorizing provision of the angiotensin II receptor blocker pharmaceutical composition to the subject).

In some embodiments, the age filter is fired when the plurality of assessment survey results indicates that the subject has an age for which a risk of an atherosclerotic cardiovascular disease (ASCVD) event cannot be calculated according to a predictive algorithm (e.g., a 10-year risk estimate for a hard ASCVD event using the pooled cohort equations provided in Goff, D C Jr. et al., Circulation (2013). For example, in some embodiments, the age assessment filter is fired when the plurality of assessment survey results indicates that the subject is less than forty years old, which would provide an incalculable risk using the equations in Goff et al. Similarly, in some embodiments the age assessment filter is fired when the plurality of assessment survey results indicates that the subject is older than seventy-nine years old.

Referring to blocks 448 through 458 of FIGS. 4C and 4D, in some embodiments the first plurality of assessment filters includes a pooled cohort equation assessment filter (e.g., pooled cohort equation filter 216-5 in FIG. 3 and/or filter 5a in Table 2). In some embodiments, the pooled cohort equation assessment filter incorporates the gender of the subject, the race of the subject, the age of the subject, the blood pressure medication status of the subject, the total cholesterol level of the subject, the HDL cholesterol count of the subject, the systolic blood pressure of the subject, the smoking status of the subject (e.g., whether the subject currently smokes or has smoked in the past), and the diabetes status of the subject (e.g., whether the subject has Type-1 diabetes, Type-2 diabetes, etc.) to derive a risk for atherosclerotic cardiovascular disease (e.g., a risk for experiencing an atherosclerotic cardiovascular disease (ASCVD) event within a certain timeframe, such as within five or ten years). In some embodiments, the pooled cohort equation also incorporates a familial history of premature heart or stroke (e.g., a history of heart attack or stroke before the age of forty-five, fifty, fifty-five, sixty, etc.). In some embodiments, the pooled cohort equation incorporates a high sensitive quantification of c-reactive protein (hsCRP) level of the subject. Nevertheless, in some embodiments the pooled cohort equation assessment filter is fired if the plurality of assessment survey results indicate that the subject has a risk for atherosclerotic cardiovascular that is either below a floor threshold of risk or the subject has an incalculable risk for atherosclerotic cardiovascular disease. If the pooled cohort equation filter is fired, the subject is not permitted to obtain the angiotensin II receptor blocker pharmaceutical composition pharmaceutical composition over-the-counter (e.g., the method is terminated without authorizing provision of the angiotensin II receptor blocker pharmaceutical composition to the subject).

In some embodiments, the pooled cohort equation assessment filter is configured to be fired at least when the plurality of assessment survey results indicates that, despite having hypertension stage 1 (e.g., a systolic blood pressure of 130 to 139 mm HG or a diastolic blood pressure of 80 to 89 mm Hg) the subject has a risk for atherosclerotic disease that falls below a minimum risk threshold (e.g., the subject does not have a high enough risk of having an ASCVD event to justify taking a angiotensin II receptor blocker pharmaceutical composition). In some embodiments, the risk for the atherosclerotic cardiovascular disease calculated using the pooled cohort equation is a lifetime risk, a 5-year risk, or a 10-year risk. Furthermore, in some embodiments the risk for the atherosclerotic cardiovascular disease using the pooled cohort equation is in a range of a year to a lifetime (e.g., 100 years, 80 years, 50 years, etc.). In some embodiments, the pooled cohort equation is implemented as a multivariable Cox proportional hazard regression.

In some embodiments, the pooled cohort equation assessment filter is fired at least when the assessment survey results indicate the subject has a 10-year risk for atherosclerotic cardiovascular disease (e.g., a 10-year risk of experiencing an atherosclerotic cardiovascular disease (ASCVD) event) that is less than 10%, as determined by the pooled cohort equation. In some embodiments, the pooled cohort equation assessment filter is also configured to be fired when one or more value provided by the subject does not enable the pooled cohort equation to calculate an ASCVD event risk for the subject (e.g., a subject age of less than forty would provide an incalculable risk using the equations provided in Goff et al.). In some embodiments, the pooled cohort equation assessment filter behaves as a filter of the second category class when a value provided by the subject does not enable the pooled cohort equation to calculate an ASCVD event risk. E.g., when the pooled cohort equation filter is fired for receiving a value that is out of a range of values required to calculate an ASCVD event risk, the device issues a warning to the subject (e.g., requiring the subject discuss taking a angiotensin II receptor blocker pharmaceutical composition with a medical professional) that must be acknowledged prior to being authorized to receive a provision of the angiotensin II receptor blocker pharmaceutical composition, rather than automatically terminating the process, as would be done when a filter of the first category class is filtered. In some embodiments, the pooled cohort equation assessment filter is fired when the assessment survey results indicate the subject is younger than forty years old.

The pooled cohort equation estimates the probability of incurring a hard atherosclerotic cardiovascular disease (ASCVD) event in a given period of time, such as in the next 5 years, the next 10 years, or in the lifetime of a subject. In some embodiments, the pooled cohort equation for the pooled cohort equation filter is calculated using the guidelines set forth in Goff, D C Jr, et al., J. Am. Coll. Cardiol., 63:2935-59 (2014), the content of which is hereby incorporated by reference. Following the Goff et al. (Id.) calculation of the 10-year risk estimate for a hard ASCVD event using the pooled cohort equations is done as a series of steps. The natural log of the age of the subject, total cholesterol, HDL-C, and systolic blood pressure are first calculated with the systolic blood pressure being either a treated or untreated value. For example, calculation of the pooled cohort equations estimate the probability of a Caucasian male subject 55 years of age with total cholesterol 213 mg/dL, HDL-C 50 mg/dL, untreated systolic blood pressure 120 mm Hg, nonsmoker, and without diabetes determine the probability of a hard ASCVD event in the next 10 years using Goff Id. begins by first taking the natural log of the subject's age (4.01), the natural log of the subject's total cholesterol (5.36), the natural log of the subject's HDL-C (3.91), and the natural log of the subject's systolic blood pressure (4.79). These values are then multiplied by the coefficients from the equation ("Coefficient" column of Table A of Goff Id.) for the specific race-gender group of the individual to obtain "coefficient×values." That is:

multiply the natural log of the subject's age (4.01) by the coefficient 12.344 to obtain the "coefficient×value" of 49.47, multiply the natural log of the subject's total cholesterol (5.36) by the coefficient 11.853 to obtain the "coefficient×value" of 63.55, multiply the natural log of the subject's HDL-C (3.91) by the coefficient −7.990 to obtain the "coefficient×value" of −31.26, and multiply the natural log of the subject's systolic blood pressure (4.79) by the coefficient 1.764 to obtain the "coefficient×value" of 8.45.

Any appropriate interaction terms are also calculated. Following Goff Id., in the case of the Caucasian male subject 55 years of age, the interaction terms are:

the Log Age (4.01)×Log total Cholesterol (5.36) multiplied by the coefficient −2.664 to obtain the "coefficient×value" of −57.24 and Log Age (4.01)×Log HDL-C (3.91) multiplied by the coefficient 1.769 to obtain the "coefficient×value" of 27.73.

The sum of these "coefficient×values" is then calculated for the individual (49.47+63.55−31.26+8.45−57.24+27.73=60.69). The estimated 10-year risk of a first hard ASCVD event is formally calculated as 1 minus the baseline survival rate at 10 years for the gender/race (in this example Caucasian male), raised to the power of the exponent of the "Coefficient×Value" sum calculated above minus the race (Caucasian) and gender (Male) specific overall mean "Coefficient×Value" sum; or, in equation form:

$$1 - 0.9144^{e^{(60.69-61.18)}}$$

where the number 0.9144 is the baseline survival rate at 10 years for Caucasian males from Goff Id, the number 60.69 is the "coefficient×value" calculated for the particular subject as detailed above, and the number 61.18 is the race (Caucasian) and gender (Male) specific overall mean "Coefficient×Value" from Goff Id. This equates to a 5.3% probability of a first hard ASCVD event within 10 years.

In some embodiments, using the Goff et al. calculation, the risk for the fatal cardiovascular disease used in calculating the pooled cohort equation is a 10-year risk, and a first threshold value, e.g., a threshold value which when the risk of the subject is determined to be less than fires the filter, is about 10% risk. In some embodiments, the risk for the fatal cardiovascular disease used in calculating the pooled cohort equation is a 10-year risk, and the first threshold value is a 10% risk.

In some embodiments, the pooled cohort equation filter incorporates some or all of the characteristics listed in Table 3, e.g., as determined from a set of survey results, to derive a subject risk for atherosclerotic cardiovascular disease. For example, in some embodiments, the plurality of assessment survey results includes 2, 3, 4, 5, 6, 7, 8, 9, 10, or all 11 of the characteristics listed in Table 3. The pooled cohort equation filter is fired when the subject's risk for atherosclerotic cardiovascular disease exceeds a threshold level of risk.

TABLE 3

Example Characteristics Used for Pooled Cohort Equation Filter

| Result | Exemplary Characteristics |
|---|---|
| 1 | a gender of the subject |
| 2 | an age of the subject |
| 3 | a total cholesterol level of the subject |
| 4 | a HDL cholesterol count of the subject |
| 5 | a systolic blood pressure of the subject |
| 6 | a race of the subject |
| 7 | whether the subject is taking one or more medications for hypertension |
| 8 | a smoking status of the subject |
| 9 | a diabetes status of the subject |
| 10 | whether the subject has a family history of heart or stroke before the age of 60 |
| 11 | a hsCRP level of the subject |

In some embodiments, the pooled cohort equation used to calculate a risk of fatal cardiovascular disease for the pooled cohort equation filter is calculated using the guidelines set forth in Perk J. et al., European Guidelines on cardiovascular disease prevention in clinical practice, European Heart Journal 33:1635-1701 (2012), which is hereby incorporated by reference herein. In some embodiments, the pooled cohort equation assessment filter follows a low CVD risk SCORE chart, which incorporates the gender of the subject, the age of the subject, the total cholesterol level of the subject, the systolic blood pressure of the subject, and a smoking status of the subject, as set forth in Perk J. et al., Supra. In some embodiments, a conversion factor is used to convert a risk of fatal cardiovascular disease to a risk of fatal plus nonfatal hard cardiovascular disease events, as set forth in Catapano A L et al., 2016 ESC/EAS Guidelines for the Management of Dyslipidaemias. Eur Heart J. 2016 Oct. 14; 37(39):2999-3058, which is hereby incorporated by reference herein. In one embodiment, the pooled cohort equation filter incorporates at least survey results 1-9 as provided in Table 3, e.g., according to the method described in Goff, D C Jr, et al., J. Am. Coll. Cardiol., 63:2935-59 (2014). In another embodiment, the assessment survey results include at least survey results 1-10 as provided in Table 3. In another embodiment, the assessment survey results include at least survey results 1-9 and 11 as provided in Table 3. In another embodiment, the assessment survey results include at least survey results 1-11 as provided in Table 3.

In some embodiments, using the SCORE guidelines, the risk for the fatal cardiovascular disease used in calculating the pooled cohort equation is a 10-year risk, and a first threshold value, e.g., a threshold value which when the risk of the subject is determined to be less than fires the filter, is a 5% risk. In some embodiments, the risk for the fatal cardiovascular disease used in calculating the pooled cohort equation is a 10-year risk, and the first threshold value is a 10% risk.

In some embodiments, the pooled cohort equation used to calculate a risk of a cardiovascular disease-related death for the pooled cohort equation filter is calculated using the guidelines set forth in Teramoto et al., Japan Atherosclerosis Society. Executive summary of the Japan Atherosclerosis Society (JAS) guidelines for the diagnosis and prevention of atherosclerotic cardiovascular diseases in Japan-2012 version, J Atheroscler Thromb., 2013; 20(6):517-23, which is hereby incorporated by reference herein. In some embodiments, the pooled cohort equation assessment filter follows the NIPPON DATA80 absolute risk assessment charts, which incorporate the gender of the subject, the age of the subject, the total cholesterol level of the subject, the systolic blood pressure of the subject, and a smoking status of the subject, as set forth in Teramoto et al., Supra. In some embodiments, the pooled cohort equation also incorporates a glucose level of the subject.

In some embodiments, using the NIPPON DATA80 guidance, the risk for the coronary artery death used in calculating the pooled cohort equation is a 10-year risk, and a first threshold value, e.g., a threshold value which when the risk of the subject is determined to be less than fires the filter, is a 0.5% risk. In some embodiments, the risk for the fatal cardiovascular disease used in calculating the pooled cohort equation is a 10-year risk, and the first threshold value is a 1% risk. In some embodiments, the risk for the fatal cardiovascular disease used in calculating the pooled cohort equation is a 10-year risk, and the first threshold value is a 2% risk. In other embodiments, the risk for the fatal cardiovascular disease used in calculating the pooled cohort equation is a 10-year risk, and the first threshold value is a 3%, 4%, or 5% risk.

In some embodiments, the pooled cohort equation used to calculate a risk of atherosclerotic cardiovascular disease for the pooled cohort equation assessment filter is calculated using the guidelines set forth in Yang X. et al., Predicting the 10-Year Risks of Atherosclerotic Cardiovascular Disease in Chinese Population: The China-PAR Project (Prediction for ASCVD Risk in China). Circulation. 2016 Nov. 8; 134(19):1430-1440, which is hereby incorporated by reference herein. In some embodiments, the pooled cohort equation assessment filter follows the China-PAR gender specific equations, which incorporate the gender of the subject (e.g., to determine which equation to use), the age of the subject, the systolic blood pressure of the subject, a blood pressure treatment status of the subject, the total cholesterol level of the subject, a smoking status of the subject, a diabetes mellitus status of the subject, the waist circumference of the subject, a geographic residential-region of the subject (e.g., for Chinese residents only, either northern China or southern China), an urbanization residential-region of the subject (e.g., for men residing in China only, either urban or rural), and family history of atherosclerotic cardiovascular disease (e.g., for men only), as set forth in Yang X. et al., Supra and at Supplemental Information. In some embodiments, the pooled cohort equation also incorporates an HDL cholesterol level of the subject and/or a cholesterol treatment status of the subject.

In some embodiments, using the China-PAR guidance, the risk for the atherosclerotic cardiovascular disease used in calculating the pooled cohort equation is a 10-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 10-year risk, and the first threshold value is a 7.5% risk. In some embodiments, the risk for the atherosclerotic cardiovascular disease used in calculating the pooled cohort equation is a 10-year risk, and the first threshold value is a 7.5% risk.

In some embodiments, the pooled cohort equation used to calculate a risk of atherosclerotic cardiovascular disease for the pooled cohort equation assessment filter 216-5 is calculated using the guidelines set forth in National Vascular Disease Prevention Alliance, Guidelines for the management of absolute cardiovascular disease risk, 2012, which is hereby incorporated by reference herein. In some embodiments, the pooled cohort equation assessment filter follows the Australian cardiovascular risk charts, which incorporate the gender of the subject, the age of the subject, the systolic blood pressure of the subject, the ratio of total cholesterol to HDL levels of the subject, and a smoking status of the subject, as set forth in Absolute cardiovascular disease risk management: Quick reference guide for health professionals, 2012, National Stroke Foundation. In some embodiments, the pooled cohort equation also incorporates the decent of the subject (e.g., in Australia only, for Aboriginal, Tones Strait Islander, or other populations).

In some embodiments, using the Australian cardiovascular risk charts, the risk for the atherosclerotic cardiovascular disease used in calculating the pooled cohort equation is a 5-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 5-year risk, and the first threshold value is a 10% risk. In some embodiments, the risk for the atherosclerotic cardiovascular disease used in calculating the pooled cohort equation is a 5-year risk, and the first threshold value is a 16% risk. In some embodiments, the risk for the atherosclerotic cardiovascular disease used in calculating the pooled cohort equation is a 5-year risk, and the first threshold value is a 20% risk. In some embodiments, the risk for the atherosclerotic cardiovascular disease used in calculating the pooled cohort equation is a 5-year risk, and the first threshold value is a 25% risk.

In some embodiments, the pooled cohort equation used to calculate a risk of atherosclerotic cardiovascular disease for the pooled cohort equation assessment filter 216-5 is calculated using the guidelines set forth in Anderson T J et al., 2016 Canadian Cardiovascular Society Guidelines for the Management of Dyslipidemia for the Prevention of Cardiovascular Disease in the Adult, Can J Cardiol. 2016 November; 32(11):1263-1282, which is hereby incorporated by reference herein. In some embodiments, the pooled cohort equation assessment filter follows a Framingham Heart Study Risk Score equation (FRS), which incorporates the gender of the subject, the age of the subject, the systolic blood pressure of the subject, a blood pressure treatment status of the subject, the total cholesterol level of the subject, and an HDL cholesterol level of the subject, a smoking status of the subject, a diabetes mellitus status of the subject, and a CVD event incident status of the subject, as set forth in D'Agostino R B Sr et al., General cardiovascular risk profile for use in primary care: the Framingham Heart Study. Circulation. 2008 Feb. 12; 117(6):743-53, which is hereby incorporated by reference herein. In some embodiments, the pooled cohort equation assessment filter follows a modified Framingham Heart Study Risk Score equation (FRS), which incorporates the gender of the subject, the age of the subject, the systolic blood pressure of the subject, a blood pressure treatment status of the subject, the total cholesterol level of the subject, and an HDL cholesterol level of the subject, a smoking status of the subject, a diabetes mellitus status of the subject, and a CVD event incident status of the subject, and a family history status of premature cardiovascular disease, as set forth in Anderson T J et al., Supra. In some embodiments, the pooled cohort equation assessment filter follows a Cardiovascular Life Expectancy Model (CLEM), as set forth in Grover S A et al., Estimating the benefits of modifying risk factors of cardiovascular disease: a comparison of primary vs secondary prevention. Arch Intern Med. 1998 Mar. 23; 158(6):655-62, which is hereby incorporated by reference herein.

In some embodiments, using the Canadian Cardiovascular Society guidance, the risk for the atherosclerotic cardiovascular disease used in calculating the pooled cohort equation is a 10-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 10-year risk, and the first threshold value is a 10% risk. In some embodiments, the risk for the atherosclerotic cardiovascular disease used in calculating the pooled cohort equation is a 10-year risk, and the first threshold value is a 15% risk.

In some embodiments, a probability of the occurrence of a hard ASCVD event in a given period of time (e.g., within the next 10 years), e.g., as calculated above, is modified by considering one or both of the familial history of the subject for premature heart attacks or strokes and the hsCRP level of the subject. This inclusion is to reduce a likelihood of over-predicting adverse events, e.g., in subjects without a familial history of adverse events and/or with healthy hsCRP levels.

Figure 8C:
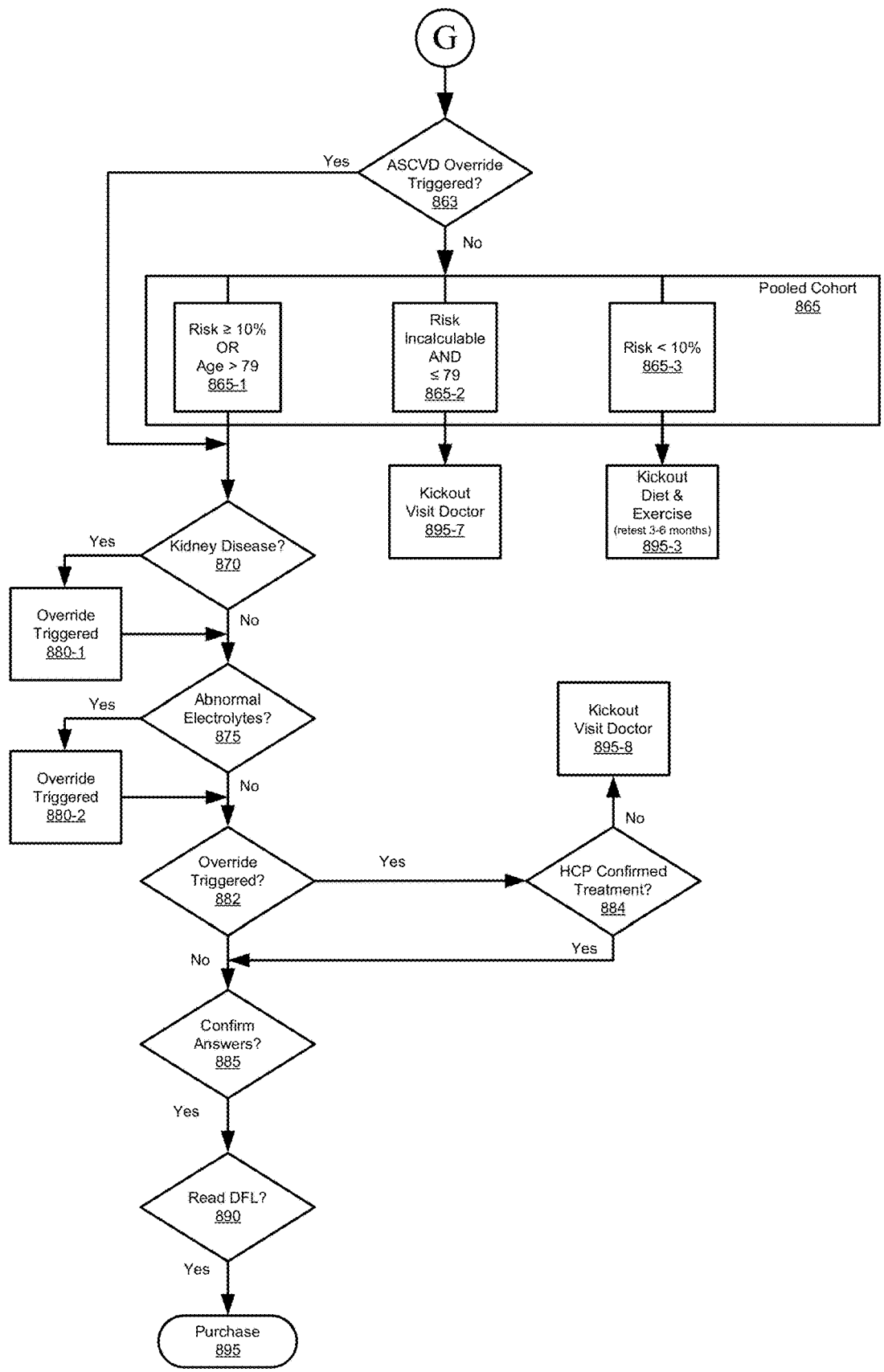

In some embodiments, e.g., when the assessment survey results indicate that the subject has a sufficient risk prior to determining a risk using a pooled cohort equation, e.g., where the subject is at least eighty years old or the subject has had an atherosclerotic cardiovascular event, the device bypasses the pooled cohort equation assessment filter (e.g., even if the plurality of assessment survey results would indicate that the subject has an ASCVD risk falling below a minimum threshold risk, or that the subject is of an age that renders calculation of an ASCVD risk impossible, the pooled cohort equation assessment filter is not fired). For example, as illustrated in FIG. 8, in response to determining that the subject has an ASCVD history (e.g., has experienced an ASCVD event or had a heart procedure) at 820 or determining that the subject is at least 80 years of age at 830, the device, optionally, generates a record of an exempting condition and then, prior to applying one or more survey results to the pooled cohort equation at 865, the device determines whether an exempting condition is present. For instance, in some embodiments if an assessment survey result indicates that the respective subject has an ASCVD history the pooled cohort equation assessment filter is bypassed (e.g., the assessment proceeds directly from 820 of FIG. 8A to 870 of FIG. 8C). In some embodiments, the exemption record is a record of one or more assessment survey results, e.g., the device pre-checks earlier recorded assessment survey results associated with ASCVD history and/or age prior to proceeding with pooled cohort equation filter 865. In some embodiments, the exemption record is a record separate from the survey result that indicates the exempting condition, and the device checks for separate records indicating the presence of an exempting condition before proceeding with pooled cohort equation filter 865.

Referring to block 460 of FIG. 4D, in some embodiments the plurality of assessment survey results further includes whether the subject is allergic to the angiotensin II receptor blocker pharmaceutical composition, and the first plurality of assessment filters includes an adverse reaction assessment filter. Accordingly, the adverse reaction assessment filter is fired when the assessment survey results indicate that the subject is allergic to the angiotensin II receptor blocker pharmaceutical composition. In some embodiments, the adverse reaction assessment filter is fired when the assessment survey results indicate that the subject has developed an adverse reaction to an angiotensin II receptor blocker pharmaceutical composition in the past. In some embodiments, the adverse reaction assessment filter is fired when the assessment survey results indicate that the subject has developed an adverse reaction to any angiotensin II receptor blocker pharmaceutical composition in the past.

Referring to block 462 of FIG. 4D, in some embodiments the plurality of assessment survey results further includes whether the subject has had a liver problem, and the first plurality of assessment filters includes a liver problem assessment filter. Accordingly, the liver problem assessment filter is fired when the assessment survey results indicate that the subject has liver disease. In some embodiments, an advanced liver disease that is capable of firing the liver problem assessment filter includes symptoms and/or conditions such as inflammation of the liver, fibrosis, cirrhosis, end-stage liver disease (ESLD), cancer of the liver, and/or liver failure. In some embodiments, a liver problem assessment filter is included in the first plurality of filters when the angiotensin II receptor blocker pharmaceutical composition includes candesartan as an active ingredient. In some embodiments, a liver problem assessment filter is included in the first plurality of filters when the angiotensin II receptor blocker pharmaceutical composition includes telmisartan as an active ingredient. In some embodiments, a liver problem assessment filter is included in the first plurality of filters when the angiotensin II receptor blocker pharmaceutical composition includes losartan as an active ingredient. In some embodiments when the liver problem assessment filter is fired, the subject is provided a recommendation to discuss taking a lower dosage of the angiotensin II receptor blocker pharmaceutical composition with a medical practitioner.

In some embodiments, rather than being implemented as a first type of filter, a liver problem assessment filter triggers a reduction in the dosage of the angiotensin II receptor blocker pharmaceutical composition that the subject can be qualified. In some embodiments, such a dosage reduction filter is included when the angiotensin II receptor blocker pharmaceutical composition includes telmisartan, losartan, or candesartan as an active ingredient.

Referring to block 464 of FIG. 4E, in some embodiments the method also includes running all or a portion of the assessment survey results against a second plurality of assessment filters of a second category class 220. When a respective assessment filter in the second plurality of assessment filters is fired, the subject is provided with a warning 226 corresponding to the respective filter (e.g., filter warning 228-4 corresponds to filter 222-4). In some embodiments, the warning 226 is provided as a next step, e.g., prior to applying assessment survey results to any subsequent filters, after the corresponding filter is fired. For example, with respect to FIG. 8C, in some embodiments, e.g., when the kidney problem assessment filter is triggered at 870, the device would provide the subject with a warning prior to proceeding to the electrolyte blood level assessment filter at 875, e.g., requiring the subject confirm they have discussed their history of kidney disease with a health care provider and the healthcare provider still recommends taking an angiotensin II receptor blocker pharmaceutical composition. In some embodiments, the warning 226 is provided after applying assessment survey results to all subsequent filters. For example, as illustrated in FIG. 8C, in some embodiments, e.g., when the kidney problem assessment filter is triggered at 870, the device would proceed to the electrolyte blood level assessment filter at 875 prior to transmitting a warning to the subject, and then transmit all warnings corresponding to filters of the second category class, at 885, after survey results have been applied to all subsequent filters.

In some embodiments, the second plurality of assessment filters 222 of the second category class 220 includes the assessment filters listed in Table 4.

TABLE 4

Example Assessment Filters of the Second Category Class

| Filter | Example Criteria |
| --- | --- |
| 1b | a kidney problem assessment filter |
| 2b | an electrolyte blood level assessment filter |
| 3b | potassium supplement assessment filter |
| 4b | colesevelam interaction assessment filter |

It is contemplated that, in some embodiments, any one or more of the filters provided in Table 4 will not be included in the second plurality of assessment filters. For example, in some embodiments, a characteristic associated with a particular survey result will be informative when qualifying a subject for one particular angiotensin II receptor blocker pharmaceutical composition but not for another angiotensin II receptor blocker pharmaceutical composition. Accordingly, it is contemplated that the second plurality of assessment filters includes any sub-set of filters provided in Table 4. Likewise, the skilled artisan may know of other assessment filters, not provided in Table 4, that may be combined with any subset of the filters provided in Table 4 to form the second plurality of assessment filters results used in the methods described herein. In one embodiment, the second plurality of assessment filters includes at least filters 1b and 2b. In one embodiment, the second plurality of assessment filters includes at least filters 1b-3b. In one embodiment, the second plurality of assessment filters includes at least filters 1b, 2b, and 4b. In one embodiment, the second plurality of assessment filters includes at least filters 1b-4b.

Referring to block 466 of FIG. 4E, in some embodiments, the second plurality of assessment filters includes a kidney problem assessment filter (e.g., kidney problem assessment filter 222-2 in FIG. 3 and/or filter 1a in Table 4). The kidney problem assessment filter is configured to be fired at least when the plurality of assessment survey results indicate that the subject has had a kidney problem. In some embodiments, the kidney problem assessment filter is configured to be fired at least when the plurality of assessment survey results indicate that the subject has been diagnosed with kidney disease. Symptoms of kidney problems include fatigue, a feeling of coldness, shortness of breath, a feeling of faintness, dizziness, weakness, a feeling of itchiness, or swelling of the hands and feet. When the kidney problem assessment filter is fired, the device transmits a warning corresponding to the kidney problem assessment filter, and requires the user to acknowledge the warning before authorizing a provision of the angiotensin II receptor blocker pharmaceutical composition. In some embodiments, e.g., where the angiotensin II receptor blocker includes eprosartan or olmesartan as an active ingredient, the kidney problem assessment filter is implemented as a first category class assessment filter (e.g., the subject is deemed not qualified for the angiotensin II receptor blocker when the filter is fired), rather than a second category class assessment filter.

Referring to block 468 of FIG. 4E, in some embodiments the second plurality of assessment filters includes an electrolyte blood level assessment filter (e.g., electrolyte blood level assessment filter 222-2 in FIG. 3 and/or filter 2a in Table 4). The electrolyte blood level assessment filter is configured to be fired at least when the plurality of assessment survey results indicate that the subject has had an abnormal electrolyte blood level. In some embodiments, the kidney problem assessment filter is configured to be fired at least when the plurality of assessment survey results indicate that the subject has been diagnosed with an abnormal electrolyte blood level. In some embodiments, an abnormal electrolyte blood level is a value that is outside of a range of 4.5-5.5 mEq/L of calcium, a range of 97-107 mEq/L of chloride, a range of 3.5-5.3 mEq/L potassium, a range of 1.5-2.5 mEq/L magnesium, and/or a range of 136-145 mEq/L sodium. Symptoms of abnormal electrolyte blood levels include irregular heartbeat, confusion, blood pressure changes, nervous system and/or bone disorders, weakness and/or twitching of the muscles, numbness, fatigue, irregular heartbeat, and/or blood pressure changes. When the electrolyte blood level assessment filter is fired, the device transmits a warning corresponding to the electrolyte blood level assessment filter, and requires the user to acknowledge the warning before authorizing a provision of the angiotensin II receptor blocker pharmaceutical composition.

Referring to block 470 of FIG. 4E, in some embodiments the plurality of assessment survey results further includes whether the subject has taking a potassium supplement or a salt substitute that includes potassium, and the second plurality of assessment filters includes a potassium supplement assessment filter. For instance, in some embodiments, a potassium supplement assessment filter is included when the angiotensin II receptor blocker pharmaceutical composition includes irbesartan or losartan as an active ingredient. Accordingly, the potassium supplement assessment filter is configured to be fired at least when the plurality of assessment survey results indicates that the subject is taking a potassium supplement or a salt substitute that includes potassium. When the potassium supplement assessment filter is fired, the device transmits a warning corresponding to the potassium supplement assessment filter, and requires the user to acknowledge the warning before authorizing a provision of the angiotensin II receptor blocker pharmaceutical composition Referring to block 474 of FIG. 4E, in some embodiments the plurality of assessment survey results further includes whether the subject is taking colesevelam, and the second plurality of assessment filters includes a colesevelam interaction assessment filter. When the colesevelam interaction assessment filter is fired, the device transmits a warning corresponding to the colesevelam interaction assessment filter, and requires the user to acknowledge the warning before authorizing a provision of the angiotensin II receptor blocker pharmaceutical composition. In some embodiments, a colesevelam interaction assessment filter is included in the second plurality of filters when the angiotensin II receptor blocker pharmaceutical composition includes olmesartan as an active ingredient.

In some embodiments, as described above, the second plurality of assessment filters includes a liver problem assessment filter (e.g., the liver problem assessment filter is a second category class filter). For instance, in some embodiments the angiotensin II receptor blocker pharmaceutical composition includes candesartan, losartan, or telmisartan and the liver problem assessment filter is included in the second plurality of assessment filters. Accordingly, when the liver problem assessment filter is fired, the device transmits a warning corresponding to the liver problem assessment filter, and requires the user to acknowledge the warning before authorizing a provision of the angiotensin II receptor blocker pharmaceutical composition. In some embodiments, the warning is a recommendation, and/or prompt to discuss with a medical practitioner, to take a reduced dosage of the angiotensin II receptor blocker (e.g., half a recommended dosage).

Referring to block 476 of FIG. 4E, in some embodiments the warning 226 corresponding to a respective filter 222 in the second plurality of assessment filters includes a prompt for the subject to indicate whether they have discussed the risk factor underlying the respective filter in the second plurality of assessment filters that was fired with a health care practitioner (e.g., a licensed medical practitioner), e.g., and the health care practitioner indicated that the subject should take an angiotensin II receptor blocker pharmaceutical composition in view of the underlying risk factor. Accordingly, acknowledgement is obtained from the subject when the subject indicates that they have discussed the risk factor underlying the respective filter in the second plurality of assessment filters that was fired with a health care provider. For example, message 702 in FIG. 7 illustrates a warning that is generic to any fired filters. In some embodiments, the warning is specific to a particular filter (e.g., filter warning 226 in FIG. 2), e.g., communicating to the user why the respective filter was fired.

In some embodiments, an acknowledgment from the user is verified by the health care practitioner (e.g., the method requires verification in order for authorization of the provision of the angiotensin II receptor blocker pharmaceutical composition), e.g., in order to verify an accuracy of the assessment survey results of the subject. In some embodiments, e.g., when the acknowledgment is verified by the heath care practitioner, the subject is deemed a trusted subject, such that verification of future results is not required.

Referring to block 478 of FIG. 4E, the method includes obtaining acknowledgment from the subject for any warning 226 issued to the subject by any filter 222 in the second plurality of assessment filters. If a filter 216 in the first plurality of assessment filters fires, the subject is denied access to the over-the-counter angiotensin II receptor blocker pharmaceutical composition.

Blocks 480 through 488.

Referring to block 480 of FIG. 4F, the process control proceeds to the fulfillment process when no filter 216 in the first plurality of assessment filters has been fired and the subject has acknowledged each warning 226 associated with each filter 222 in the second plurality of assessment filters that was fired. In some embodiments, the fulfillment process includes storing an indication in a user profile 234 of an initial order date and/or destination for the angiotensin II receptor blocker pharmaceutical composition. The initial order date is utilized, for example, to verify at least a refill status of a provision of the angiotensin II receptor blocker. The initial order date is also utilized, for example, to verify at least an elapsed period of time between an initial order and a future re-order. Such verification is required in order to ensure that certain tests (e.g., blood pressure tests) are taken regularly.

The fulfillment process further includes communicating an over-the-counter drug facts label 230 for the angiotensin II receptor blocker pharmaceutical composition to the subject. In some embodiments, the drug facts label 230 is communicated to the subject in real-time, e.g., within the same user interface as used for the qualification assessment process. In some embodiments, the over-the-counter drug facts label 230 specifies what the angiotensin II receptor blocker pharmaceutical composition is for (e.g., to lower blood pressure, to treat heart disease, etc.) and any risks associated with taking the angiotensin II receptor blocker pharmaceutical composition (e.g., drug-drug interactions, pharmacokinetic interactions, adverse reactions, etc.). For instance, in some embodiments, upon confirmation from the subject that the over the counter drug facts label 230 has been received and read, the subject is authorized for provision of a dosage of from 4 mg to 600 mg of angiotensin II receptor blocker no more than once per day. In some embodiments, the subject is authorized for a provision of a dosage of from 40 mg to 80 mg of angiotensin II receptor blocker (e.g., azilsartan) no more than once per day (block 484). In some embodiments, the subject is authorized for a provision of a dosage of from 8 mg to 16 mg of angiotensin II receptor blocker (e.g., candesartan) no more than once per day. In some embodiments, the subject is authorized for a provision of a dosage of from 80 mg to 160 mg of angiotensin II receptor blocker (e.g., valsartan) no more than once per day. In some embodiments, the subject is authorized for a provision of a dosage of from 20 mg to 40 mg of angiotensin II receptor blocker (e.g., olmesartan, telmisartan, etc.) no more than once per day. In some embodiments, the subject is authorized for a provision of a dosage of from 400 mg to 600 mg of angiotensin II receptor blocker (e.g., eprosartan) no more than once per day. In some embodiments, the subject is authorized for a provision of a dosage of from 25 mg to 50 mg of angiotensin II receptor blocker (e.g., losartan) no more than once per day. In some embodiments, the subject is authorized for a provision of a dosage of from 150 mg to 300 mg of angiotensin II receptor blocker (e.g., irbesartan) no more than once per day.

In some embodiments, upon confirmation from the subject that the over the counter drug facts label has been received and read, the subject is authorized for provision of a dosage of from 20 mg to 100 mg of azilsartan no more than once per day. In some embodiments, upon confirmation from the subject that the over the counter drug facts label has been received and read, the subject is authorized for provision of a dosage of from 40 mg to 80 mg of azilsartan no more than once per day. In some embodiments, upon confirmation from the subject that the over the counter drug facts label has been received and read, the subject is authorized for provision of a dosage of 40 mg of azilsartan no more than once per day. In some embodiments, upon confirmation from the subject that the over the counter drug facts label has been received and read, the subject is authorized for provision of a dosage of 80 mg of azilsartan no more than once per day. In some embodiments, the angiotensin II receptor blocker pharmaceutical composition includes azilsartan medoxomil.

In some embodiments, upon confirmation from the subject that the over the counter drug facts label has been received and read, the subject is authorized for provision of a dosage of from 4 mg to 32 mg of candesartan no more than once per day. In some embodiments, upon confirmation from the subject that the over the counter drug facts label has been received and read, the subject is authorized for provision of a dosage of from 8 mg to 16 mg of candesartan no more than once per day. In some embodiments, upon confirmation from the subject that the over the counter drug facts label has been received and read, the subject is authorized for provision of a dosage of 8 mg of candesartan no more than once per day. In some embodiments, upon confirmation from the subject that the over the counter drug facts label has been received and read, the subject is authorized for provision of a dosage of 16 mg of candesartan no more than once per day.

In some embodiments, upon confirmation from the subject that the over the counter drug facts label has been received and read, the subject is authorized for provision of a dosage of from 40 mg to 320 mg of valsartan no more than once per day. In some embodiments, upon confirmation from the subject that the over the counter drug facts label has been received and read, the subject is authorized for provision of a dosage of from 80 mg to 160 mg of valsartan no more than once per day. In some embodiments, upon confirmation from the subject that the over the counter drug facts label has been received and read, the subject is authorized for provision of a dosage of 80 mg of valsartan no more than once per day. In some embodiments, upon confirmation from the subject that the over the counter drug facts label has been received and read, the subject is authorized for provision of a dosage of 160 mg of valsartan no more than once per day.

In some embodiments, upon confirmation from the subject that the over the counter drug facts label has been received and read, the subject is authorized for provision of a dosage of from 20 mg to 80 mg of telmisartan no more than once per day. In some embodiments, upon confirmation from the subject that the over the counter drug facts label has been received and read, the subject is authorized for provision of a dosage of from 20 mg to 40 mg of telmisartan no more than once per day. In some embodiments, upon confirmation from the subject that the over the counter drug facts label has been received and read, the subject is authorized for provision of a dosage of 20 mg of telmisartan no more than once per day. In some embodiments, upon confirmation from the subject that the over the counter drug facts label has been received and read, the subject is authorized for provision of a dosage of 40 mg of telmisartan no more than once per day.

In some embodiments, upon confirmation from the subject that the over the counter drug facts label has been received and read, the subject is authorized for provision of a dosage of from 400 mg to 600 mg of eprosartan no more than once per day. In some embodiments, upon confirmation from the subject that the over the counter drug facts label has been received and read, the subject is authorized for provision of a dosage of 400 mg of eprosartan no more than once per day. In some embodiments, upon confirmation from the subject that the over the counter drug facts label has been received and read, the subject is authorized for provision of a dosage of 600 mg of eprosartan no more than once per day.

In some embodiments, upon confirmation from the subject that the over the counter drug facts label has been received and read, the subject is authorized for provision of a dosage of from 5 mg to 40 mg of olmesartan no more than once per day. In some embodiments, upon confirmation from the subject that the over the counter drug facts label has been received and read, the subject is authorized for provision of a dosage of from 20 mg to 40 mg of olmesartan no more than once per day. In some embodiments, upon confirmation from the subject that the over the counter drug facts label has been received and read, the subject is authorized for provision of a dosage of 20 mg of olmesartan no more than once per day. In some embodiments, upon confirmation from the subject that the over the counter drug facts label has been received and read, the subject is authorized for provision of a dosage of 40 mg of olmesartan no more than once per day.

In some embodiments, upon confirmation from the subject that the over the counter drug facts label has been received and read, the subject is authorized for provision of a dosage of from 25 mg to 100 mg of losartan no more than once per day. In some embodiments, upon confirmation from the subject that the over the counter drug facts label has been received and read, the subject is authorized for provision of a dosage of from 25 mg to 50 mg of losartan no more than once per day. In some embodiments, upon confirmation from the subject that the over the counter drug facts label has been received and read, the subject is authorized for provision of a dosage of 25 mg of losartan no more than once per day. In some embodiments, upon confirmation from the subject that the over the counter drug facts label has been received and read, the subject is authorized for provision of a dosage of 50 mg of losartan no more than once per day.

Furthermore, in some embodiments upon confirmation from the subject that the over the counter drug facts label has been received and read, the subject is authorized for provision of a dosage of from 75 mg to 300 mg of irbesartan no more than once per day. In some embodiments, upon confirmation from the subject that the over the counter drug facts label has been received and read, the subject is authorized for provision of a dosage of from 150 mg to 300 mg of irbesartan no more than once per day. In some embodiments, upon confirmation from the subject that the over the counter drug facts label has been received and read, the subject is authorized for provision of a dosage of 150 mg of irbesartan no more than once per day. In some embodiments, upon confirmation from the subject that the over the counter drug facts label has been received and read, the subject is authorized for provision of a dosage of 300 mg of irbesartan no more than once per day.

Referring to block 482 of FIG. 4F, in some embodiments the fulfillment process further includes authorizing provision of the angiotensin II receptor blocker pharmaceutical composition to the subject. The authorization occurs upon confirmation from the subject that the over-the-counter drug facts label 230 has been received and read by the subject. In some embodiments, this authorization includes a destination associated with the subject. In some embodiments, the destination associated with the subject is stored in the user profile 234 (block 486). In some embodiments, the destination associated with the subject is a physical address including a street address, a Post Office box, a pharmacy associated with the subject, a health care provider associated with the subject, and/or one or more coordinates (e.g., longitude, latitude, elevation). In some embodiments, the provision of the angiotensin II receptor blocker pharmaceutical composition to the subject includes shipping the angiotensin II receptor blocker pharmaceutical composition to the physical address associated with the subject (block 488). In some embodiments, the provision of the angiotensin II receptor blocker pharmaceutical composition to the subject includes shipping the angiotensin II receptor blocker pharmaceutical composition to a pharmacy associated and/or a location associated with a health care provider of the subject and/or an office of a medical practitioner associated with the subject.

Blocks 500 Through 506.

Referring to block 502 of FIG. 5A, a goal of the present disclosure is to qualify subjects (e.g., a re-fulfillment process) for over-the-counter delivery of an angiotensin II receptor blocker pharmaceutical composition to lower blood pressure, e.g., thereby, treating and/or preventing heart disease, using a computer system such as an angiotensin II receptor blocker pharmaceutical composition OTC dispensing device 250. As illustrated in FIG. 2, the angiotensin II receptor blocker pharmaceutical composition OTC dispensing device (e.g., device 250) includes one or more processors (e.g., processor 274) and a memory (e.g., memory 192 and/or 290). The memory stores non-transitory instructions that, when executed by the one or more processors, perform a method. In some embodiments, the present disclosure provides a method for qualifying a subject for a reorder (e.g., a reassessment) of an angiotensin II receptor blocker pharmaceutical composition. In some embodiments, the qualification for a reorder of the angiotensin II receptor blocker pharmaceutical composition follows an initial qualification (e.g., an assessment) of the subject, as described herein. In some embodiments, the qualification for a refill of the angiotensin II receptor blocker pharmaceutical composition follows issuance of a prescription to the subject for the angiotensin II receptor blocker pharmaceutical composition. For example, in some embodiments, a subject who is new to the qualification process is asked whether they previously received a prescription for the angiotensin II receptor blocker pharmaceutical composition. Accordingly, if the subject indicates that they have not previously received a prescription, the subject is directed to an initial qualification method and, if the subject indicates that they have previously received a prescription, the subject is directed to the refill qualification method, e.g., as described below.

In some embodiments a re-fulfillment procedure is performed. The re-fulfillment procedure is responsive to receiving a re-order request from the subject for the angiotensin II receptor blocker pharmaceutical composition. In some embodiments, a prompt to initiate the re-fulfillment procedure is sent to user device 102 associated with the subject after a predetermined amount of time associated with a duration of dosages previously delivered to the subject (e.g., the user is reminded to fulfill their order of the angiotensin II receptor blocker pharmaceutical composition just before, or just after, the user is scheduled to run out of a previously delivered provision.

In some embodiments the angiotensin II receptor blocker pharmaceutical composition includes one of candesartan, eprosartan, irbesartan, losartan, olmesartan, telmisartan, or valsartan. These angiotensin II receptor blocker compositions are described in Farnham et al., 2000, "Angiotensin II receptor antagonists," The Lancet, 335(9204), pg. 594, the content of which is hereby incorporated by reference. in some embodiments, the lowering of blood pressure is to treat and/or prevent heart disease.

Referring to blocks 508 and 510 of FIG. 5A, in some embodiments the re-fulfillment procedure includes conducting a reassessment survey of the subject. The reassessment survey is configured to obtain a plurality of reassessment survey results. These results are derived from corresponding reassessment survey questions (e.g., the device 250 transmits one or more reassessment survey questions to the user, prompting a response, and then receives a response to the one or more reassessment survey questions back from the subject). In some embodiments, the plurality of reassessment survey results includes some or all of the characteristics listed in Table 5. For example, in some embodiments, the plurality of reassessment survey results includes 1, 2, 3, 4, 5, 6, or all 7 of the characteristic listed in Table 5. In one embodiment, the reassessment survey questions and results include at least characteristics 1-6 as provided in Table 5. In one embodiment, the reassessment survey questions and results include at least characteristics 2-6 as provided in Table 5.

In some embodiments, the reassessment survey results includes at least one of: a systolic blood pressure and/or a diastolic blood pressure of the subject (e.g., responsive to a reassessment survey question that is associated with and/or applied to (905, 910) a blood pressure reassessment survey filter of a first category class 214-6), whether the subject is one of pregnant, breastfeeding, or planning to become pregnant (e.g., responsive to a reassessment survey question that is associated with and/or applied to (915) a pregnancy reassessment filter of a first category class 214-7), whether the subject has started taking a medication that interacts with the angiotensin II receptor blocker pharmaceutical composition since receiving their last provision of the angiotensin II receptor blocker pharmaceutical composition (e.g., responsive to a survey question that is associated with and/or applied to (920, 925, 930) a drug interaction reassessment filter of a first category class 216-8), whether the subject has experienced symptoms of hypotension since receiving their last provision of the angiotensin II receptor blocker pharmaceutical composition (e.g., responsive to a reassessment survey question that is associated with and/or applied to (940) a hypotension reassessment filter of a first category class 916-9), whether the subject has developed an abnormal electrolyte blood level since receiving their last provision of the angiotensin II receptor blocker pharmaceutical composition (e.g., responsive to a reassessment survey question that is associated with and/or applied to (945) an electrolyte blood level reassessment filter 216-10 of a first category class), and whether the subject has developed a kidney problem since receiving their last provision of the angiotensin II receptor blocker pharmaceutical composition (e.g., responsive to a survey question that is associated with and/or applied to (850) a kidney problem reassessment filter of a first category class 216-11).

In some embodiments, the reassessment survey includes questions that elicit responses providing some or all of the characteristics listed in Table 5. In some embodiments, the reassessment survey includes questions corresponding to each of the survey results required for the methods described herein. In other embodiments, the reassessment survey includes questions corresponding to only a subset of the reassessment survey results required for the methods described herein. In such embodiments, other reassessment survey results required for the methods described herein are acquired through other means (e.g., upon registration/subscription for a service associated with qualifying the subject for over-the-counter medication, from a healthcare provider, from a prior survey, from a database associated with a pharmacy, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a last cholesterol or blood pressure measurement determined for the subject).

TABLE 5

Example Medical Information Elicited from Reassessment Survey Questions

| Result | Exemplary Characteristics |
|---|---|
| 1 | a blood pressure of the subject, |
| 2 | whether the subject is one of (i) pregnant, (ii) breastfeeding, or (iii) planning to become pregnant |

TABLE 5-continued

Example Medical Information Elicited from Reassessment Survey Questions

| Result | Exemplary Characteristics |
|---|---|
| 3 | whether the subject has started taking a medication that interacts with the angiotensin II receptor blocker pharmaceutical composition since receiving their last provision of the angiotensin II receptor blocker pharmaceutical composition |
| 4 | whether the subject has experienced symptoms of hypotension since receiving their last provision of the angiotensin II receptor blocker pharmaceutical composition |
| 5 | whether the subject has developed an abnormal electrolyte blood level since receiving their last provision of the angiotensin II receptor blocker pharmaceutical composition |
| 6 | whether the subject has developed a kidney problem since receiving their last provision of the angiotensin II receptor blocker pharmaceutical composition |
| 7 | whether the subject has developed a side effect associated with the angiotensin II receptor blocker since receiving their last provision of the angiotensin II receptor blocker pharmaceutical composition |

It is contemplated that, in some embodiments, any one or more of the survey questions provided in Table 5 will not be included in the reassessment survey (e.g., will not be used for the reassessment). For example, in some embodiments, a characteristic associated with a particular survey questions will be informative when qualifying a subject for one particular angiotensin II receptor blocker but not for another angiotensin II receptor blocker. For instance, a reassessment survey question is queried for azilsartan qualifying reassessment surveys but not for olmesartan qualifying reassessment surveys. The skilled artisan will recognize that different angiotensin II receptor blockers carry different risk and drug interaction profiles. Accordingly, survey information required for qualifying a subject for access to one angiotensin II receptor blocker with a known adverse drug interaction may not be necessary for qualifying the same subject for access to a second angiotensin II receptor blocker.

Accordingly, it is contemplated that the reassessment survey questions elicit responses to any sub-set of survey results provided in Table 5. For brevity, all possible combinations of the characteristics provided in Table 5 are not specifically delineated here. However, the skilled artisan will easily be able to envision any particular subset of survey questions designed to elicit responses to any subset of characteristics provided in Table 5. Likewise, the skilled artisan may know of other survey questions, not provided in Table 5, that may be combined with any subset of the survey questions provided in Table 5 to form the reassessment survey questions used in the methods described herein.

Referring to block 512 of FIG. 5A, all or a portion the reassessment results are run against a first plurality of reassessment filters of the first category class 214-2. When a respective reassessment filter in the first plurality of reassessment filters is fired (e.g., when a reassessment survey result indicates that a triggering condition 218 has been met), the subject is deemed not qualified for the angiotensin II receptor blocker pharmaceutical composition and the method is terminated without delivery of the angiotensin II receptor blocker pharmaceutical composition.

Referring to blocks 514 through 532 of FIGS. 5A and 5B, specific filters in the first plurality of reassessment filters and their exemplary triggering conditions that cause the corresponding filter to fire are detailed.

In some embodiments, the first plurality of reassessment filters of the first category class includes some or all of the filters listed in Table 6. For example, in some embodiments, the first plurality of reassessment filters includes 1, 2, 3, 4, 5, or all 6 of the filters listed in Table 6.

TABLE 6

Exemplary Third Plurality of Filters of the First Category Class

| Filter | Exemplary Criteria |
|---|---|
| 1c | a blood pressure reassessment filter |
| 2c | a pregnancy reassessment filter |
| 3c | a drug interaction reassessment filter |
| 4c | a hypotension reassessment filter |
| 5c | an electrolyte blood level reassessment filter |
| 6c | a kidney problem reassessment filter |

It is contemplated that, in some embodiments, any one or more of the filters provided in Table 6 will not be included in the first plurality of reassessment filters. For example, in some embodiments, a characteristic associated with a particular reassessment survey result will be informative when qualifying a subject for one particular angiotensin II receptor blocker but not for another angiotensin II receptor blocker. Likewise, the skilled artisan may know of other filters, not provided in Table 6, which may be combined with any subset of the assessment filters provided in Table 2 to form the first plurality of reassessment filters results used in the methods described herein. For brevity, all possible combinations of the reassessment filters provided in Table 6 are not specifically delineated here. In one embodiment, the first plurality of reassessment filters includes all of filters 1c-6c as provided in Table 6. In one embodiment, the first plurality of reassessment filters includes filters 2c-6c as provided in Table 6.

It is contemplated that, in some embodiments, any one or more of the filters provided in Table 6 will not be included in the first plurality of reassessment filters. For example, in some embodiments, a characteristic associated with a particular reassessment survey result will be informative when qualifying a subject for one particular angiotensin II receptor blocker but not for another angiotensin II receptor blocker. Likewise, the skilled artisan may know of other filters, not provided in Table 6, which may be combined with any subset of the assessment filters provided in Table 2 to form the first plurality of reassessment filters results used in the methods described herein. For brevity, all possible combinations of the reassessment filters provided in Table 6 are not specifically delineated here.

Referring to block 514 of FIG. 5A, in some embodiments the first plurality of reassessment filters includes a blood pressure reassessment filter 216-6. In some embodiments, the blood pressure reassessment filter is as described above in relation to the blood pressure assessment filter 216-2. In some embodiments, the blood pressure reassessment filter is configured to be fired at least when the plurality of reassessment survey results indicates that the subject has hypertension. In some embodiments, the reassessment survey results indicate that the subject has hypertension (e.g., an indication of stage 1 hypertension) if the subject has a systolic blood pressure of greater than or equal to 130 mm Hg and/or a diastolic blood pressure of greater than or equal to 80 mm Hg.

Referring to block 516 and 518 of FIG. 5A, in some embodiments the first plurality of reassessment filters includes a pregnancy reassessment filter 2016-7. In some embodiments, the pregnancy reassessment filter is as described above in relation to the pregnancy assessment filter 216-1. In some embodiments, the pregnancy reassessment filter is configured to be fired at least when the plurality of reassessment survey results indicates that the subject is pregnant or the subject is breastfeeding. In some embodiments, the pregnancy reassessment filter is also configured to be fired when the subject is planning on becoming pregnant. When the pregnancy reassessment filter is fired, the subject is not permitted to obtain the angiotensin II receptor blocker pharmaceutical composition over-the-counter (e.g., the method is terminated without authorizing re-provision of the angiotensin II receptor blocker pharmaceutical composition to the subject).

Referring to block 520 through 526 of FIG. 5B, in some embodiments, the first plurality of reassessment filters includes a drug interaction reassessment filter 2016-8. In some embodiments, the drug interaction reassessment filter is as described above in relation to the drug interaction assessment filter 226-3. In some embodiments, the drug interaction reassessment filter is configured to be fired at least when the plurality of reassessment survey results indicates that the subject is taking (e.g., has started taking) a medication that interacts with the angiotensin II receptor blocker pharmaceutical composition. As previously described, these interactions can be pharmacodynamic drug-drug interactions or pharmacokinetic drug-drug interactions. Typically, the interactions (e.g., triggering conditions 224) that are capable of firing the drug interaction reassessment filter are the same as the interactions that are capable of firing the drug interaction assessment filter assuming that the angiotensin II receptor blocker pharmaceutical composition is the same between the fulfillment process and the re-fulfillment process. For instance, in some embodiments the drug interaction reassessment filter is fired when the plurality of reassessment survey results indicates that the subject is taking a lithium medication. In some embodiments, the drug interaction reassessment filter is fired when the plurality of reassessment survey results indicates that the subject is taking a non-steroidal anti-inflammatory medication. In some embodiments, the drug interaction reassessment filter is fired when the plurality of reassessment survey results indicates that the subject is taking a blood pressure medication (e.g., a medication for high blood pressure).

Referring to block 528 of FIG. 5B, in some embodiments, the first plurality of reassessment filters of the first category class 214-2 includes a hypotension reassessment filter. In some embodiments, the hypotension reassessment filter is configured to be fired at least when the reassessment survey results indicate that the subject has experienced hypotension (e.g., a systolic blood pressure of less than or equal to 90 mm Hg or a diastolic blood pressure of less than or equal to 60 mm Hg) since receiving their last provision of the angiotensin II receptor blocker pharmaceutical composition. In some embodiments, e.g., when the plurality of reassessment survey results indicate that the subject has experienced symptoms of hypotension, the device fires the hypotension reassessment filter and transmits, to the subject, advice to visit a doctor. In some embodiments, rather than being implemented as a first class of filter, the hypotension reassessment filter is implemented as a second class of filter, e.g., where firing of the filter requires the subject confirm they have discussed the risks of hypotension with a physician prior to being qualified for a re-order of the angiotensin II receptor blocker pharmaceutical composition.

Referring to block 530 of FIG. 5B, in some embodiments the first plurality of reassessment filters of the first category class includes an electrolyte blood level reassessment filter. In some embodiments, the electrolyte blood level reassessment filter is as described above with respect to the electrolyte blood level assessment filter. In some embodiments, the electrolyte blood level reassessment filter is configured to be fired at least when the plurality of reassessment survey results indicates that the subject has developed an abnormal electrolyte blood level since receiving their last provision of the angiotensin II receptor blocker pharmaceutical composition. In some embodiments, rather than being implemented as a first class of filter, the electrolyte blood level reassessment filter is implemented as a second class of filter, e.g., where firing of the filter requires the subject confirm they have discussed the risks of abnormal electrolyte blood levels with a physician prior to being qualified for a re-order of the angiotensin II receptor blocker pharmaceutical composition.

Referring to block 532 of FIG. 5B, in some embodiments the first plurality of reassessment filters of the first category class includes a kidney problem reassessment filter. In some embodiments, the kidney problem reassessment filter is as described above with respect to the kidney problem assessment filter. In some embodiments, the kidney problem reassessment filter is configured to be fired at least when the plurality of reassessment survey results indicates that the subject has developed a kidney problem since receiving their last provision of the angiotensin II receptor blocker pharmaceutical composition. In some embodiments, rather than being implemented as a first class of filter, the kidney problem reassessment filter is implemented as a second class of filter, e.g., where firing of the filter requires the subject confirm they have discussed the risks of kidney problems with a physician prior to being qualified for a re-order of the angiotensin II receptor blocker pharmaceutical composition.

Figure 9A:
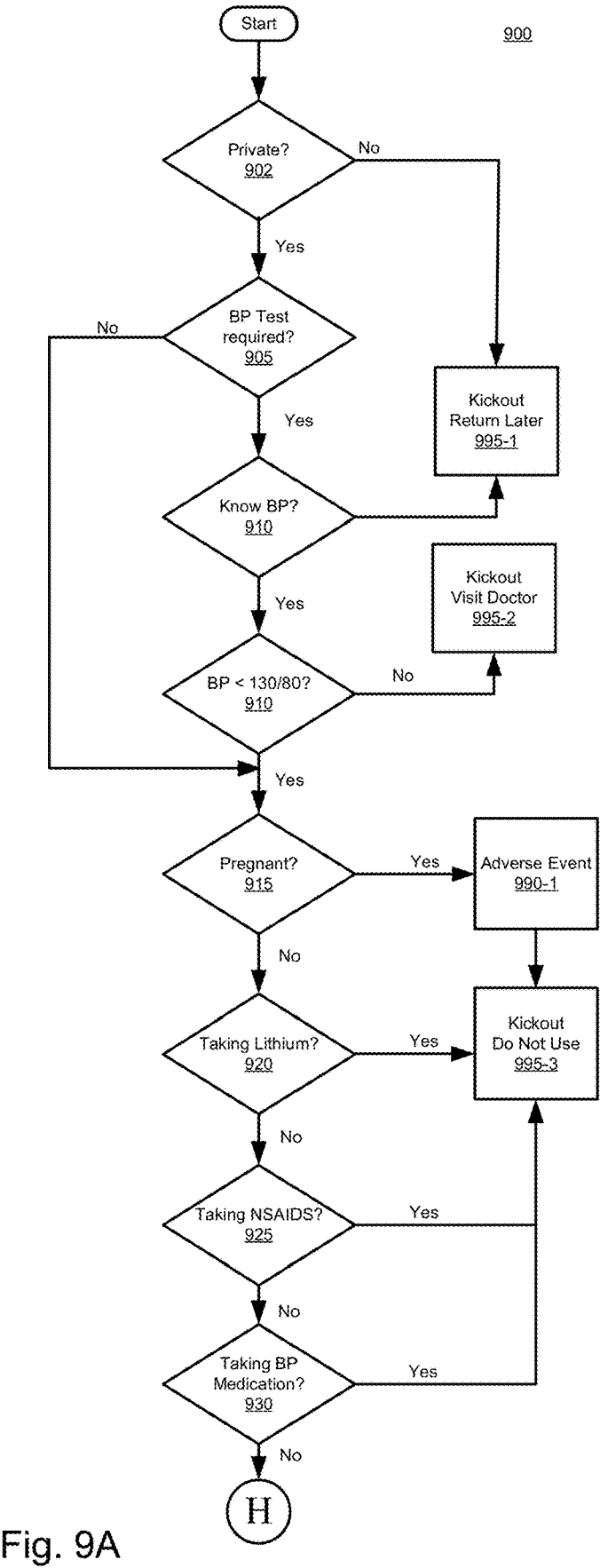
FIGS. 9A and 9B collectively illustrate an example method for qualifying a subject for a refill of an over-the-counter provision of an angiotensin II receptor blocker pharmaceutical composition, in accordance with an embodiment of the present disclosure.
Figure 9B:
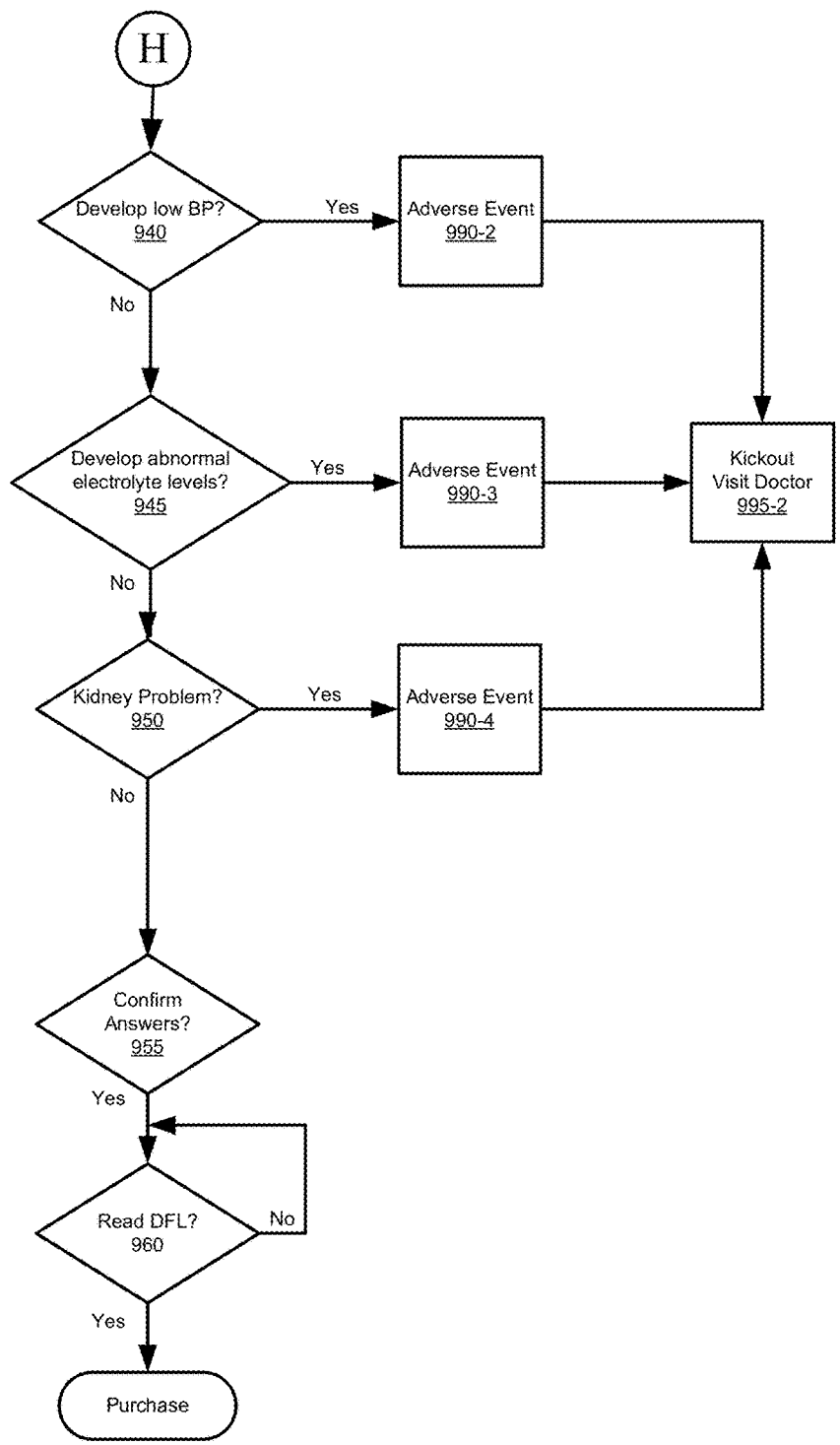

Referring to block 534 of FIG. 5C, in some embodiments the method also includes running all or a portion of the reassessment survey results against a second plurality of reassessment filters of the second category class 220-2. When a respective filter in the second plurality of reassessment filters is fired, the subject is provided with a warning corresponding to the respective filter. In some embodiments, the warning is provided as a next step, e.g., prior to applying reassessment survey results to any subsequent filters, after the corresponding filter is fired. For example, with respect to FIGS. 9A and 9B, in some embodiments, the device would provide the subject with a warning prior to proceeding to the proceeding filter, e.g., requiring the subject confirm they have discussed warning with a health care provider and the healthcare provider still recommends taking an angiotensin II receptor blocker pharmaceutical composition. In some embodiments, the warning is provided after applying reassessment survey results to all subsequent filters.

Referring to block 498, in some embodiments the second plurality of reassessment filters includes one or more of an impaired renal function reassessment filter, an abnormal potassium serum level reassessment filter, and a side effect reassessment filter.

In some embodiments, the second plurality of reassessment filters of the second category class 220-2 includes some or all of the filters listed in Table 7. For example, in some embodiments, the second plurality of reassessment filters includes 1, 2, or all 3 of the filters listed in Table 7.

TABLE 7

Example Reassessment Filters of the Second Category Class

| Filter | Exemplary Criteria |
|---|---|
| 1a | a renal function reassessment filter |
| 2a | a potassium serum level reassessment filter |
| 3a | a side effects reassessment filter |

It is contemplated that, in some embodiments, any one or more of the filters provided in Table 7 will not be included in the second plurality of reassessment filters. For example, in some embodiments, a characteristic associated with a particular survey result will be informative when qualifying a subject for one particular angiotensin II receptor blocker pharmaceutical composition but not for another angiotensin II receptor blocker pharmaceutical composition. Accordingly, it is contemplated that the second plurality of reassessment filters includes any sub-set of filters provided in Table 7. Likewise, the skilled artisan may know of other filters, not provided in Table 7, that may be combined with any subset of the filters 222 provided in Table 7 to form the fourth plurality of filters results used in the methods described herein. In some embodiments, no reassessment filters of the second category class are included in the re-order method. In one the embodiments, one or more of filters 1d-3d, as provided in Table 7, are included in a second plurality of reassessment filters, applied to information obtained by the reassessment survey.

Referring to block 536 of FIG. 5C, in some embodiments the reassessment survey results further includes whether the subject has experienced an impaired renal function since receiving their last provision of the angiotensin II receptor blocker pharmaceutical composition. Accordingly, in some embodiments the second plurality of reassessment filters includes a renal function reassessment filter that is fired at least when the plurality of reassessment results indicates that the subject has experienced, since receiving their last provision of the angiotensin II receptor blocker pharmaceutical composition, an impaired renal function.

Referring to block 538 of FIG. 5C, in some embodiments the reassessment survey results further includes whether the subject has experienced an abnormal potassium serum level since receiving their last provision of the angiotensin II receptor blocker pharmaceutical composition. Accordingly, in some embodiments the second plurality of reassessment filters includes a potassium serum level reassessment filter that is fired at least when the plurality of reassessment results indicates that the subject has experienced, since receiving their last provision of the angiotensin II receptor blocker pharmaceutical composition, an abnormal potassium serum level.

Referring to block 540 of FIG. 5C, in some embodiments the reassessment survey results further includes whether the subject has developed a side effect associated with the angiotensin II receptor blocker pharmaceutical composition since receiving their last provision of the angiotensin II receptor blocker pharmaceutical composition. Accordingly, in some embodiments, the second plurality of reassessment filters further includes a side effect reassessment filter that is configured to be fired at least when the reassessment survey results indicate that the subject has developed a side effect since receiving their last provision of the angiotensin II receptor blocker pharmaceutical composition. Side effects that are capable of triggering (e.g., triggering condition) the side effect filter include hypotension. In some embodiments, side effects that are capable of triggering (e.g., triggering condition) the side effect filter include high potassium serum levels, swelling of the face, swelling of the tongue, swelling of the throat, a skin rash, sinus pain and/or sinus congestion (e.g., sinusitis), back pain, and/or diarrhea. In some embodiments, side effects that are capable of triggering (e.g., triggering condition) the side effect filter include problems of the kidney such as swelling of the feet, swelling of the ankles, swelling of the hands, unexplained weight gain, and/or heart failure. In some embodiments, side effects that are capable of triggering (e.g., triggering condition) the side effect filter include chest pain, orthostatic hypotension, anemia, hyperkalemia, hypoglycemia, and/or a urinary tract infection.

Referring to block 542 of FIG. 5C, in some embodiments the method also includes obtaining acknowledgment from the subject for each warning issued to the subject by any filter in the second plurality of reassessment filters. As described with respect to the warnings issued in conjunction with the second plurality of assessment filters of the second category class, in some embodiments, the warning includes a prompt for the subject to indicate whether they have discussed the risk factor underlying the respective filter in the second plurality of reassessment filters that was fired with a health care practitioner (e.g., a licensed medical practitioner), e.g., and the health care practitioner indicated that the subject should take a angiotensin II receptor blocker pharmaceutical composition in view of the underlying risk factor. Accordingly, acknowledgement is obtained from the subject when the subject indicates that they have discussed the risk factor underlying the respective filter in the second plurality of reassessment filters that was fired with a health care provider.

Referring to block 544 of FIG. 5D, in some embodiments the procedure further includes proceeding with the re-fulfillment process when the re-fulfillment process is not already terminated by the firing of a filter in the first plurality of reassessment filters (e.g., the pregnancy reassessment filter). Moreover, in order for the re-fulfillment process to complete the subject is required to acknowledge each warning associated with each filter 222-2 in the second plurality of reassessment filters that was fired.

Referring to block 546 of FIG. 5D, in some embodiments when a respective filter in the first plurality of reassessment filters or second plurality of reassessment filters is fired, a record associated with the firing of the respective filter is stored (e.g., memorializing an adverse event that is required to be reported to a regulatory agency). This record is stored in an adverse event module 242 which includes records of filter firing events associated with a plurality of subjects (e.g., an aggregation of adverse events associated with the angiotensin II receptor blocker pharmaceutical composition across a population of subjects taking the angiotensin II receptor blocker pharmaceutical composition over-the-counter). In some embodiments, an indication of the adverse event is communicated to a third party (e.g., a medical practitioner associated with the subject, a health care provider of the subject, and/or a manufacturer/promoter of the angiotensin II receptor blocker pharmaceutical composition). In some embodiments, the indication is automatically stored in the adverse event module 242 when submitted by a subject as part of the reassessment survey.

In some embodiments, an adverse event that is required to be reported includes an allergic reaction (e.g., a side effect and/or a drug interaction) of any type or kind as described above. In some embodiments, an adverse event that is required to be reported includes an anticipated and/or recent change in pregnancy status of a respective subject. In some embodiments, an adverse event that is required to be reported includes an indication that a respective subject has experienced symptoms of hypotension (e.g., since receiving their last provision of the angiotensin II receptor blocker). In some embodiments, an adverse event that is required to be reported includes a worsening of kidney function for a respective subject. Furthermore, in some embodiments an adverse event that is required to be reported includes an indication of a respective subject experiencing a significant (e.g., detectable) electrolyte imbalance (e.g., an abnormal electrolyte blood level).

Referring to block 548 of FIG. 5D, in some embodiments the re-fulfillment process also includes storing an indication in the user profile 234 of the subject of a re-order 238 for the angiotensin II receptor blocker pharmaceutical composition. The re-fulfillment process further includes communicating an over-the-counter drug facts label 230 for the angiotensin II receptor pharmaceutical composition to the subject. As previously described, the communication of the over-the-counter drug facts label 230 can occur in a variety of means. Upon confirmation from the subject that the over-the-counter drug facts label 230 has been received and read, the method includes authorizing a re-order provision of the angiotensin II receptor blocker pharmaceutical composition to the subject. In some embodiments, this re-order provision includes the destination of the subject.

FIG. 8 illustrates an example method (800) (e.g., performed at an electric device) for qualifying a subject for an over-the-counter angiotensin II receptor blocker pharmaceutical composition. In some embodiments, the method of FIG. 8 is utilized when the subject has not been previously qualified for the medication (e.g., an assessment for the medication). In some embodiments, the method of FIG. 8 is utilized when the subject was previously qualified for the angiotensin II receptor blocker pharmaceutical composition but a predetermined period of time elapsed since the previous qualification occurred (e.g., the most recent qualification of the subject was greater than one year ago).

Referring to FIG. 8, the device prompts (802) the subject to acknowledge a privacy notice. Since the present disclosure requires the subject to know and input sensitive medical information (e.g., information only the subject and a medical practitioner have access to), privacy of this information is important. Once the subject has acknowledged they have the requisite privacy for continuing, the device prompts (804) the user to confirm that they know their blood pressure and cholesterol levels (e.g., because in some embodiments the subject must know their blood pressure and their total cholesterol, including their HDL, values in order to complete the qualification process). If the subject indicates they do not know their blood pressure and/or cholesterol level, the process terminates 895-2 without authorizing provision of the angiotensin II receptor blocker pharmaceutical composition, and optionally transmits advice to the user to return later, e.g., once they know their blood pressure and cholesterol levels. If the subject indicates they know their blood pressure and cholesterol levels, the process continues.

The device prompts the subject to provide information about their pregnancy status and then applies (805) the answer received from the subject to a pregnancy assessment filter. When the pregnancy assessment filter is fired (e.g., when the answer indicates the subject is pregnant, breast-feeding, or planning to become pregnant), the device terminates (895-1) the qualification process without authorizing provision of the angiotensin II receptor blocker pharmaceutical agent and, optionally, transmits advice to the user as to why they should not take the angiotensin II receptor blocker pharmaceutical agent.

When the pregnancy reassessment filter is not fired, the device proceeds with the qualification process, prompting the subject to indicate whether they are taking a medication that interacts with the angiotensin II receptor blocker and then applies (810) the answer received from the subject to a drug interaction assessment filter. When the drug interaction assessment filter is fired (e.g., when the answer indicates the subject is taking a medication that interacts with the angiotensin II receptor blocker), the device terminates (895-1) the qualification process without authorizing provision of the angiotensin II receptor blocker pharmaceutical agent and, optionally, transmits advice to the user as to why they should not take the angiotensin II receptor blocker pharmaceutical agent.

When the drug interaction assessment filter is not fired, the device proceeds with the qualification process, prompting the subject to provide their blood pressure and then applies (815) the answer received from the subject to a blood pressure assessment filter. When the blood pressure assessment filter is fired (e.g., when the answer indicates the subject has hypertension), the device terminates (895-3 through 895-6) the qualification process without authorizing provision of the angiotensin II receptor blocker pharmaceutical agent. Optionally, when the device terminates the process in response to determining (815-2) the subject has slightly elevated blood pressure, the device transmits (895-3) advice for the subject to maintain a healthy diet and to exercise. Optionally, when the device terminates the process in response to determining (815-3) the subject has normal blood pressure, the device transmits (895-4) advice for the subject that they do not need an angiotensin II receptor blocker pharmaceutical agent. Optionally, when the device terminates the process in response to determining (815-4) the subject has hypertension stage 2, the device transmits (895-5) advice for the subject to discuss obtaining a prescription for an angiotensin II receptor blocker pharmaceutical agent with a medical professional. Optionally, when the device terminates the process in response to determining (815-4) the subject is in hypertensive crisis, the device transmits (895-6) advice for the subject to seek emergency medical care.

When the blood pressure assessment filter is not fired, the device proceeds with the qualification process, prompting the subject to provide information about their cardiovascular history (820), prompting the subject to provide their gender (825), prompting the subject to provide their age (830), prompting the subject to provide their race (835), whether they are currently taking blood pressure medication (840), whether they have diabetes (845), their history of smoking (850), and their cholesterol levels (855). If no record of an exemption condition was created (e.g., the subject has not had a cardiovascular problem or heart procedure and is younger than 80), the device calculates an atherosclerotic cardiovascular disease (ASCVD) event risk for the subject (e.g., based on the answers to prompts (815-855) and applies (865) the calculated risk to a pooled cohort equation filter.

When the pooled cohort equation filter is fired (e.g., when the risk of an ASCVD event is less than 10 percent or is incalculable), the device terminates (895-3, 895-7) the qualification process without authorizing provision of the angiotensin II receptor blocker pharmaceutical agent. Optionally, when the device terminates the process in response to determining (865-2) the subject has an incalculable risk for an ASCVD event, the device transmits (895-7) advice for the subject to visit a medical professional to discuss whether taking an angiotensin II receptor blocker pharmaceutical agent is appropriate. Optionally, when the device terminates the process in response to determining (865-3) that the subject has a low risk of an ASCVD event (e.g., less than 10%), the device transmits (895-3) advice for the subject to maintain a healthy diet and to exercise.

When the pooled cohort equation assessment filter is not fired, the device proceeds with the qualification process, prompting the subject to indicate whether they have had kidney problems and then applies (870) the answer received from the subject to a kidney problem assessment filter. In some embodiments, when the kidney problem assessment filter is fired (e.g., when the answer indicates the subject has had a kidney problem), the device initiates (880-1) an override procedure (e.g., creates a record indicating that the user must confirm they have discussed taking an angiotensin II receptor blocker pharmaceutical composition with a health care provider).

When the kidney problem assessment filter is not fired, the device proceeds with the qualification process, prompting the subject to indicate whether they have been told they have abnormal electrolyte blood levels and applies (875) the answer received from the subject to an electrolyte blood level assessment filter. In some embodiments, when the electrolyte blood level assessment filter is fired (e.g., when the answer indicates the subject has a had an abnormal electrolyte blood level), the device initiates (880-2) an override procedure (e.g., creates a record indicating that the user must confirm they have discussed taking an angiotensin II receptor blocker pharmaceutical composition with a health care provider).

In some embodiments, the device proceeds with the qualification process, determining (882) whether the override procedure has been triggered (e.g., by firing of either of the kidney problem or electrolyte blood level assessment filters). If the override procedure has been triggered, the device prompts (884) the user to confirm that they have spoken with a medical professional about taking an angiotensin II receptor blocker pharmaceutical composition (e.g., in view of the underlying risk factor that triggered the kidney problem and/or electrolyte blood level assessment filters) and the medical professional recommended taking the angiotensin II receptor blocker pharmaceutical composition. If the user's response indicates they have not spoken with a medical professional or the medical professional did not recommend taking the angiotensin II receptor blocker pharmaceutical composition, the device terminates (895-8) the process and, optionally, transmits advice for the subject to consult a medical professional.

If the override procedure was not triggered, or the override procedure was triggered and the subject's response indicated that a medical professional recommended they take an angiotensin II receptor blocker pharmaceutical composition (e.g., in view of the underlying risk factor triggering the override procedure), the device proceeds with the qualification process, prompting (885) the subject to confirm their answers. If the user confirms their answers, the device transmits (890) a drug facts label for angiotensin II receptor blocker pharmaceutical composition and prompts the user to read the drug facts label. If the subject confirms they have read the drug facts label, the device proceeds to authorize (895) purchase of the angiotensin II receptor blocker pharmaceutical composition.

FIG. 9 illustrates an example method for qualifying a subject for a refill (e.g., a reassessment) of an over-the-counter angiotensin II receptor blocker pharmaceutical composition (e.g., following a prescription from a medical professional or initial qualification by a method described herein). Referring to FIG. 9, the device prompts (902) the subject to acknowledge a privacy notice. Once the subject has acknowledged they have the requisite privacy for continuing, the device determines (905) whether a blood pressure input for the subject is required. When a new blood pressure input is required (e.g., when the subject's profile does not include a record of the subject's blood pressure taken within the past month, e.g., for a first reorder process, or within the past six months, e.g., for a subsequent reorder process), the device prompts (910) the subject to confirm they know their blood pressure. When the user indicates they do not know their blood pressure, the device terminates (995-1) the process without authorizing provision of the angiotensin II receptor blocker pharmaceutical agent, optionally transmitting advice for the user to return once they know their blood pressure. When the user indicates they do know their blood pressure, the device proceeds with the process, prompting the user to indicate whether their blood pressure is below a threshold target level (e.g., under 130/80, evidencing the efficacy of the angiotensin II receptor blocker pharmaceutical agent) and applies (910) the answer received from the subject to a blood pressure reassessment filter. When the blood pressure reassessment filter is fired (e.g., when the reassessment answer indicates the subject has a blood pressure is not below a threshold target level, e.g., 130/80), the device terminates (995-2) the qualification process, optionally transmitting advice for the subject to discuss taking a prescription-strength angiotensin II receptor blocker pharmaceutical agent with a medical professional.

When the blood pressure reassessment filter is not fired, or the subject's answer indicates their blood pressure is below the threshold target level, the device proceeds with the qualification process, prompting the subject to provide information about their pregnancy status and then applies (915) the answer received from the subject to a pregnancy reassessment filter. In some embodiments, when the pregnancy reassessment filter is fired (e.g., when the answer indicates the subject is pregnant, breastfeeding, or planning to become pregnant), the device creates (990-1) a record of an adverse event (e.g., aggregated in an adverse event data store having records of adverse events from a plurality of users), terminates (995-3) the qualification process and, optionally, transmits advice to the user as to why they should not take the angiotensin II receptor blocker pharmaceutical composition.

When the pregnancy reassessment filter is not fired, the device proceeds with the qualification process, prompting the subject to provide information about their current medications and then applies (820, 825, 830) the answer received from the subject to a drug interaction reassessment filter. In some embodiments, the device prompts the subject to provide information about whether the subject is currently taking a lithium medication (920). In some embodiments, the device prompts the subject to provide information about whether the subject is currently taking a non-steroidal anti-inflammatory medication (925). In some embodiments, the device prompts the subject to provide information about whether the subject is currently taking a blood pressure medication (e.g., a high blood pressure medication) (930). When the drug interaction reassessment filter is fired (e.g., when the answer indicates the subject has started taking a medication that interactions with the angiotensin II receptor blocker pharmaceutical composition), the device terminates (995-3) the qualification process and, optionally, transmits advice to the user as to why they should not take the angiotensin II receptor blocker pharmaceutical composition.

When the drug interaction reassessment filter is not fired, the device proceeds with the qualification process, prompting the subject to indicate whether they have developed hypotension since receiving their last provision of the angiotensin II receptor blocker and then applies (940) the answer received from the subject to a hypotension reassessment filter. When the hypotension reassessment filter is fired (e.g., when the answer indicates the subject has developed symptoms of hypotension since receiving their last provision of the angiotensin II receptor blocker), the device optionally creates a record of an adverse event (e.g., aggregated in an adverse event data store having records of adverse events from a plurality of users) and initiates (935-2) an override procedure (e.g., creates a record indicating that the user must confirm they have discussed taking angiotensin II receptor blocker pharmaceutical composition with a health care professional).

When the hypotension reassessment filter is not fired, the device proceeds with the qualification process, promoting the subject to indicate whether they have developed abnormal electrolyte blood levels since receiving their last provision of the angiotensin II receptor blocker and then applies (945) the answer received from the subject to an electrolyte blood level reassessment filter. When the electrolyte blood level reassessment filter is fired (e.g., when the answer indicates the subject has developed an abnormal electrolyte blood level since receiving their last provision of the angiotensin II receptor blocker), the device optionally creates a record of an adverse event (e.g., aggregated in an adverse event data store having records of adverse events from a plurality of users) and initiates (935-2) an override procedure (e.g., creates a record indicating that the user must confirm they have discussed taking angiotensin II receptor blocker pharmaceutical composition with a health care professional).

When the electrolyte blood level reassessment filter is not fired, the device proceeds with the qualification process, prompting the subject to indicate whether they have developed a kidney problem and then applies (950) the answer received from the subject to a kidney problem reassessment filter. When the kidney problem reassessment filter is fired (e.g., when the answer indicates the subject has developed a kidney problem since receiving their last provision of the angiotensin II receptor blocker pharmaceutical composition), the device creates (990-2) a record of an adverse event (e.g., aggregated in an adverse event data store having records of adverse events from a plurality of users) and initiates (935-3) an override procedure (e.g., creates a record indicating that the user must confirm they have discussed taking an angiotensin II receptor blocker pharmaceutical composition with a health care professional).

The device proceeds with the qualification process, determining (935) whether the override procedure has been triggered (e.g., by firing of any one of hypotension or kidney problem reassessment filters, etc.). If the override procedure has been triggered, the device prompts (937) the user to confirm that they have spoken with a medical professional about taking an angiotensin II receptor blocker pharmaceutical composition (e.g., in view of the underlying risk factor that triggered the hypotension or kidney problem reassessment filter) and the medical professional recommended taking the angiotensin II receptor blocker pharmaceutical composition. If the user's response indicates they have not spoken with a medical professional or the medical professional did not recommend taking the angiotensin II receptor blocker pharmaceutical composition, the device terminates (995-3) the process and, optionally, transmits advice for the subject to consult a medical professional.

If the override procedure was not triggered, or the override procedure was triggered and the subject's response indicated that a medical professional recommended they take an angiotensin II receptor blocker pharmaceutical composition (e.g., in view of the underlying risk factor triggering the override procedure), the device proceeds with the re-qualification process, prompting (955) the subject to confirm their answers. If the user confirms their answers, the device transmits (960) a drug facts label for the angiotensin II receptor blocker pharmaceutical composition and prompts the user to read the drug facts label. If the subject confirms they have read the drug facts label, the device proceeds to authorize purchase of the angiotensin II receptor blocker pharmaceutical composition Specific Embodiments In one aspect, the disclosure provides methods, software, and computer systems for qualifying a human subject for over-the-counter delivery of an angiotensin II receptor blocker pharmaceutical composition to lower blood pressure, e.g., treating or preventing heart disease. In one embodiment, a computer system (e.g., computer system 250 in FIG. 2) includes instructions for conducting an assessment survey of the subject (e.g., assessment module 252 in FIG. 2) to obtain information about the subject necessary to run against at least two series of filters (e.g., first assessment filter category class 214 in FIG. 2 and second assessment filter category class 220 in FIG. 2). The computer system also includes instructions for running the assessment survey results against the assessment filters. Filters 216 in the first series of assessment filters prevent authorization for delivery of the OTC angiotensin II receptor blocker where the subject's assessment survey results identify a contraindication for the OTC angiotensin II receptor blocker. Filters 222 in the second series of assessment filters generate a warning 226 where the subject's survey results identify a risk factor for the OTC angiotensin II receptor. In some embodiments, the warning 226 includes a prompt requiring the subject to confirm they have discussed the risk factor with a physician in order to proceed with qualification for the OTC a blocker.

In one aspect, the disclosure provides methods, software, and computer systems for qualifying a human subject for a re-order (e.g., reassessment) for over-the-counter delivery of an angiotensin II receptor blocker pharmaceutical composition to lower blood pressure, e.g., treating or preventing heart disease. In one embodiment, a computer system includes instructions, responsive to receiving a re-order request from the subject for the angiotensin II receptor blocker pharmaceutical composition, performing a re-fulfillment procedure (e.g., reassessment procedure) including, for conducting a reassessment survey of the subject to obtain reassessment survey results for qualifying the subject for the re-order, e.g., associated with at least two series of filters (e.g., a first series of reassessment filters of a first category class 214-2 in FIG. 2 and second series of reassessment filters of a second category class 220-2 in FIG. 2). The computer system also includes instructions for running the reassessment survey results against the reassessment filters. Filters 216 in the first series of reassessment filters prevent authorization for delivery of the OTC angiotensin II receptor blocker where the subject's survey results identify a contraindication for the OTC angiotensin II receptor blocker. Filters 222 in the second series of reassessment filters generate a warning 226 where the subject's reassessment survey results identify a risk factor for the OTC angiotensin II receptor blocker. In some embodiments, the warning 226 includes a prompt requiring the subject to confirm they have discussed the risk factor with a physician in order to proceed with qualification for the OTC angiotensin II receptor blocker.

The computer system includes instructions for proceeding with a re-fulfillment process only when no filters in the first series of reassessment filters was fired and the subject acknowledged each warning associated with each filter in the second plurality of reassessment filters that was fired. The computer system also includes instructions for storing an indication in a subject profile of a re-order for the angiotensin II receptor blocker pharmaceutical composition The computer system also includes instructions for communicating an over-the-counter drug facts label 230 for the angiotensin II receptor blocker pharmaceutical composition to the subject and, upon confirmation that the over-the-counter drug facts label has been received and read, authorizing provision of the OTC angiotensin II receptor blocker pharmaceutical composition to the subject.

In one aspect, the disclosure provides a computer system for qualifying a human subject for over-the-counter delivery of an angiotensin II receptor blocker pharmaceutical composition to lower blood pressure. The computer system comprising one or more processors and a memory, the memory comprising non-transitory instructions which, when executed by the one or more processor, perform a method for qualifying a human subject for over-the-counter delivery of the angiotensin II receptor blocker pharmaceutical composition. The method includes conducting an assessment survey of the subject thereby obtaining a plurality of assessment survey results necessary to run against a first plurality of assessment filters of a first category class and a second plurality of assessment filters of a second category class. The method then includes running all or a portion of the first plurality of assessment survey results against a first plurality of assessment filters of a first category class, wherein, when a respective filter in the first plurality of assessment filters is fired, the subject is deemed not qualified for delivery of the angiotensin II receptor blocker pharmaceutical composition and the method is terminated without delivery of the angiotensin II receptor blocker pharmaceutical composition to the subject. The method then includes running all or a portion of the plurality of assessment survey results against a second plurality of assessment filters of a second category class, wherein, when a respective filter in the second plurality of assessment filters is fired, the subject is provided with a warning corresponding to the respective filter. The method also includes obtaining acknowledgment from the subject for the warning issued to the subject by any filter in the second plurality of assessment filters. The method also includes proceeding with a fulfillment process when no filter in the first plurality of assessment filters has been fired and the subject has acknowledged each warning associated with each filter in the second plurality of assessment filters that was fired. The fulfillment process includes: storing an indication in a subject profile of an initial order for the angiotensin II receptor blocker pharmaceutical composition, communicating an over-the-counter drug facts label for the angiotensin II receptor blocker pharmaceutical composition to the subject, and authorizing, upon confirmation from the subject that the over-the-counter drug facts label has been received and read, provision of the angiotensin II receptor blocker pharmaceutical composition to the subject. In some embodiments, the authorization includes a destination associated with the subject.

In some embodiments, the plurality of assessment survey results includes a plurality of assessment survey results selected from the survey results listed in Table 1. In one embodiment, the plurality of assessment survey results includes: whether the subject is one of (i) pregnant, (ii) breastfeeding, or (iii) planning to become pregnant, whether the subject is taking a medication that interacts with the angiotensin II receptor blocker pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, and whether the subject has ever had a kidney problem.

In some embodiments, the first plurality of assessment filters includes a plurality of assessment filters selected from the filters listed in Table 2. In one embodiment, the first plurality of assessment filters includes blood pressure assessment, a pregnancy assessment filter, a drug interaction assessment filter, an age assessment filter, and a pooled cohort equation assessment filter.

In some embodiments, the second plurality of assessment filters includes a plurality of assessment filters selected from the filters listed in Table 4. In one embodiment, the second plurality of assessment filters includes a kidney problem assessment filter and an electrolyte blood level assessment filter.

In some embodiments, the first and second plurality of assessment filters includes filters selected from the filters listed in Table 8. In some embodiments, the first plurality of assessment filters of the first category class include a first sub-plurality of the filters listed in Table 8, for example, 2, 3, 4, 5, 6, or all 7 of the filters listed in Table 8, and the second plurality of assessment filters of the first category class include a second sub-plurality of the filters listed in Table 8, which is different from the first sub-plurality of filters, for example, 2, 3, 4, 5, 6, or all 7 of the filters listed in Table 8. In some embodiments, each of the filters in the first sub-plurality of filters is different from each of the filters in the second sub-plurality of filters (e.g., no filter listed in Table 8 is included in both the first sub-plurality and the second sub-plurality of filters). In some embodiments, a system for qualifying a subject for delivery of an over-the-counter angiotensin II receptor blocker pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 8, e.g., at least 2, 3, 4, 5, 6, or all 7 of the filters listed in Table 8. In some embodiments, where a filter listed in Table 8 corresponds to a filter listed in Table 2 or Table 4, a threshold level sufficient to fire the corresponding filter listed in Table 2 or Table 4, as described in detail above, is sufficient to fire the filter listed in Table 8.

TABLE 8

Example Assessment Filters

| Filter | Exemplary Criteria |
| --- | --- |
| 1b | a pregnancy assessment filter |
| 2b | a drug interaction assessment filter |
| 3b | a blood pressure assessment filter |
| 4b | an age assessment filter |
| 5b | a pooled cohort equation assessment filter |
| 7b | a kidney problem assessment filter |
| 8b | an electrolyte blood level assessment filter |

In one aspect, the disclosure provides methods, software, and computer systems for qualifying a human subject for a re-order (e.g., a reassessment) for over-the-counter delivery of an angiotensin II receptor blocker pharmaceutical composition to lower blood pressure, e.g., treating or preventing heart disease. In one embodiment, a computer system includes instructions, responsive to receiving a re-order request from the subject for the angiotensin II receptor blocker pharmaceutical composition, performing a re-fulfillment procedure comprising conducting a reassessment survey of the subject thereby obtaining a plurality of reassessment survey results necessary to run against a first plurality of reassessment filters of a first category class and a second plurality of reassessment filters of a second category class. The method then includes running all or a portion of the plurality of reassessment survey results against a first plurality of reassessment filters of a first category class, wherein, when a respective filter in the first plurality of reassessment filters is fired, the subject is deemed not qualified for delivery of the angiotensin II receptor blocker pharmaceutical composition and the method is terminated without delivery of the angiotensin II receptor blocker pharmaceutical composition to the subject. The method then includes running all or a portion of the plurality of assessment survey results against a second plurality of reassessment filters of a second category class, wherein, when a respective filter in the second plurality of reassessment filters is fired, the subject is provided with a warning corresponding to the respective filter. The method also includes obtaining acknowledgment from the subject for the warning issued to the subject by any filter in the second plurality of reassessment filters. The method also includes proceeding with a re-fulfillment process when no filter in the first plurality of reassessment filters has been fired and the subject has acknowledged each warning associated with each filter in the second plurality of reassessment filters that was fired. The re-fulfillment process includes: storing an indication in a subject profile of a re-order for the angiotensin II receptor blocker pharmaceutical composition, communicating the over-the-counter drug facts label for the angiotensin II receptor blocker pharmaceutical composition to the subject, and authorizing, upon confirmation from the subject that the over-the-counter drug facts label has been received and read, provision of the angiotensin II receptor blocker pharmaceutical composition to the subject.

In some embodiments, the first series of reassessment filters includes one or more filters listed in Table 6. In some embodiments, the first plurality of reassessment filters includes a blood pressure reassessment filter, a pregnancy reassessment filter, a drug interaction reassessment filter, a hypotension reassessment filter, an electrolyte blood level reassessment filter, and a kidney problem reassessment filter.

In some embodiments, the fourth series of filters includes one or more filters listed in Table 7. In some embodiments, the fourth plurality of filters includes a renal function reassessment filter and/or a potassium serum level reassessment filter.

In some embodiments, the first and second plurality of reassessment filters includes filters selected from the filters listed in Table 9. In some embodiments, the first plurality of reassessment filters of the first category class include a first sub-plurality of the filters listed in Table 9, for example, 2, 3, 4, 5, or all 6 of the filters listed in Table 9, and the second plurality of reassessment filters of the first category class include a second sub-plurality of the filters listed in Table 9, which is different from the first sub-plurality of filters, for example, 2, 3, 4, 5, or all 6 of the filters listed in Table 9. In some embodiments, each of the filters in the first sub-plurality of filters is different from each of the filters in the second sub-plurality of filters (e.g., no filter listed in Table 9 is included in both the first sub-plurality and the second sub-plurality of filters). In some embodiments, a system for qualifying a subject for delivery of an over-the-counter angiotensin II receptor blocker pharmaceutical composition includes instructions for applying only one plurality of reassessment filters, e.g., only filters of a single category class of filters. In some embodiments, where the method, system, or software applies a single plurality of reassessment filters, the plurality of reassessment filters includes a plurality of reassessment filters selected from the filters listed in Table 9, e.g., at least 2, 3, 4, 5, or all 6 of the filters listed in Table 9. In some embodiments, where a filter listed in Table 9 corresponds to a filter listed in Table 2, Table 4, Table 6, or Table 7, a threshold level sufficient to fire the corresponding filter listed in Table 2, Table 4, Table 6, or Table 7, as described in detail above, is sufficient to fire the filter listed in Table 9.

TABLE 9

Example Reassessment Filters

| Filter | Exemplary Criteria |
| --- | --- |
| 1b | a pregnancy reassessment filter |
| 2b | a blood pressure reassessment filter |
| 3b | a drug interaction reassessment filter |
| 4b | a hypotension reassessment filter |
| 5b | an electrolyte blood level reassessment filter |
| 6b | a kidney problem reassessment filter |

In one aspect, the present disclosure provides a computer system for qualifying a human subject for over-the-counter delivery of angiotensin II receptor blocker pharmaceutical composition for lowering blood pressure. The computer system includes one or more processors and a memory, the memory comprising non-transitory instructions which, when executed by the one or more processor, perform a method. The method includes a) conducting an assessment survey of the subject thereby obtaining a plurality of assessment survey results. The plurality of assessment survey results includes whether the subject is one of (i) pregnant, (ii) breastfeeding, or (iii) planning to become pregnant, whether the subject is taking a medication that interacts with the angiotensin II receptor blocker pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, and whether the subject has ever had a kidney problem. The method further includes b) running all or a portion of the plurality of assessment survey results against a first plurality of assessment filters of a first category class. When a respective filter in the first plurality of assessment filters is fired, the subject is deemed not qualified for delivery of the angiotensin II receptor blocker pharmaceutical composition and the method is terminated without delivery of the angiotensin II receptor blocker pharmaceutical composition to the subject. The first plurality of assessment filters includes a pregnancy assessment filter that is fired at least when the plurality of assessment survey results indicates that the subject is pregnant or the subject is breastfeeding, a drug interaction assessment filter that is fired at least when the plurality of assessment survey results indicate that the subject is taking a medication that interacts with the angiotensin II receptor blocker pharmaceutical composition, a blood pressure assessment filter that is fired at least when the plurality of assessment survey results indicates the subject is not hypertensive or the subject has severe hypertension, an age assessment filter that is fired at least when the plurality of assessment survey results indicate the subject is too young to receive the angiotensin II receptor blocker pharmaceutical composition, and a pooled cohort equation assessment filter that is fired at least when the plurality of assessment survey results indicate that the subject has a risk for atherosclerotic cardiovascular disease that is below a floor threshold of risk or the subject has an incalculable risk for atherosclerotic cardiovascular disease. Further, the method includes c) running all or a portion of the plurality of assessment survey results against a second plurality of assessment filters of a second category class. When a respective filter in the second plurality of assessment filters is fired, the subject is provided with a warning corresponding to the respective filter. The second plurality of assessment filters includes an electrolyte blood level assessment filter that is fired at least when the plurality of assessment survey results indicates that the subject has had an abnormal electrolyte blood level, and a kidney problem assessment filter that is fired at least when the plurality of assessment survey results indicates that the subject has had a kidney problem. Furthermore, the method includes d) obtaining acknowledgment from the subject for the warning issued to the subject by any filter in the second plurality of filters. Additionally, the method includes e) proceeding with a fulfillment process when (i) no filter in the first plurality of filters has been fired and (ii) the subject has acknowledged each warning associated with each filter in the second plurality of filters that was fired. Accordingly, the fulfillment process includes: storing an indication in a subject profile of an initial order for the angiotensin II receptor blocker pharmaceutical composition, communicating an over the counter drug facts label for the angiotensin II receptor blocker pharmaceutical composition to the subject, and authorizing, upon confirmation from the subject that the over the counter drug facts label has been received and read, provision of the angiotensin II receptor blocker pharmaceutical composition to the subject.

In some embodiments, the angiotensin II receptor blocker pharmaceutical composition includes an active ingredient having the structure:

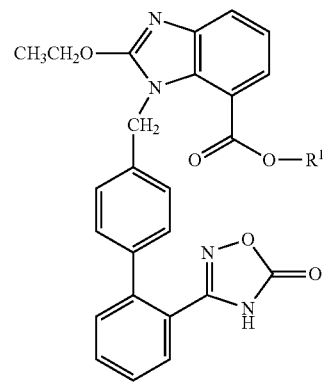

where:
R1 is a group represented by the formula:

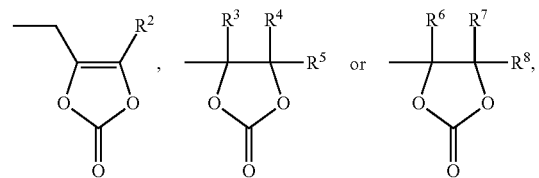

and
R2, R3, R4, R5, R6, R7, and R8 are each independently a hydrogen atom or a C1-6 alkyl, or a salt thereof.

In some embodiments, the angiotensin II receptor blocker pharmaceutical composition includes an active ingredient that is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate or a pharmaceutically acceptable salt thereof.

In some embodiments, the angiotensin II receptor blocker pharmaceutical composition includes an active ingredient that is azilsartan medoxomil or a pharmaceutically acceptable salt thereof.

In some embodiments, upon confirmation from the subject that the over the counter drug facts label has been received and read, the subject is authorized for provision of a dosage of from 40 mg to 80 mg per day of the active ingredient of the angiotensin II receptor blocker pharmaceutical composition.

In some embodiments, the active ingredient of the angiotensin II receptor blocker pharmaceutical composition includes an active ingredient selected from the group consisting of candesartan, eprosartan, irbesartan, losartan, olmesartan, telmisartan, and valsartan.

In some embodiments, upon confirmation from the subject that the over the counter drug facts label has been received and read, the subject is authorized for provision of a dosage of from 4 mg to 32 mg of candesartan per day.

In some embodiments, the angiotensin II receptor blocker pharmaceutical composition includes candesartan. Accordingly, the plurality of assessment survey results further includes whether the subject has a liver problem, and the first plurality of assessment filters includes a liver problem assessment filter that is fired at least when the plurality of assessment survey results indicates that the subject has advanced liver disease.

In some embodiments, upon confirmation from the subject that the over the counter drug facts label has been received and read, the subject is authorized for provision of a dosage of from 400 mg to 800 mg of eprosartan per day.

In some embodiments, upon confirmation from the subject that the over the counter drug facts label has been received and read, the subject is authorized for provision of a dosage from 75 mg to 300 mg of irbesartan per day.

In some embodiments, upon confirmation from the subject that the over the counter drug facts label has been received and read, the subject is authorized for provision of a dosage of from 25 mg to 100 mg of losartan per day.

In some embodiments, the angiotensin II receptor blocker pharmaceutical composition includes losartan. Accordingly, the plurality of assessment survey results further includes whether the subject is taking a potassium supplement or a salt substitute that includes potassium, and the second plurality of assessment filters includes a potassium supplement assessment filter that is fired at least when the plurality of assessment survey results indicates that the subject is taking a potassium supplement or a salt substitute that includes potassium.

In some embodiments, the angiotensin II receptor blocker pharmaceutical composition includes losartan. Accordingly, the plurality of assessment survey results further includes whether the subject has ever had a liver problem, and the first plurality of assessment filters includes a liver problem assessment filter that is fired at least when the plurality of assessment survey results indicates that the subject has had a liver problem.

In some embodiments, upon confirmation from the subject that the over the counter drug facts label has been received and read, the subject is authorized for provision of a dosage of from 5 mg to 40 mg of olmesartan per day.

In some embodiments, the angiotensin II receptor blocker pharmaceutical composition includes olmesartan. Accordingly, the plurality of assessment survey results further includes whether the subject is taking colesevelam, and the second plurality of assessment filters includes a colesevelam interaction assessment filter that is fired at least when the plurality of assessment survey results indicates that the subject is taking colesevelam.

In some embodiments, upon confirmation from the subject that the over the counter drug facts label has been received and read, the subject is authorized for provision of a dosage of from 20 mg to 80 mg of telmisartan per day.

In some embodiments, the angiotensin II receptor blocker pharmaceutical composition includes telmisartan. Accordingly, the first drug interaction assessment filter is fired when the plurality of assessment survey results indicates that the subject is taking digoxin.

In some embodiments, the angiotensin II receptor blocker pharmaceutical composition includes telmisartan. Accordingly, the plurality of assessment survey results further includes whether the subject has ever had a liver problem, and the second plurality of assessment filters includes a liver problem assessment filter that is fired at least when the plurality of assessment survey results indicates that the subject has had a liver problem.

In some embodiments, the angiotensin II receptor blocker pharmaceutical composition includes telmisartan. Accordingly, the plurality of assessment survey results further includes whether the subject is taking a potassium supplement or a salt substitute that includes potassium, and the second plurality of assessment filters includes a potassium supplement assessment filter that is fired at least when the plurality of assessment survey results indicates that the subject is taking a potassium supplement or a salt substitute that includes potassium.

In some embodiments, the angiotensin II receptor blocker pharmaceutical composition includes telmisartan. Accordingly, the plurality of assessment survey results further includes whether the subject has ever had a heart failure, and the second plurality of assessment filters includes a heart failure assessment filter that is fired at least when the plurality of assessment survey results indicates that the subject has had a heart failure.

In some embodiments, upon confirmation from the subject that the over the counter drug facts label has been received and read, the subject is authorized for provision of a dosage of from 40 mg to 320 mg of valsartan per day.

In some embodiments, the pregnancy assessment filter is also fired when the plurality of assessment survey results indicates that the subject is planning to become pregnant.

In some embodiments, the drug interaction assessment filter is fired when the plurality of assessment survey results indicates that the subject is taking a lithium medication.

In some embodiments, the drug interaction assessment filter is fired when the plurality of assessment survey results indicates that the subject is taking a non-steroidal anti-inflammatory medication.

In some embodiments, the drug interaction assessment filter is fired when the plurality of assessment survey results indicates that the subject is taking a high blood pressure medication.

In some embodiments, a blood pressure that indicates the subject is not hypertensive, and is capable of firing the blood pressure assessment filter, is a systolic blood pressure of less than 130 mm Hg and a diastolic blood pressure of less than 80 mm Hg.

In some embodiments, a blood pressure that indicates the subject has severe hypertension, and is capable of firing the blood pressure assessment filter, is a systolic blood pressure of at least 140 mm Hg or a diastolic blood pressure of at least 90 mm Hg.

In some embodiments, the performed method further includes, when the plurality of assessment survey results indicate that the subject has elevated blood pressure but is not hypertensive firing the blood pressure assessment filter, and transmitting, to the subject, advice to manage their blood pressure by eating healthy and exercising.

In some embodiments, the performed method further includes, when the plurality of assessment survey results indicate that the subject has stage two hypertension firing the blood pressure assessment filter, and transmitting, to the subject, advice to visit a doctor to discuss taking a prescription-strength blood pressure medication.

In some embodiments, the performed method further includes, when the plurality of assessment survey results indicate that the subject is in hypertensive crisis, firing the blood pressure assessment filter, and transmitting, to the subject, advice to seek emergency medical attention.

In some embodiments, the pooled cohort equation assessment filter is fired when the plurality of assessment survey results indicates that the subject has a 10-year risk for atherosclerotic cardiovascular disease, as determined using the pooled cohort equation, that is less than 10%.

In some embodiments, the pooled cohort equation assessment filter is fired when the plurality of assessment survey results indicates that the subject has an incalculable risk for atherosclerotic cardiovascular disease, as determined by one or more inputs of the pooled cohort equation, including: A) the subject is younger than forty years old, B) a total cholesterol level of the subject is either less than 160 mg/dL or greater than 240 mg/dL, C) a high density lipoprotein cholesterol level of the subject is less than 45 mg/dL or greater than 65 mg/dL, D) an untreated systolic blood pressure of the subject is less than 100 mm Hg or greater than 140 mm Hg, or E) a treated systolic blood pressure of the subject is less than 120 mm Hg or greater than 160 mm Hg.

In some embodiments, the method includes bypassing the firing of the pooled cohort equation assessment filter when the plurality of assessment survey results indicates that the subject has an incalculable risk for atherosclerotic cardiovascular disease but has an age that is above a risk threshold age.

In some embodiments, the plurality of assessment survey results further includes a gender of the subject, an age of the subject, a race of the subject, a blood pressure medication status of the subject, a smoking status of the subject, a total cholesterol level of the subject, a high density lipoprotein cholesterol level of the subject, whether the subject has ever had an atherosclerotic cardiovascular history including an atherosclerotic cardiovascular event or a heart procedure, and a diabetes status of the subject. The pooled cohort equation assessment filter incorporates the gender of the subject, the age of the subject, the race of the subject, the blood pressure medication status of the subject, the smoking status of the subject, the total cholesterol of the subject, the high density lipoprotein cholesterol level of the subject, the atherosclerotic cardiovascular history of the subject, and the diabetes status of the subject to derive the risk for atherosclerotic cardiovascular disease.

In some embodiments, the pooled cohort equation is implemented as a multivariable Cox proportional hazard regression.

In some embodiments, the plurality of assessment survey results further includes whether the subject is allergic to the angiotensin II receptor block pharmaceutical composition, and the first plurality of assessment filters includes an adverse reaction assessment filter that is fired when the plurality of assessment survey results indicates that the subject is allergic to the angiotensin II receptor blocker pharmaceutical composition.

In some embodiments, the warning corresponding to a respective filter in the second plurality of assessment filters includes a prompt for the subject to indicate whether they have discussed the risk factor underlying the respective filter in the second plurality of assessment filters that was fired with a health care provider. Accordingly, acknowledgement is obtained from the subject when the subject indicates that they have discussed the risk factor underlying the respective filter in the second plurality of assessment filters that was fired with a health care provider.

In some embodiments, the fulfillment process further includes storing a destination associated with the subject in the subject profile.

In some embodiments, the fulfillment process further includes coordinating shipping of the angiotensin II receptor blocker pharmaceutical composition to a physical address associated with the subject.

In some embodiments, the lowering blood pressure is to treat or prevent a heart disease.

Another aspect of the present disclosure provides a computer system for requalifying a human subject for over-the-counter delivery of an angiotensin II receptor blocker pharmaceutical composition for lowering blood pressure. The computer system comprising one or more processors and a memory, the memory comprising non-transitory instructions which, when executed by the one or more processor, perform a re-fulfillment method comprising, responsive to receiving a re-order request from the subject for the angiotensin II receptor blocker pharmaceutical composition, (a) conducting a reassessment survey of the subject thereby obtaining a plurality of reassessment survey results. The plurality of reassessment survey results includes a systolic blood pressure of the subject, a diastolic blood pressure of the subject, whether the subject is one of (i) pregnant, (ii) breastfeeding, or (iii) planning to become pregnant, whether the subject is taking a medication that interacts with the angiotensin II receptor blocker pharmaceutical composition, whether the subject has experienced symptoms of hypotension since receiving their last provision of the angiotensin II receptor blocker pharmaceutical composition, whether the subject has developed an abnormal electrolyte blood level since receiving their last provision of the angiotensin II receptor blocker pharmaceutical composition, and whether the subject has developed a kidney problem since receiving their last provision of the angiotensin II receptor blocker pharmaceutical composition. Further, the method includes (b) running all or a portion of the plurality of reassessment survey results against a first plurality of reassessment filters of a first category class. When a respective filter in the first plurality of reassessment filters is fired, the subject is deemed not qualified for the angiotensin II receptor blocker pharmaceutical composition and the re-fulfillment process is terminated without delivery of the angiotensin II receptor blocker pharmaceutical composition to the subject. The first plurality of reassessment filters include a blood pressure reassessment filter that is fired at least when the plurality of reassessment survey results indicates the subject has hypertension, a pregnancy reassessment filter that is fired at least when the plurality of reassessment survey results indicates the subject is pregnant or the subject is breastfeeding, a drug interaction reassessment filter that is fired at least when the plurality of reassessment survey results indicates the subject is taking a medication that interacts with the angiotensin II receptor blocker pharmaceutical composition, a hypotension reassessment filter that is fired at least when the plurality of reassessment survey results indicates that the subject has experienced symptoms of hypotension since receiving their last provision of the angiotensin II receptor blocker pharmaceutical composition, an electrolyte blood level reassessment filter that is fired at least when the plurality of reassessment survey results indicates that the subject has developed an abnormal electrolyte blood level since receiving their last provision of the angiotensin II receptor blocker pharmaceutical composition, and a kidney problem reassessment filter that is fired at least when the plurality of reassessment survey results indicates that the subject has developed a kidney problem since receiving their last provision of the angiotensin II receptor blocker pharmaceutical composition. Additionally, the method includes (c) proceeding with the re-fulfillment when (a) the re-fulfillment is not already terminated by the firing of a filter in the first plurality of reassessment filters. The re-fulfillment further includes storing an indication in the subject profile of a re-order for the angiotensin II receptor blocker pharmaceutical composition, communicating the over the counter drug facts label for the angiotensin II receptor blocker pharmaceutical composition to the subject, and authorizing, upon confirmation from the subject that the over the counter drug facts label has been received and read, a re-order provision of the angiotensin II receptor blocker pharmaceutical composition to the subject.

In some embodiments, the angiotensin II receptor blocker pharmaceutical composition is selected from the group consisting of azilsartan medoxomil, candesartan, eprosartan, irbesartan, losartan, olmesartan, telmisartan, and valsartan.

In some embodiments, the angiotensin II receptor blocker pharmaceutical composition includes irbesartan. Accordingly, the plurality of reassessment survey results further includes whether the subject has experienced an impaired renal function since receiving their last provision of the angiotensin II receptor blocker pharmaceutical composition, and the re-fulfillment process includes running all or a portion of the plurality of reassessment survey results against a renal function reassessment filter of a second category class that is fired at least when the plurality of reassessment survey results indicates that the subject has experienced, since receiving their last provision of the angiotensin II receptor blocker pharmaceutical composition, an impaired renal function, wherein when the renal function reassessment filter is fired, the subject is provided with a warning corresponding to the renal function reassessment filter.

In some embodiments, the angiotensin II receptor blocker pharmaceutical composition includes irbesartan. Accordingly, the plurality of reassessment survey results further includes whether the subject has experienced an abnormal potassium serum level since receiving their last provision of the angiotensin II receptor blocker pharmaceutical composition, and the re-fulfillment process further includes running all or a portion of the plurality of reassessment survey results against a potassium serum level reassessment filter of the second category class that is fired at least when the plurality of reassessment survey results indicates that the subject has experienced, since receiving their last provision of the angiotensin II receptor blocker pharmaceutical composition, an abnormal potassium serum level, wherein when the serum potassium level reassessment filter is fired, the subject is provided with a warning corresponding to the serum potassium level reassessment filter.

In some embodiments, the angiotensin II receptor blocker pharmaceutical composition includes losartan. Accordingly, the plurality of reassessment survey results further includes whether the subject has experienced an impaired renal function since receiving their last provision of the angiotensin II receptor blocker pharmaceutical composition, and the re-fulfillment process includes running all or a portion of the plurality of reassessment survey results against a renal function reassessment filter of a second category class that is fired at least when the plurality of reassessment survey results indicates that the subject has experienced, since receiving their last provision of the angiotensin II receptor blocker pharmaceutical composition, an impaired renal function, wherein when the renal function reassessment filter is fired, the subject is provided with a warning corresponding to the renal function reassessment filter.

In some embodiments, the angiotensin II receptor blocker pharmaceutical composition includes losartan. Accordingly, the plurality of reassessment survey results further includes whether the subject has experienced an abnormal potassium serum level since receiving their last provision of the angiotensin II receptor blocker pharmaceutical composition, and the re-fulfillment process further includes running all or a portion of the plurality of reassessment survey results against a potassium serum level reassessment filter of the second category class that is fired at least when the plurality of reassessment survey results indicates that the subject has experienced, since receiving their last provision of the angiotensin II receptor blocker pharmaceutical composition, an abnormal potassium serum level, wherein when the serum potassium level reassessment filter is fired, the subject is provided with a warning corresponding to the serum potassium level reassessment filter.

In some embodiments, the angiotensin II receptor blocker pharmaceutical composition includes telmisartan. Accordingly, the plurality of reassessment survey results further includes whether the subject has experienced an impaired renal function since receiving their last provision of the angiotensin II receptor blocker pharmaceutical composition, and the re-fulfillment process includes running all or a portion of the plurality of reassessment survey results against a renal function reassessment filter of a second category class that is fired at least when the plurality of reassessment survey results indicates that the subject has experienced, since receiving their last provision of the angiotensin II receptor blocker pharmaceutical composition, an impaired renal function, wherein when the renal function reassessment filter is fired, the subject is provided with a warning corresponding to the renal function reassessment filter.

In some embodiments, the angiotensin II receptor blocker pharmaceutical composition includes telmisartan. Accordingly, the plurality of reassessment survey results further includes whether the subject has experienced an abnormal potassium serum level since receiving their last provision of the angiotensin II receptor blocker pharmaceutical composition, and the re-fulfillment process further includes running all or a portion of the plurality of reassessment survey results against a potassium serum level reassessment filter of the second category class that is fired at least when the plurality of reassessment survey results indicates that the subject has experienced, since receiving their last provision of the angiotensin II receptor blocker pharmaceutical composition, an abnormal potassium serum level, wherein when the serum potassium level reassessment filter is fired, the subject is provided with a warning corresponding to the serum potassium level reassessment filter.

In some embodiments, the angiotensin II receptor blocker pharmaceutical composition includes valsartan. Accordingly, the plurality of reassessment survey results further includes whether the subject has experienced an impaired renal function since receiving their last provision of the angiotensin II receptor blocker pharmaceutical composition, and the re-fulfillment process includes running all or a portion of the plurality of reassessment survey results against a renal function reassessment filter of a second category class that is fired at least when the plurality of reassessment survey results indicates that the subject has experienced, since receiving their last provision of the angiotensin II receptor blocker pharmaceutical composition, an impaired renal function, wherein when the renal function reassessment filter is fired, the subject is provided with a warning corresponding to the renal function reassessment filter.

In some embodiments, the angiotensin II receptor blocker pharmaceutical composition includes valsartan. Accordingly, the plurality of reassessment survey results further includes whether the subject has experienced an abnormal potassium serum level since receiving their last provision of the angiotensin II receptor blocker pharmaceutical composition, and the re-fulfillment process further includes running all or a portion of the plurality of reassessment survey results against a potassium serum level reassessment filter of the second category class that is fired at least when the plurality of reassessment survey results indicates that the subject has experienced, since receiving their last provision of the angiotensin II receptor blocker pharmaceutical composition, an abnormal potassium serum level, wherein when the serum potassium level reassessment filter is fired, the subject is provided with a warning corresponding to the serum potassium level reassessment filter.

In some embodiments, the pregnancy reassessment filter is also fired when the plurality of reassessment survey results indicates that the subject is planning to become pregnant.

In some embodiments, the drug interaction reassessment filter is fired when the plurality of reassessment survey results indicates that the subject is taking a lithium medication.

In some embodiments, the drug interaction reassessment filter is fired when the plurality of reassessment survey results indicates that the subject is taking a non-steroidal anti-inflammatory medication.

In some embodiments, the drug interaction reassessment filter is fired when the plurality of reassessment survey results indicates that the subject is taking a high blood pressure medication.

In some embodiments, the plurality of reassessment survey results further includes whether the subject has experienced a side effect associated with the angiotensin II receptor blocker pharmaceutical composition since receiving their last provision of the angiotensin II receptor blocker pharmaceutical composition, and the re-fulfillment process further includes running all or a portion of the plurality of reassessment survey results against a side effect reassessment filter of a second category class that is fired at least when plurality of reassessment survey results indicates that the subject has experienced, since receiving their last provision of the angiotensin II receptor blocker pharmaceutical composition, a side effect selected from the group consisting of hypotension, dizziness, and faintness, wherein when the side effect reassessment filter is fired, the subject is provided with a warning corresponding to the side effect reassessment filter.

In some embodiments, the re-fulfillment process further includes, when a respective filter in the first plurality of reassessment filters or second plurality of reassessment filters is fired, storing a record associated with the firing of the respective filter in an adverse event profile comprising records of filter firing events associated with a plurality of subjects.

In some embodiments, the lowering blood pressure is to treat or prevent a heart disease.

In one aspect, a method is provided for lowering blood pressure in a subject in need thereof. The method includes administering an angiotensin II receptor blocker pharmaceutical composition to a subject qualified for over-the-counter access to the angiotensin II receptor blocker pharmaceutical composition. In some embodiments, the subject is qualified using a method and/or system as described herein.

In some embodiments, the angiotensin II receptor blocker pharmaceutical composition includes an active ingredient having the structure:

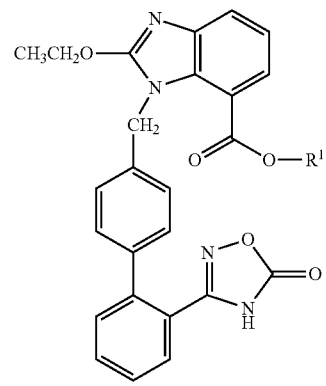

where:
R1 is a group represented by the formula:

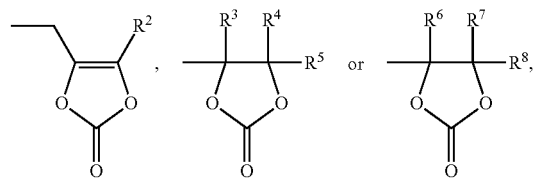

and
R2, R3, R4, R5, R6, R7, and R8 are each independently a hydrogen atom or a C1-6 alkyl, or a salt thereof.

In some embodiments, the angiotensin II receptor blocker pharmaceutical composition includes an active ingredient that is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate or a pharmaceutically acceptable salt thereof.

In some embodiments, the angiotensin II receptor blocker pharmaceutical composition includes an active ingredient that is azilsartan medoxomil or a pharmaceutically acceptable salt thereof.

In some embodiments, the subject is administered from 40 mg to 80 mg of the active ingredient of the angiotensin II receptor blocker pharmaceutical composition per day.

In some embodiments, the angiotensin II receptor blocker pharmaceutical composition comprises an active ingredient that is selected from the group consisting of candesartan, eprosartan, irbesartan, losartan, olmesartan, telmisartan, and valsartan. In some embodiments, the subject is administered from 4 mg to 32 mg of candesartan per day. In some embodiments, the subject is administered from 400 mg to 800 mg of eprosartan per day. In some embodiments, the subject is administered from 75 mg to 300 mg of irbesartan per day. In some embodiments, the subject is administered from 25 mg to 100 mg of losartan per day. In some embodiments, the subject is administered from 5 mg to 40 mg of olmesartan per day. In some embodiments, the subject is administered from 20 mg to 80 mg of telmisartan per day. In some embodiments, the subject is administered from 40 mg to 320 mg of valsartan per day.

In some embodiments, the disclosure provides methods for lowering blood pressure with an over the counter angiotensin II receptor blocker pharmaceutical composition. The method includes providing a first survey for obtaining a first information set from the human, via a computer system having a processor programmed to perform the first survey, where the first information set includes information about the human that relates to potential risk factors and contraindications for the angiotensin II receptor blocker pharmaceutical composition, as described herein. The method also includes applying an algorithm to the first information set, via a computer system having a processor programmed to perform the algorithm. The algorithm runs all or a portion of the first information set against a first plurality of filters, where the human is deemed not qualified for treatment with the over the counter angiotensin II receptor blocker pharmaceutical composition for lowering blood pressure when a respective filter in the first plurality of filters is fired and the method is terminated without authorizing provision of the angiotensin II receptor blocker pharmaceutical composition to the human, where the first plurality of filters includes filters related to contraindications of the angiotensin II receptor blocker pharmaceutical composition as described herein. The algorithm also runs all or a portion of the first information set against a second plurality of filters, where, when a respective filter in the second plurality of filters is fired, the human is provided with a warning corresponding to the respective filter, and where the second plurality of filters includes filters related to risk factors for the angiotensin II receptor blocker pharmaceutical composition as described herein. The algorithm also obtains acknowledgment from the human of the risk factor associated with each warning issued to the human by any filter in the second plurality of filters. In some embodiments, the acknowledgement includes confirmation that the human has discussed the risk factor with a physician. The algorithm proceeds with a fulfillment process when (a) no filter in the first plurality of filters has been fired and (b) the human has acknowledged each warning associated with each filter in the second plurality of filters that was fired. The fulfillment process includes storing an indication in a subject profile of an initial order for the angiotensin II receptor blocker pharmaceutical composition, communicating an over the counter drug facts label for the angiotensin II receptor blocker pharmaceutical composition to the human, and authorizing, upon confirmation from the subject that the over the counter drug facts label has been received and read, provision of the angiotensin II receptor blocker pharmaceutical composition to the human, where the authorization includes a destination associated with the subject. In some embodiments, the method also includes treating the human to lower the blood pressure of the human, upon authorization of the provision e.g., by providing access to the angiotensin II receptor blocker pharmaceutical composition to the human and/or by administering the angiotensin II receptor blocker pharmaceutical composition to lower blood pressure in the human.

EXAMPLES

Example 1—Azilsartan

A computer system is configured for qualifying a subject for over-the-counter delivery of an azilsartan pharmaceutical composition to treat or prevent heart disease (e.g., by lowering blood pressure). The computer system includes instructions for conducting an assessment survey of the subject. The assessment survey is used to obtain one or more of the following results of: whether the subject is one of pregnant, breastfeeding, or planning to become pregnant, whether the subject is taking a medication that interacts with the azilsartan pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, and whether the subject has ever had a kidney problem.

The computer system is configured to run assessment survey results against a first series of assessment filters that are each associated with a first filter category class. The filters of the first filter category class are configured to prevent authorization for OTC delivery of the azilsartan pharmaceutical composition when the assessment survey results indicate the presence of a contraindication for administration of over-the-counter azilsartan. The first series of assessment filters includes a pregnancy assessment filter, a drug interaction assessment filter, a blood pressure assessment filter, an age assessment filter, and a pooled cohort equation assessment filter, configured to be fired as described above.

The computer system is configured to run assessment survey results against a second series of assessment filters that are each associated with a second filter category class. The filters of the second category filter class are configured to generate a warning when the assessment survey results indicate the presence of a risk factor for administration of over-the-counter azilsartan. The second series of assessment filters includes an electrolyte blood level assessment filter and a kidney problem assessment filter, configured to be fired as described above. The computer is configured to prompt the subject to acknowledge having discussed any warnings that are triggered with a medical professional (e.g., their physician or healthcare provider).

The computer system is configured to proceed with a fulfillment process only when none of the first series of assessment filters are fired and the subject has acknowledged each warning associated with second series of assessment filters that are fired. The computer system stores an indication of an initial order of the OTC azilsartan in a subject profile, and communicates an over-the-counter drug facts label for the azilsartan pharmaceutical composition to the subject. Upon confirmation by the subject that they have received and read the over-the-counter drug facts label, the computer system is configured to authorize provision of the OTC azilsartan pharmaceutical composition to the subject.

In some embodiments, the computer system includes instructions for qualifying a subject for a re-order provision of the azilsartan pharmaceutical composition. The computer system is configured to conduct a reassessment survey responsive to a re-order request for the azilsartan pharmaceutical composition by the subject. The reassessment survey is utilized to obtain one or more results of: a systolic blood pressure of the subject, a diastolic blood pressure of the subject, whether the subject is one of pregnant, breastfeeding, or planning to become pregnant, whether the subject is taking a substance that interacts with the azilsartan pharmaceutical composition, whether the subject has experienced symptoms of hypotension since receiving their last provision of the azilsartan pharmaceutical composition, whether the subject has developed an abnormal electrolyte blood level since receiving their last provision of the azilsartan pharmaceutical composition, and whether the subject has developed a kidney problem since receiving their last provision of the azilsartan pharmaceutical composition.

The computer system is configured to run reassessment survey results against a first series of reassessment filters that are each associated with the first filter category class. In some embodiments, the first series of reassessment filters includes a blood pressure reassessment filter, a pregnancy reassessment filter, a drug interaction reassessment filter, a hypotension reassessment filter, an electrolyte blood level reassessment filter, and a kidney problem reassessment filter, configured to be fired as described above.

The computer system then proceeds with a re-fulfillment process only when none of the first series of reassessment filters are fired. The computer system stores an indication of a re-order of the OTC azilsartan in the subject profile, and communicates an over-the-counter drug facts label for the azilsartan pharmaceutical composition to the subject. Upon confirmation by the subject that they have received and read the over-the-counter drug facts label, the computer system is configured to authorize provision of the OTC azilsartan pharmaceutical composition to the subject.

Example 2—Candesartan

A computer system is configured for qualifying a subject for over-the-counter delivery of a candesartan pharmaceutical composition to treat or prevent heart disease (e.g., by lowering blood pressure). The computer system includes instructions for conducting an assessment survey of the subject. The assessment survey is used to obtain one or more of the following results of: whether the subject is one of pregnant, breastfeeding, or planning to become pregnant, whether the subject is taking a medication that interacts with the candesartan pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, whether the subject has ever had a kidney problem, and whether the subject has ever had a liver problem.

The computer system is configured to run assessment survey results against a first series of assessment filters that are each associated with a first filter category class. The filters of the first filter category class are configured to prevent authorization for OTC delivery of the candesartan pharmaceutical composition when the assessment survey results indicate the presence of a contraindication for administration of over-the-counter candesartan. The first series of assessment filters includes a pregnancy assessment filter, a drug interaction assessment filter, a blood pressure assessment filter, an age assessment filter, a pooled cohort equation assessment filter, and a liver disease filter, configured to be fired as described above.

The computer system is configured to run assessment survey results against a second series of assessment filters that are each associated with a second filter category class. The filters of the second category filter class are configured to generate a warning when the assessment survey results indicate the presence of a risk factor for administration of over-the-counter candesartan. The second series of assessment filters includes an electrolyte blood level assessment filter and a kidney problem assessment filter, configured as described above. The computer is configured to prompt the subject to acknowledge having discussed any warnings that are triggered with a medical professional (e.g., their physician or healthcare provider).

The computer system is configured to proceed with a fulfillment process only when none of the first series of assessment filters are fired and the subject has acknowledged each warning associated with second series of assessment filters that are fired. The computer system stores an indication of an initial order of the OTC candesartan in a subject profile, and communicates an over-the-counter drug facts label for the candesartan pharmaceutical composition to the subject. Upon confirmation by the subject that they have received and read the over-the-counter drug facts label, the computer system is configured to authorize provision of the OTC candesartan pharmaceutical composition to the subject.

In some embodiments, the computer system includes instructions for qualifying a subject for a re-order provision of the candesartan pharmaceutical composition. The computer system is configured to conduct a reassessment survey responsive to a re-order request for the candesartan pharmaceutical composition by the subject. The reassessment survey is utilized to obtain one or more results of: a systolic blood pressure of the subject, a diastolic blood pressure of the subject, whether the subject is one of pregnant, breastfeeding, or planning to become pregnant, whether the subject is taking a substance that interacts with the candesartan pharmaceutical composition, whether the subject has experienced symptoms of hypotension since receiving their last provision of the candesartan pharmaceutical composition, whether the subject has developed an abnormal electrolyte blood level since receiving their last provision of the candesartan pharmaceutical composition, whether the subject has developed a kidney problem since receiving their last provision of the candesartan pharmaceutical composition, and whether the subject has developed a liver problem since receiving their last provision of the candesartan pharmaceutical composition.

The computer system is configured to run reassessment survey results against a first series of reassessment filters that are each associated with the first filter category class. In some embodiments, the first series of reassessment filters includes a blood pressure reassessment filter, a pregnancy reassessment filter, a drug interaction reassessment filter, a hypotension reassessment filter, an electrolyte blood level reassessment filter, a kidney problem reassessment filter, and a liver disease reassessment filter, configured as described above.

The computer system then proceeds with a re-fulfillment process only when none of the first series of reassessment filters are fired. The computer system stores an indication of a re-order of the OTC candesartan in the subject profile, and communicates an over-the-counter drug facts label for the candesartan pharmaceutical composition to the subject. Upon confirmation by the subject that they have received and read the over-the-counter drug facts label, the computer system is configured to authorize provision of the OTC candesartan pharmaceutical composition to the subject.

Example 3—Eprosartan

A computer system is configured for qualifying a subject for over-the-counter delivery of an eprosartan pharmaceutical composition to treat or prevent heart disease (e.g., by lowering blood pressure). The computer system includes instructions for conducting an assessment survey of the subject. The assessment survey is used to obtain one or more of the following results of: whether the subject is one of pregnant, breastfeeding, or planning to become pregnant, whether the subject is taking a medication that interacts with the eprosartan pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, and whether the subject has ever had a kidney problem.

The computer system is configured to run assessment survey results against a first series of assessment filters that are each associated with a first filter category class. The filters of the first filter category class are configured to prevent authorization for OTC delivery of the eprosartan pharmaceutical composition when the assessment survey results indicate the presence of a contraindication for administration of over-the-counter eprosartan. The first series of assessment filters includes a pregnancy assessment filter, a drug interaction assessment filter, a blood pressure assessment filter, an age assessment filter, and a pooled cohort equation assessment filter, configured to be fired as described above.

The computer system is configured to run assessment survey results against a second series of assessment filters that are each associated with a second filter category class. The filters of the second category filter class are configured to generate a warning when the assessment survey results indicate the presence of a risk factor for administration of over-the-counter eprosartan. The second series of assessment filters includes an electrolyte blood level assessment filter and a kidney problem assessment filter, configured as described above. The computer is configured to prompt the subject to acknowledge having discussed any warnings that are triggered with a medical professional (e.g., their physician or healthcare provider).

The computer system is configured to proceed with a fulfillment process only when none of the first series of assessment filters are fired and the subject has acknowledged each warning associated with second series of assessment filters that are fired. The computer system stores an indication of an initial order of the OTC eprosartan in a subject profile, and communicates an over-the-counter drug facts label for the eprosartan pharmaceutical composition to the subject. Upon confirmation by the subject that they have received and read the over-the-counter drug facts label, the computer system is configured to authorize provision of the OTC eprosartan pharmaceutical composition to the subject.

In some embodiments, the computer system includes instructions for qualifying a subject for a re-order provision of the eprosartan pharmaceutical composition. The computer system is configured to conduct a reassessment survey responsive to a re-order request for the eprosartan pharmaceutical composition by the subject. The reassessment survey is utilized to obtain one or more results of: a systolic blood pressure of the subject, a diastolic blood pressure of the subject, whether the subject is one of pregnant, breastfeeding, or planning to become pregnant, whether the subject is taking a substance that interacts with the eprosartan pharmaceutical composition, whether the subject has experienced symptoms of hypotension since receiving their last provision of the eprosartan pharmaceutical composition, whether the subject has developed an abnormal electrolyte blood level since receiving their last provision of the eprosartan pharmaceutical composition, and whether the subject has developed a kidney problem since receiving their last provision of the eprosartan pharmaceutical composition.

The computer system is configured to run reassessment survey results against a first series of reassessment filters that are each associated with the first filter category class. In some embodiments, the first series of reassessment filters includes a blood pressure reassessment filter, a pregnancy reassessment filter, a drug interaction reassessment filter, a hypotension reassessment filter, an electrolyte blood level reassessment filter, and a kidney problem reassessment filter, configured as described above.

The computer system then proceeds with a re-fulfillment process only when none of the first series of reassessment filters are fired. The computer system stores an indication of a re-order of the OTC eprosartan in the subject profile, and communicates an over-the-counter drug facts label for the eprosartan pharmaceutical composition to the subject. Upon confirmation by the subject that they have received and read the over-the-counter drug facts label, the computer system is configured to authorize provision of the OTC eprosartan pharmaceutical composition to the subject.

Example 4—Irbesartan

A computer system is configured for qualifying a subject for over-the-counter delivery of an irbesartan pharmaceutical composition to treat or prevent heart disease (e.g., by lowering blood pressure). The computer system includes instructions for conducting an assessment survey of the subject. The assessment survey is used to obtain one or more of the following results of: whether the subject is one of pregnant, breastfeeding, or planning to become pregnant, whether the subject is taking a medication that interacts with the irbesartan pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, whether the subject has ever had a kidney problem, and whether the subject is taking a supplement containing potassium.

The computer system is configured to run assessment survey results against a first series of assessment filters that are each associated with a first filter category class. The filters of the first filter category class are configured to prevent authorization for OTC delivery of the irbesartan pharmaceutical composition when the assessment survey results indicate the presence of a contraindication for administration of over-the-counter irbesartan. The first series of assessment filters includes a pregnancy assessment filter, a drug interaction assessment filter, a blood pressure assessment filter, an age assessment filter, and a pooled cohort equation assessment filter, configured to be fired as described above.

The computer system is configured to run assessment survey results against a second series of assessment filters that are each associated with a second filter category class. The filters of the second category filter class are configured to generate a warning when the assessment survey results indicate the presence of a risk factor for administration of over-the-counter irbesartan. The second series of assessment filters includes an electrolyte blood level assessment filter, a kidney problem assessment filter, and a potassium supplement assessment filter, configured to be fired as described above. The computer is configured to prompt the subject to acknowledge having discussed any warnings that are triggered with a medical professional (e.g., their physician or healthcare provider).

The computer system is configured to proceed with a fulfillment process only when none of the first series of assessment filters are fired and the subject has acknowledged each warning associated with second series of assessment filters that are fired. The computer system stores an indication of an initial order of the OTC irbesartan in a subject profile, and communicates an over-the-counter drug facts label for the irbesartan pharmaceutical composition to the subject. Upon confirmation by the subject that they have received and read the over-the-counter drug facts label, the computer system is configured to authorize provision of the OTC irbesartan pharmaceutical composition to the subject.

In some embodiments, the computer system includes instructions for qualifying a subject for a re-order provision of the irbesartan pharmaceutical composition. The computer system is configured to conduct a reassessment survey responsive to a re-order request for the irbesartan pharmaceutical composition by the subject. The reassessment survey is utilized to obtain one or more results of: a systolic blood pressure of the subject, a diastolic blood pressure of the subject, whether the subject is one of pregnant, breastfeeding, or planning to become pregnant, whether the subject is taking a substance that interacts with the irbesartan pharmaceutical composition, whether the subject has experienced symptoms of hypotension since receiving their last provision of the irbesartan pharmaceutical composition, whether the subject has developed an abnormal electrolyte blood level since receiving their last provision of the irbesartan pharmaceutical composition, whether the subject has developed a kidney problem since receiving their last provision of the irbesartan pharmaceutical composition, and whether the subject has begun taking a supplement containing potassium since receiving their last provision of the irbesartan pharmaceutical composition.

The computer system is configured to run reassessment survey results against a first series of reassessment filters that are each associated with the first filter category class. In some embodiments, the first series of reassessment filters includes a blood pressure reassessment filter, a pregnancy reassessment filter, a drug interaction reassessment filter, a hypotension reassessment filter, an electrolyte blood level reassessment filter, and a kidney problem reassessment filter, configured as described above.

The computer system is configured to run reassessment survey results against a potassium supplement filter associated with the second filter category class.

The computer system then proceeds with a re-fulfillment process only when none of the first series of reassessment filters are fired and the subject has acknowledged each warning associated with second series of reassessment filters that are fired. The computer system stores an indication of a re-order of the OTC irbesartan in the subject profile, and communicates an over-the-counter drug facts label for the irbesartan pharmaceutical composition to the subject. Upon confirmation by the subject that they have received and read the over-the-counter drug facts label, the computer system is configured to authorize provision of the OTC irbesartan pharmaceutical composition to the subject.

Example 5—Losartan

A computer system is configured for qualifying a subject for over-the-counter delivery of an losartan pharmaceutical composition to treat or prevent heart disease (e.g., by lowering blood pressure). The computer system includes instructions for conducting an assessment survey of the subject. The assessment survey is used to obtain one or more of the following results of: whether the subject is one of pregnant, breastfeeding, or planning to become pregnant, whether the subject is taking a medication that interacts with the losartan pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, whether the subject has ever had a kidney problem, whether the subject has ever had liver problems, and whether the subject is taking a supplement containing potassium.

The computer system is configured to run assessment survey results against a first series of assessment filters that are each associated with a first filter category class. The filters of the first filter category class are configured to prevent authorization for OTC delivery of the losartan pharmaceutical composition when the assessment survey results indicate the presence of a contraindication for administration of over-the-counter losartan. The first series of assessment filters includes a pregnancy assessment filter, a drug interaction assessment filter, a blood pressure assessment filter, an age assessment filter, a pooled cohort equation assessment filter, and a liver disease filter, configured to be fired as described above.

The computer system is configured to run assessment survey results against a second series of assessment filters that are each associated with a second filter category class. The filters of the second category filter class are configured to generate a warning when the assessment survey results indicate the presence of a risk factor for administration of over-the-counter losartan. The second series of assessment filters includes an electrolyte blood level assessment filter, a kidney problem assessment filter, and a potassium supplement assessment filter, configured to be fired as described above. The computer is configured to prompt the subject to acknowledge having discussed any warnings that are triggered with a medical professional (e.g., their physician or healthcare provider).

The computer system is configured to proceed with a fulfillment process only when none of the first series of assessment filters are fired and the subject has acknowledged each warning associated with second series of assessment filters that are fired. The computer system stores an indication of an initial order of the OTC losartan in a subject profile, and communicates an over-the-counter drug facts label for the losartan pharmaceutical composition to the subject. Upon confirmation by the subject that they have received and read the over-the-counter drug facts label, the computer system is configured to authorize provision of the OTC losartan pharmaceutical composition to the subject.

In some embodiments, the computer system includes instructions for qualifying a subject for a re-order provision of the losartan pharmaceutical composition. The computer system is configured to conduct a reassessment survey responsive to a re-order request for the losartan pharmaceutical composition by the subject. The reassessment survey is utilized to obtain one or more results of: a systolic blood pressure of the subject, a diastolic blood pressure of the subject, whether the subject is one of pregnant, breastfeeding, or planning to become pregnant, whether the subject is taking a substance that interacts with the losartan pharmaceutical composition, whether the subject has experienced symptoms of hypotension since receiving their last provision of the losartan pharmaceutical composition, whether the subject has developed an abnormal electrolyte blood level since receiving their last provision of the losartan pharmaceutical composition, whether the subject has developed a kidney problem since receiving their last provision of the losartan pharmaceutical composition, whether the subject has developed a liver problem since receiving their last provision of the losartan pharmaceutical composition, and whether the subject has begun taking a supplement containing potassium since receiving their last provision of the losartan pharmaceutical composition.

The computer system is configured to run reassessment survey results against a first series of reassessment filters that are each associated with the first filter category class. In some embodiments, the first series of reassessment filters includes a blood pressure reassessment filter, a pregnancy reassessment filter, a drug interaction reassessment filter, a hypotension reassessment filter, an electrolyte blood level monitor reassessment filter, a kidney problem reassessment filter, and a liver disease reassessment filter, configured as described above.

The computer system is configured to run reassessment survey results against a potassium supplement filter associated with the second filter category class.

The computer system then proceeds with a re-fulfillment process only when none of the first series of reassessment filters are fired and the subject has acknowledged each warning associated with second series of reassessment filters that are fired. The computer system stores an indication of a re-order of the OTC losartan in the subject profile, and communicates an over-the-counter drug facts label for the losartan pharmaceutical composition to the subject. Upon confirmation by the subject that they have received and read the over-the-counter drug facts label, the computer system is configured to authorize provision of the OTC losartan pharmaceutical composition to the subject.

Example 6—Olmesartan

A computer system is configured for qualifying a subject for over-the-counter delivery of an olmesartan pharmaceutical composition to treat or prevent heart disease (e.g., by lowering blood pressure). The computer system includes instructions for conducting an assessment survey of the subject. The assessment survey is used to obtain one or more of the following results of: whether the subject is one of pregnant, breastfeeding, or planning to become pregnant, whether the subject is taking a medication that interacts with the olmesartan pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, whether the subject has ever had a kidney problem, and whether the subject is taking colesevelam.

The computer system is configured to run assessment survey results against a first series of assessment filters that are each associated with a first filter category class. The filters of the first filter category class are configured to prevent authorization for OTC delivery of the olmesartan pharmaceutical composition when the assessment survey results indicate the presence of a contraindication for administration of over-the-counter olmesartan. The first series of assessment filters includes a pregnancy assessment filter, a drug interaction assessment filter, a blood pressure assessment filter, an age assessment filter, and a pooled cohort equation assessment filter, configured to be fired as described above.

The computer system is configured to run assessment survey results against a second series of assessment filters that are each associated with a second filter category class. The filters of the second category filter class are configured to generate a warning when the assessment survey results indicate the presence of a risk factor for administration of over-the-counter olmesartan. The second series of assessment filters includes an electrolyte blood level assessment filter, a kidney problem assessment filter, and a colesevelam filter, configured to be fired as described above. The computer is configured to prompt the subject to acknowledge having discussed any warnings that are triggered with a medical professional (e.g., their physician or healthcare provider).

The computer system is configured to proceed with a fulfillment process only when none of the first series of assessment filters are fired and the subject has acknowledged each warning associated with second series of assessment filters that are fired. The computer system stores an indication of an initial order of the OTC olmesartan in a subject profile, and communicates an over-the-counter drug facts label for the olmesartan pharmaceutical composition to the subject. Upon confirmation by the subject that they have received and read the over-the-counter drug facts label, the computer system is configured to authorize provision of the OTC olmesartan pharmaceutical composition to the subject.

In some embodiments, the computer system includes instructions for qualifying a subject for a re-order provision of the olmesartan pharmaceutical composition. The computer system is configured to conduct a reassessment survey responsive to a re-order request for the olmesartan pharmaceutical composition by the subject. The reassessment survey is utilized to obtain one or more results of: a systolic blood pressure of the subject, a diastolic blood pressure of the subject, whether the subject is one of pregnant, breastfeeding, or planning to become pregnant, whether the subject is taking a substance that interacts with the olmesartan pharmaceutical composition, whether the subject has experienced symptoms of hypotension since receiving their last provision of the olmesartan pharmaceutical composition, whether the subject has developed an abnormal electrolyte blood level since receiving their last provision of the olmesartan pharmaceutical composition, whether the subject has developed a kidney problem since receiving their last provision of the olmesartan pharmaceutical composition, and whether the subject has begun taking colesevelam since receiving their last provision of the olmesartan pharmaceutical composition.

The computer system is configured to run reassessment survey results against a first series of reassessment filters that are each associated with the first filter category class. In some embodiments, the first series of reassessment filters includes a blood pressure reassessment filter, a pregnancy reassessment filter, a drug interaction reassessment filter, a hypotension reassessment filter, an electrolyte blood level reassessment filter, and a kidney problem reassessment filter, configured to be fired as described above.

The computer system is configured to run reassessment survey results against a colesevelam filter associated with the second filter category class.

The computer system then proceeds with a re-fulfillment process only when none of the first series of reassessment filters are fired. The computer system stores an indication of a re-order of the OTC olmesartan in the subject profile, and communicates an over-the-counter drug facts label for the olmesartan pharmaceutical composition to the subject. Upon confirmation by the subject that they have received and read the over-the-counter drug facts label, the computer system is configured to authorize provision of the OTC olmesartan pharmaceutical composition to the subject.

Example 7—Telmisartan

A computer system is configured for qualifying a subject for over-the-counter delivery of a telmisartan pharmaceutical composition to treat or prevent heart disease (e.g., by lowering blood pressure). The computer system includes instructions for conducting an assessment survey of the subject. The assessment survey is used to obtain one or more of the following results of: whether the subject is one of pregnant, breastfeeding, or planning to become pregnant, whether the subject is taking a medication that interacts with the telmisartan pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, whether the subject has ever had a kidney problem, and whether the subject has ever had a liver problem.

The computer system is configured to run assessment survey results against a first series of assessment filters that are each associated with a first filter category class. The filters of the first filter category class are configured to prevent authorization for OTC delivery of the telmisartan pharmaceutical composition when the assessment survey results indicate the presence of a contraindication for administration of over-the-counter telmisartan. The first series of assessment filters includes a pregnancy assessment filter, a drug interaction assessment filter, a blood pressure assessment filter, an age assessment filter, a pooled cohort equation assessment filter, and a liver disease filter, configured to be fired as described above.

The computer system is configured to run assessment survey results against a second series of assessment filters that are each associated with a second filter category class. The filters of the second category filter class are configured to generate a warning when the assessment survey results indicate the presence of a risk factor for administration of over-the-counter telmisartan. The second series of assessment filters includes an electrolyte blood level assessment filter and a kidney problem assessment filter, configured as described above. The computer is configured to prompt the subject to acknowledge having discussed any warnings that are triggered with a medical professional (e.g., their physician or healthcare provider).

The computer system is configured to proceed with a fulfillment process only when none of the first series of assessment filters are fired and the subject has acknowledged each warning associated with second series of assessment filters that are fired. The computer system stores an indication of an initial order of the OTC telmisartan in a subject profile, and communicates an over-the-counter drug facts label for the telmisartan pharmaceutical composition to the subject. Upon confirmation by the subject that they have received and read the over-the-counter drug facts label, the computer system is configured to authorize provision of the OTC telmisartan pharmaceutical composition to the subject.

In some embodiments, the computer system includes instructions for qualifying a subject for a re-order provision of the telmisartan pharmaceutical composition. The computer system is configured to conduct a reassessment survey responsive to a re-order request for the telmisartan pharmaceutical composition by the subject. The reassessment survey is utilized to obtain one or more results of: a systolic blood pressure of the subject, a diastolic blood pressure of the subject, whether the subject is one of pregnant, breastfeeding, or planning to become pregnant, whether the subject is taking a substance that interacts with the telmisartan pharmaceutical composition, whether the subject has experienced symptoms of hypotension since receiving their last provision of the telmisartan pharmaceutical composition, whether the subject has developed an abnormal electrolyte blood level since receiving their last provision of the telmisartan pharmaceutical composition, whether the subject has developed a kidney problem since receiving their last provision of the telmisartan pharmaceutical composition, and whether the subject has developed a liver problem since receiving their last provision of the telmisartan pharmaceutical composition.

The computer system is configured to run reassessment survey results against a first series of reassessment filters that are each associated with the first filter category class. In some embodiments, the first series of reassessment filters includes a blood pressure reassessment filter, a pregnancy reassessment filter, a drug interaction reassessment filter, a hypotension reassessment filter, an electrolyte blood level reassessment filter, a kidney problem reassessment filter, and a liver disease reassessment filter, configured as described above.

The computer system then proceeds with a re-fulfillment process only when none of the first series of reassessment filters are fired. The computer system stores an indication of a re-order of the OTC telmisartan in the subject profile, and communicates an over-the-counter drug facts label for the telmisartan pharmaceutical composition to the subject. Upon confirmation by the subject that they have received and read the over-the-counter drug facts label, the computer system is configured to authorize provision of the OTC telmisartan pharmaceutical composition to the subject.

Example 8—Valsartan

A computer system is configured for qualifying a subject for over-the-counter delivery of a valsartan pharmaceutical composition to treat or prevent heart disease (e.g., by lowering blood pressure). The computer system includes instructions for conducting an assessment survey of the subject. The assessment survey is used to obtain one or more of the following results of: whether the subject is one of pregnant, breastfeeding, or planning to become pregnant, whether the subject is taking a medication that interacts with the valsartan pharmaceutical composition, a systolic blood pressure of the subject, a diastolic blood pressure of the subject, an age of the subject, information required to calculate a risk of atherosclerotic cardiovascular disease for the subject, whether the subject has ever had an abnormal electrolyte blood level, and whether the subject has ever had a kidney problem.

The computer system is configured to run assessment survey results against a first series of assessment filters that are each associated with a first filter category class. The filters of the first filter category class are configured to prevent authorization for OTC delivery of the valsartan pharmaceutical composition when the assessment survey results indicate the presence of a contraindication for administration of over-the-counter valsartan. The first series of assessment filters includes a pregnancy assessment filter, a drug interaction assessment filter, a blood pressure assessment filter, an age assessment filter, and a pooled cohort equation assessment filter, configured to be fired as described above.

The computer system is configured to run assessment survey results against a second series of assessment filters that are each associated with a second filter category class. The filters of the second category filter class are configured to generate a warning when the assessment survey results indicate the presence of a risk factor for administration of over-the-counter valsartan. The second series of assessment filters includes an electrolyte blood level assessment filter and a kidney problem assessment filter, configured to be fired as described above. The computer is configured to prompt the subject to acknowledge having discussed any warnings that are triggered with a medical professional (e.g., their physician or healthcare provider).

The computer system is configured to proceed with a fulfillment process only when none of the first series of assessment filters are fired and the subject has acknowledged each warning associated with second series of assessment filters that are fired. The computer system stores an indication of an initial order of the OTC valsartan in a subject profile, and communicates an over-the-counter drug facts label for the valsartan pharmaceutical composition to the subject. Upon confirmation by the subject that they have received and read the over-the-counter drug facts label, the computer system is configured to authorize provision of the OTC valsartan pharmaceutical composition to the subject.

In some embodiments, the computer system includes instructions for qualifying a subject for a re-order provision of the valsartan pharmaceutical composition. The computer system is configured to conduct a reassessment survey responsive to a re-order request for the valsartan pharmaceutical composition by the subject. The reassessment survey is utilized to obtain one or more results of: a systolic blood pressure of the subject, a diastolic blood pressure of the subject, whether the subject is one of pregnant, breast-feeding, or planning to become pregnant, whether the subject is taking a substance that interacts with the valsartan pharmaceutical composition, whether the subject has experienced symptoms of hypotension since receiving their last provision of the valsartan pharmaceutical composition, whether the subject has developed an abnormal electrolyte blood level since receiving their last provision of the valsartan pharmaceutical composition, and whether the subject has developed a kidney problem since receiving their last provision of the valsartan pharmaceutical composition.

The computer system is configured to run reassessment survey results against a first series of reassessment filters that are each associated with the first filter category class. In some embodiments, the first series of reassessment filters includes a blood pressure reassessment filter, a pregnancy reassessment filter, a drug interaction reassessment filter, a hypotension reassessment filter, an electrolyte blood level reassessment filter, and a kidney problem reassessment filter, configured to be fired as described above.

The computer system then proceeds with a re-fulfillment process only when none of the first series of reassessment filters are fired. The computer system stores an indication of a re-order of the OTC valsartan in the subject profile, and communicates an over-the-counter drug facts label for the valsartan pharmaceutical composition to the subject. Upon confirmation by the subject that they have received and read the over-the-counter drug facts label, the computer system is configured to authorize provision of the OTC valsartan pharmaceutical composition to the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A computer system for qualifying a human subject for over-the-counter delivery of an angiotensin II receptor blocker pharmaceutical composition for lowering blood pressure, the computer system comprising one or more processors and a memory, the memory comprising non-transitory instructions which, when executed by the one or more processor, cause the computer system to perform a method comprising:
   a) conducting an assessment survey of the subject thereby obtaining a plurality of assessment survey results, wherein the plurality of assessment survey results comprises:
      whether the subject is one of (i) pregnant, (ii) breast-feeding, or (iii) planning to become pregnant,
      whether the subject is taking a medication that interacts with the angiotensin II receptor blocker pharmaceutical composition,
      a systolic blood pressure of the subject,
      a diastolic blood pressure of the subject,
      an age of the subject,
      information required to calculate a risk of atherosclerotic cardiovascular disease for the subject,
      whether the subject has ever had an abnormal electrolyte blood level, and
      whether the subject has ever had a kidney problem;
   b) running all or a portion of the plurality of assessment survey results against a first plurality of assessment filters of a first category class, wherein, when a respective filter in the first plurality of assessment filters is fired, the subject is deemed not qualified for delivery of the angiotensin II receptor blocker pharmaceutical composition and the method is terminated without delivery of the angiotensin II receptor blocker pharmaceutical composition to the subject, wherein the first plurality of assessment filters comprises:
      a pregnancy assessment filter that is fired at least when the plurality of assessment survey results indicates that the subject is pregnant or the subject is breast-feeding,
      a drug interaction assessment filter that is fired at least when the plurality of assessment survey results indicate that the subject is taking a medication that interacts with the angiotensin II receptor blocker pharmaceutical composition, a blood pressure assessment filter that is fired at least when the plurality of assessment survey results indicates the subject is not hypertensive or the subject has severe hypertension, an age assessment filter that is fired at least when the plurality of assessment survey results indicate the subject is too young to receive the angiotensin II receptor blocker pharmaceutical composition, and a pooled cohort equation assessment filter that is fired at least when the plurality of assessment survey results indicate that the subject has a risk for atherosclerotic cardiovascular disease that is below a floor threshold of risk or the subject has an incalculable risk for atherosclerotic cardiovascular disease;

c) running all or a portion of the plurality of assessment survey results against a second plurality of assessment filters of a second category class, wherein, when a respective filter in the second plurality of assessment filters is fired, the subject is provided with a warning corresponding to the respective filter, and wherein the second plurality of assessment filters comprises:

an electrolyte blood level assessment filter that is fired at least when the plurality of assessment survey results indicates that the subject has had an abnormal electrolyte blood level, and a kidney problem assessment filter that is fired at least when the plurality of assessment survey results indicates that the subject has had a kidney problem, d) obtaining acknowledgment from the subject for the warning issued to the subject by any filter in the second plurality of filters; and e) proceeding with a fulfillment process when (i) no filter in the first plurality of filters has been fired and (ii) the subject has acknowledged each warning associated with each filter in the second plurality of filters that was fired, wherein the fulfillment process comprises:

storing an indication in a subject profile of an initial order for the angiotensin II receptor blocker pharmaceutical composition, communicating an over the counter drug facts label for the angiotensin II receptor blocker pharmaceutical composition to the subject, and authorizing, upon confirmation from the subject that the over the counter drug facts label has been received and read, provision of the angiotensin II receptor blocker pharmaceutical composition to the subject; and wherein the angiotensin II receptor blocker pharmaceutical composition is administered to the subject after provision of the angiotensin II receptor blocker pharmaceutical composition has been authorized for the subject.

2. The computer system of claim 1, wherein the angiotensin II receptor blocker pharmaceutical composition comprises an active ingredient that is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate or a pharmaceutically acceptable salt thereof.

3. The computer system of claim 1, wherein the angiotensin II receptor blocker pharmaceutical composition comprises an active ingredient that is azilsartan medoxomil or a pharmaceutically acceptable salt thereof.

4. The computer system of claim 3, wherein, upon confirmation from the subject that the over the counter drug facts label has been received and read, the subject is authorized for provision of a dosage of from 40 mg to 80 mg per day of the active ingredient of the angiotensin II receptor blocker pharmaceutical composition.

5. The computer system according to claim 1, wherein the active ingredient of the angiotensin II receptor blocker pharmaceutical composition comprises an active ingredient selected from the group consisting of candesartan, eprosartan, irbesartan, losartan, olmesartan, telmisartan, and valsartan.

6. The computer system according to claim 5, wherein, upon confirmation from the subject that the over the counter drug facts label has been received and read, the subject is authorized for provision of a dosage of from 4 mg to 32 mg of candesartan per day.

7. The computer system according to claim 5, wherein:
the angiotensin II receptor blocker pharmaceutical composition comprises candesartan,
the plurality of assessment survey results further comprises whether the subject has a liver problem, and
the first plurality of assessment filters includes a liver problem assessment filter that is fired at least when the plurality of assessment survey results indicates that the subject has advanced liver disease.

8. The computer system according to claim 5, wherein, upon confirmation from the subject that the over the counter drug facts label has been received and read, the subject is authorized for provision of a dosage of from 400 mg to 800 mg of eprosartan per day.

9. The computer system according to claim 5, wherein, upon confirmation from the subject that the over the counter drug facts label has been received and read, the subject is authorized for provision of a dosage from 75 mg to 300 mg of irbesartan per day.

10. The computer system according to claim 5, wherein, upon confirmation from the subject that the over the counter drug facts label has been received and read, the subject is authorized for provision of a dosage of from 25 mg to 100 mg of losartan per day.

11. The computer system according to claim 5, wherein:
the angiotensin II receptor blocker pharmaceutical composition comprises losartan,
the plurality of assessment survey results further comprises whether the subject is taking a potassium supplement or a salt substitute that includes potassium, and
the second plurality of assessment filters includes a potassium supplement assessment filter that is fired at least when the plurality of assessment survey results indicates that the subject is taking a potassium supplement or a salt substitute that includes potassium.

12. The computer system according to claim 5, wherein:
the angiotensin II receptor blocker pharmaceutical composition comprises losartan,
the plurality of assessment survey results further comprises whether the subject has ever had a liver problem, and
the first plurality of assessment filters includes a liver problem assessment filter that is fired at least when the plurality of assessment survey results indicates that the subject has had a liver problem.

13. The computer system according to claim 5, wherein, upon confirmation from the subject that the over the counter drug facts label has been received and read, the subject is authorized for provision of a dosage of from 5 mg to 40 mg of olmesartan per day.

14. The computer system according to claim 5, wherein:
the angiotensin II receptor blocker pharmaceutical composition comprises olmesartan, the plurality of assessment survey results further comprises whether the subject is taking colesevelam, and the second plurality of assessment filters includes a colesevelam interaction assessment filter that is fired at least when the plurality of assessment survey results indicates that the subject is taking colesevelam.

15. The computer system according to claim 5, wherein, upon confirmation from the subject that the over the counter drug facts label has been received and read, the subject is authorized for provision of a dosage of from 20 mg to 80 mg of telmisartan per day.

16. The computer system according to claim 5, wherein:
the angiotensin II receptor blocker pharmaceutical composition comprises telmisartan, and
the first drug interaction assessment filter is fired when the plurality of assessment survey results indicates that the subject is taking digoxin.

17. The computer system according to claim 5, wherein:
the angiotensin II receptor blocker pharmaceutical composition comprises telmisartan,
the plurality of assessment survey results further comprises whether the subject has ever had a liver problem, and
the second plurality of assessment filters includes a liver problem assessment filter that is fired at least when the plurality of assessment survey results indicates that the subject has had a liver problem.

18. The computer system according to claim 5, wherein:
the angiotensin II receptor blocker pharmaceutical composition comprises telmisartan,
the plurality of assessment survey results further comprises whether the subject is taking a potassium supplement or a salt substitute that includes potassium, and
the second plurality of assessment filters includes a potassium supplement assessment filter that is fired at least when the plurality of assessment survey results indicates that the subject is taking a potassium supplement or a salt substitute that includes potassium.

19. The computer system according to claim 5, wherein:
the angiotensin II receptor blocker pharmaceutical composition comprises telmisartan,
the plurality of assessment survey results further comprises whether the subject has ever had a heart failure, and
the second plurality of assessment filters includes a heart failure assessment filter that is fired at least when the plurality of assessment survey results indicates that the subject has had a heart failure.

20. The computer system according to claim 5, wherein, upon confirmation from the subject that the over the counter drug facts label has been received and read, the subject is authorized for provision of a dosage of from 40 mg to 320 mg of valsartan per day.

21. The computer system of claim 1, wherein the first drug interaction assessment filter is fired when the plurality of assessment survey results indicates that the subject is taking a lithium medication.

22. The computer system of claim 1, wherein the first drug interaction assessment filter is fired when the plurality of assessment survey results indicates that the subject is taking a non-steroidal anti-inflammatory medication.

23. The computer system of claim 1, wherein the first drug interaction assessment filter is fired when the plurality of assessment survey results indicates that the subject is taking a high blood pressure medication.

24. The computer system of claim 1, wherein the performed method further comprises, when the plurality of assessment survey results indicate that the subject has stage two hypertension:
firing the blood pressure assessment filter; and
transmitting, to the subject, advice to visit a doctor to discuss taking a prescription-strength blood pressure medication.

25. The computer system of claim 1, wherein the performed method further comprises, when the plurality of assessment survey results indicate that the subject is in hypertensive crisis:
firing the blood pressure assessment filter; and
transmitting, to the subject, advice to seek emergency medical attention.

26. The computer system of claim 1, wherein the pooled cohort equation assessment filter is fired when the plurality of assessment survey results indicates that the subject has a 10-year risk for atherosclerotic cardiovascular disease, as determined using a pooled cohort equation, that is less than 10%.

27. The computer system of claim 26, wherein the pooled cohort equation assessment filter is fired when the plurality of assessment survey results indicates that the subject has an incalculable risk for atherosclerotic cardiovascular disease, as determined by one or more inputs of the pooled cohort equation, including:
A) the subject is younger than forty years old,
B) a total cholesterol level of the subject is either less than 160 mg/dL or greater than 240 mg/dL,
C) a high density lipoprotein cholesterol level of the subject is less than 45 mg/dL or greater than 65 mg/dL,
D) an untreated systolic blood pressure of the subject is less than 100 mm Hg or greater than 140 mm Hg, or
E) a treated systolic blood pressure of the subject is less than 120 mm Hg or greater than 160 mm Hg.

28. The computer system of claim 1, wherein the method includes bypassing the firing of the pooled cohort equation assessment filter when the plurality of assessment survey results indicates that the subject has an incalculable risk for atherosclerotic cardiovascular disease but has an age that is above a risk threshold age.

29. The computer system of claim 1, wherein
the plurality of assessment survey results further comprises:
a gender of the subject,
a race of the subject,
a blood pressure medication status of the subject,
a smoking status of the subject,
a total cholesterol level of the subject,
a high density lipoprotein cholesterol level of the subject,
whether the subject has ever had an atherosclerotic cardiovascular history including an atherosclerotic cardiovascular event or a heart procedure, and
a diabetes status of the subject; and
the pooled cohort equation assessment filter incorporates the gender of the subject, the age of the subject, the race of the subject, the blood pressure medication status of the subject, the smoking status of the subject, the total cholesterol of the subject, the high density lipoprotein cholesterol level of the subject, the atherosclerotic cardiovascular history of the subject, and the diabetes status of the subject to derive the risk for atherosclerotic cardiovascular disease.

30. The computer system of claim 1, wherein the pooled cohort equation filter utilizes a pooled cohort equation implemented as a multivariable Cox proportional hazard regression.

31. The computer system of claim 1, wherein:
the warning corresponding to a respective filter in the second plurality of assessment filters comprises a prompt for the subject to indicate whether they have discussed the risk factor underlying the respective filter in the second plurality of assessment filters that was fired with a health care provider; and
acknowledgement is obtained from the subject when the subject indicates that they have discussed the risk factor underlying the respective filter in the second plurality of assessment filters that was fired with a health care provider.

32. The computer system of claim 1, wherein the fulfillment process further comprises:
storing a destination associated with the subject in the subject profile.

33. The computer system of claim 1, wherein the fulfillment process further comprises:
coordinating shipping of the angiotensin II receptor blocker pharmaceutical composition to a physical address associated with the subject.

34. The computer system according to claim 1, wherein the pregnancy assessment filter is also fired when the plurality of assessment survey results indicates that the subject is planning to become pregnant.

35. The computer system according to claim 1, wherein blood pressure that indicates the subject is not hypertensive, and is capable of firing the blood pressure assessment filter, is a systolic blood pressure of less than 130 mm Hg and a diastolic blood pressure of less than 80 mm Hg.

36. The computer system according to claim 1, wherein blood pressure that indicates the subject has severe hypertension, and is capable of firing the blood pressure assessment filter, is a systolic blood pressure of at least 140 mm Hg or a diastolic blood pressure of at least 90 mm Hg.

37. The computer system according to claim 1, wherein the performed method further comprises, when the plurality of assessment survey results indicate that the subject has elevated blood pressure but is not hypertensive:
firing the blood pressure assessment filter; and
transmitting, to the subject, advice to manage their blood pressure by eating healthy and exercising.

38. The computer system according to claim 1, wherein:
the plurality of assessment survey results further comprises whether the subject is allergic to the angiotensin II receptor block pharmaceutical composition, and
the first plurality of assessment filters includes an adverse reaction assessment filter that is fired when the plurality of assessment survey results indicates that the subject is allergic to the angiotensin II receptor blocker pharmaceutical composition.

39. The computer system according to claim 1, wherein the lowering blood pressure is to treat or prevent a heart disease.

40. A computer system for requalifying a human subject for over-the-counter delivery of an angiotensin II receptor blocker pharmaceutical composition for lowering blood pressure, the computer system comprising one or more processors and a memory, the memory comprising non-transitory instructions which, when executed by the one or more processor, perform a re-fulfillment method comprising, responsive to receiving a re-order request from the subject for the angiotensin II receptor blocker pharmaceutical composition:
(a) conducting a reassessment survey of the subject thereby obtaining a plurality of reassessment survey results, wherein the plurality of reassessment survey results comprises:
a systolic blood pressure of the subject,
a diastolic blood pressure of the subject,
whether the subject is one of (i) pregnant, (ii) breast-feeding, or (iii) planning to become pregnant,
whether the subject is taking a medication that interacts with the angiotensin II receptor blocker pharmaceutical composition,
whether the subject has experienced symptoms of hypotension since receiving their last provision of the angiotensin II receptor blocker pharmaceutical composition,
whether the subject has developed an abnormal electrolyte blood level since receiving their last provision of the angiotensin II receptor blocker pharmaceutical composition, and
whether the subject has developed a kidney problem since receiving their last provision of the angiotensin II receptor blocker pharmaceutical composition,
(b) running all or a portion of the plurality of reassessment survey results against a first plurality of reassessment filters of a first category class, wherein, when a respective filter in the first plurality of reassessment filters is fired, the subject is deemed not qualified for the angiotensin II receptor blocker pharmaceutical composition and the re-fulfillment process is terminated without delivery of the angiotensin II receptor blocker pharmaceutical composition to the subject, wherein the first plurality of reassessment filters comprise:
a blood pressure reassessment filter that is fired at least when the plurality of reassessment survey results indicates the subject has hypertension,
a pregnancy reassessment filter that is fired at least when the plurality of reassessment survey results indicates the subject is pregnant or the subject is breastfeeding,
a drug interaction reassessment filter that is fired at least when the plurality of reassessment survey results indicates the subject is taking a medication that interacts with the angiotensin II receptor blocker pharmaceutical composition
a hypotension reassessment filter that is fired at least when the plurality of reassessment survey results indicates that the subject has experienced symptoms of hypotension since receiving their last provision of the angiotensin II receptor blocker pharmaceutical composition,
an electrolyte blood level reassessment filter that is fired at least when the plurality of reassessment survey results indicates that the subject has developed an abnormal electrolyte blood level since receiving their last provision of the angiotensin II receptor blocker pharmaceutical composition, and
a kidney problem reassessment filter that is fired at least when the plurality of reassessment survey results indicates that the subject has developed a kidney problem since receiving their last provision of the angiotensin II receptor blocker pharmaceutical composition; and
(c) proceeding with the re-fulfillment when (a) the re-fulfillment is not already terminated by the firing of a filter in the first plurality of reassessment filters, wherein the re-fulfillment further comprises:
storing an indication in the subject profile of a re-order for the angiotensin II receptor blocker pharmaceutical composition,
communicating the over the counter drug facts label for the angiotensin II receptor blocker pharmaceutical composition to the subject, and
authorizing, upon confirmation from the subject that the over the counter drug facts label has been received and read, a re-order provision of the angiotensin II receptor blocker pharmaceutical composition to the subject; and
wherein the angiotensin II receptor blocker pharmaceutical composition is administered to the subject after a re-order provision of the angiotensin II receptor blocker pharmaceutical composition has been authorized for the subject.

41. The computer system according to claim 40, wherein the angiotensin II receptor blocker pharmaceutical composition is selected from the group consisting of azilsartan medoxomil, candesartan, eprosartan, irbesartan, losartan, olmesartan, telmisartan, and valsartan.

42. The computer system according to claim 41, wherein:
the angiotensin II receptor blocker pharmaceutical composition comprises irbesartan,
the plurality of reassessment survey results further comprises whether the subject has experienced an impaired renal function since receiving their last provision of the angiotensin II receptor blocker pharmaceutical composition, and
the re-fulfillment process includes running all or a portion of the plurality of reassessment survey results against a renal function reassessment filter of a second category class that is fired at least when the plurality of reassessment survey results indicates that the subject has experienced, since receiving their last provision of the angiotensin II receptor blocker pharmaceutical composition, an impaired renal function, wherein when the renal function reassessment filter is fired, the subject is provided with a warning corresponding to the renal function reassessment filter.

43. The computer system according to claim 41, wherein:
the angiotensin II receptor blocker pharmaceutical composition comprises irbesartan,
the plurality of reassessment survey results further comprises whether the subject has experienced an abnormal potassium serum level since receiving their last provision of the angiotensin II receptor blocker pharmaceutical composition, and
the re-fulfillment process further comprises running all or a portion of the plurality of reassessment survey results against a potassium serum level reassessment filter of a second category class that is fired at least when the plurality of reassessment survey results indicates that the subject has experienced, since receiving their last provision of the angiotensin II receptor blocker pharmaceutical composition, an abnormal potassium serum level, wherein when the serum potassium level reassessment filter is fired, the subject is provided with a warning corresponding to the serum potassium level reassessment filter.

44. The computer system according to claim 41, wherein:
the angiotensin II receptor blocker pharmaceutical composition comprises losartan,
the plurality of reassessment survey results further comprises whether the subject has experienced an impaired renal function since receiving their last provision of the angiotensin II receptor blocker pharmaceutical composition, and
the re-fulfillment process includes running all or a portion of the plurality of reassessment survey results against a renal function reassessment filter of a second category class that is fired at least when the plurality of reassessment survey results indicates that the subject has experienced, since receiving their last provision of the angiotensin II receptor blocker pharmaceutical composition, an impaired renal function, wherein when the renal function reassessment filter is fired, the subject is provided with a warning corresponding to the renal function reassessment filter.

45. The computer system according to claim 41, wherein:
the angiotensin II receptor blocker pharmaceutical composition comprises losartan,
the plurality of reassessment survey results further comprises whether the subject has experienced an abnormal potassium serum level since receiving their last provision of the angiotensin II receptor blocker pharmaceutical composition, and
the re-fulfillment process further comprises running all or a portion of the plurality of reassessment survey results against a potassium serum level reassessment filter of a second category class that is fired at least when the plurality of reassessment survey results indicates that the subject has experienced, since receiving their last provision of the angiotensin II receptor blocker pharmaceutical composition, an abnormal potassium serum level, wherein when the serum potassium level reassessment filter is fired, the subject is provided with a warning corresponding to the serum potassium level reassessment filter.

46. The computer system according to claim 41, wherein:
the angiotensin II receptor blocker pharmaceutical composition comprises telmisartan,
the plurality of reassessment survey results further comprises whether the subject has experienced an impaired renal function since receiving their last provision of the angiotensin II receptor blocker pharmaceutical composition, and
the re-fulfillment process includes running all or a portion of the plurality of reassessment survey results against a renal function reassessment filter of a second category class that is fired at least when the plurality of reassessment survey results indicates that the subject has experienced, since receiving their last provision of the angiotensin II receptor blocker pharmaceutical composition, an impaired renal function, wherein when the renal function reassessment filter is fired, the subject is provided with a warning corresponding to the renal function reassessment filter.

47. The computer system according to claim 41, wherein:
the angiotensin II receptor blocker pharmaceutical composition comprises telmisartan,
the plurality of reassessment survey results further comprises whether the subject has experienced an abnormal potassium serum level since receiving their last provision of the angiotensin II receptor blocker pharmaceutical composition, and
the re-fulfillment process further comprises running all or a portion of the plurality of reassessment survey results against a potassium serum level reassessment filter of a second category class that is fired at least when the plurality of reassessment survey results indicates that the subject has experienced, since receiving their last provision of the angiotensin II receptor blocker pharmaceutical composition, an abnormal potassium serum level, wherein when the serum potassium level reassessment filter is fired, the subject is provided with a warning corresponding to the serum potassium level reassessment filter.

48. The computer system according to claim 41, wherein:

the angiotensin II receptor blocker pharmaceutical composition comprises valsartan, the plurality of reassessment survey results further comprises whether the subject has experienced an impaired renal function since receiving their last provision of the angiotensin II receptor blocker pharmaceutical composition, and the re-fulfillment process includes running all or a portion of the plurality of reassessment survey results against a renal function reassessment filter of a second category class that is fired at least when the plurality of reassessment survey results indicates that the subject has experienced, since receiving their last provision of the angiotensin II receptor blocker pharmaceutical composition, an impaired renal function, wherein when the renal function reassessment filter is fired, the subject is provided with a warning corresponding to the renal function reassessment filter.

49. The computer system according to claim 41, wherein:

the angiotensin II receptor blocker pharmaceutical composition comprises valsartan, the plurality of reassessment survey results further comprises whether the subject has experienced an abnormal potassium serum level since receiving their last provision of the angiotensin II receptor blocker pharmaceutical composition, and the re-fulfillment process further comprises running all or a portion of the plurality of reassessment survey results against a potassium serum level reassessment filter of a second category class that is fired at least when the plurality of reassessment survey results indicates that the subject has experienced, since receiving their last provision of the angiotensin II receptor blocker pharmaceutical composition, an abnormal potassium serum level, wherein when the serum potassium level reassessment filter is fired, the subject is provided with a warning corresponding to the serum potassium level reassessment filter.

50. The computer system according to claim 40, wherein the pregnancy reassessment filter is also fired when the plurality of reassessment survey results indicates that the subject is planning to become pregnant.

51. The computer system according to claim 40, wherein the drug interaction reassessment filter is fired when the plurality of reassessment survey results indicates that the subject is taking a lithium medication.

52. The computer system according to claim 40, wherein the drug interaction reassessment filter is fired when the plurality of reassessment survey results indicates that the subject is taking a non-steroidal anti-inflammatory medication.

53. The computer system according to claim 40, wherein the drug interaction reassessment filter is fired when the plurality of reassessment survey results indicates that the subject is taking a high blood pressure medication.

54. The computer system according to claim 40, wherein:

the plurality of reassessment survey results further comprises whether the subject has experienced a side effect associated with the angiotensin II receptor blocker pharmaceutical composition since receiving their last provision of the angiotensin II receptor blocker pharmaceutical composition, and the re-fulfillment process further comprises running all or a portion of the plurality of reassessment survey results against a side effect reassessment filter of a second category class that is fired at least when plurality of reassessment survey results indicates that the subject has experienced, since receiving their last provision of the angiotensin II receptor blocker pharmaceutical composition, a side effect selected from the group consisting of hypotension, dizziness, and faintness, wherein when the side effect reassessment filter is fired, the subject is provided with a warning corresponding to the side effect reassessment filter.

55. The computer system according to claim 40, wherein the re-fulfillment process further comprises, when a respective filter in the first plurality of reassessment filters is fired, storing a record associated with the firing of the respective filter in an adverse event profile comprising records of filter firing events associated with a plurality of subjects.

56. The computer system according to claim 40, wherein the lowering blood pressure is to treat or prevent a heart disease.

\* \* \* \* \*